United States Patent
Moore et al.

(10) Patent No.: US 10,086,093 B2
(45) Date of Patent: Oct. 2, 2018

(54) MIRNA PROFILING COMPOSITIONS AND METHODS OF USE

(71) Applicant: THE GENERAL HOSPITAL CORPORATION, Boston, MA (US)

(72) Inventors: Anna V. Moore, Dracut, MA (US); Zdravka Medarova, Methuen, MA (US)

(73) Assignee: THE GENERAL HOSPITAL CORPORATION, Boston, MA (US)

( * ) Notice: Subject to any disclaimer, the term of this patent is extended or adjusted under 35 U.S.C. 154(b) by 260 days.

(21) Appl. No.: 14/769,398

(22) PCT Filed: Feb. 26, 2014

(86) PCT No.: PCT/US2014/018628
§ 371 (c)(1),
(2) Date: Aug. 20, 2015

(87) PCT Pub. No.: WO2014/134144
PCT Pub. Date: Sep. 4, 2014

(65) Prior Publication Data
US 2016/0000940 A1    Jan. 7, 2016

Related U.S. Application Data

(60) Provisional application No. 61/862,273, filed on Aug. 5, 2013, provisional application No. 61/770,526, filed on Feb. 28, 2013.

(51) Int. Cl.
*C12Q 1/68* (2018.01)
*A61K 49/10* (2006.01)
(Continued)

(52) U.S. Cl.
CPC ............ *A61K 49/10* (2013.01); *C12N 15/111* (2013.01); *C12Q 1/6818* (2013.01);
(Continued)

(58) Field of Classification Search
None
See application file for complete search history.

(56) References Cited

U.S. PATENT DOCUMENTS
4,336,173 A    6/1982  Ugelstad
4,421,660 A   12/1983  Hajna
(Continued)

FOREIGN PATENT DOCUMENTS
WO    1994/009699 A1    5/1994
WO    1995/006128 A2    3/1995
(Continued)

OTHER PUBLICATIONS

Akinc et al., "A combinatorial library of lipid-like materials for delivery of RNAi therapeutics", Nat Biotechnol 26(5) 561-569 (2008).
(Continued)

*Primary Examiner* — Robert T. Crow
(74) *Attorney, Agent, or Firm* — Nixon Peabody LLP; David S. Resnick; Shayne Y. Huff

(57) ABSTRACT

Disclosed herein is a nanosensor of miRNA activity in a target cell, and methods of use, for detection and diagnostic applications. The nanosensor comprises a delivery particle comprising an iron oxide crystal coated with a polymer; and a sensor oligonucleotide covalently attached to the polymer. The sensor oligonucleotide comprises a seed region, comprising a nucleic acid sequence that is completely complementary to the target miRNA and comprises a cleavage site which can be engaged and cleaved by the target miRNA.

18 Claims, 28 Drawing Sheets
Specification includes a Sequence Listing.

(51) Int. Cl.
    *C12N 15/11*      (2006.01)
    *C12Q 1/6825*     (2018.01)
    *C12Q 1/6886*     (2018.01)
    *C12Q 1/6818*     (2018.01)
    *A61K 9/00*       (2006.01)
(52) U.S. Cl.
    CPC ......... *C12Q 1/6825* (2013.01); *C12Q 1/6886* (2013.01); *A61K 9/0019* (2013.01); *C12N 2310/141* (2013.01); *C12N 2320/10* (2013.01); *C12Q 2525/207* (2013.01); *C12Q 2545/114* (2013.01); *C12Q 2600/158* (2013.01); *C12Q 2600/178* (2013.01)

(56) References Cited

U.S. PATENT DOCUMENTS

| | | |
|---|---|---|
| 4,490,436 A | 12/1984 | Kawakami |
| 4,554,088 A | 11/1985 | Whitehead |
| 4,654,267 A | 3/1987 | Ugelstad |
| 4,770,183 A | 9/1988 | Groman |
| 4,774,265 A | 9/1988 | Ugelstad |
| 4,965,007 A | 10/1990 | Yudelson |
| 5,091,206 A | 2/1992 | Wang |
| 5,232,789 A | 8/1993 | Platz |
| 5,283,079 A | 2/1994 | Wang |
| 5,302,523 A | 4/1994 | Coffee |
| 5,318,797 A | 6/1994 | Matijevic |
| 5,322,783 A | 6/1994 | Tomes |
| 5,356,713 A | 10/1994 | Charmot |
| 5,384,253 A | 1/1995 | Krzyzek |
| 5,395,688 A | 3/1995 | Wang |
| 5,464,765 A | 11/1995 | Coffee |
| 5,538,877 A | 7/1996 | Lundquist |
| 5,538,880 A | 7/1996 | Lundquist |
| 5,550,318 A | 8/1996 | Adams |
| 5,563,055 A | 10/1996 | Townsend |
| 5,580,859 A | 12/1996 | Felgner |
| 5,610,042 A | 3/1997 | Chang |
| 5,702,932 A | 12/1997 | Hoy |
| 5,736,524 A | 4/1998 | Content |
| 5,780,448 A | 7/1998 | Davis |
| 5,789,215 A | 8/1998 | Berns |
| 5,834,121 A | 11/1998 | Sucholeiki |
| 5,945,100 A | 8/1999 | Fick |
| 5,981,274 A | 11/1999 | Lorne |
| 5,994,624 A | 11/1999 | Trolinder |
| 2008/0056998 A1 | 3/2008 | Wellington |
| 2009/0325169 A1 | 12/2009 | Walder et al. |
| 2010/0297627 A1 | 11/2010 | Watson |
| 2012/0135874 A1 | 5/2012 | Wang et al. |
| 2016/0000940 A1* | 1/2016 | Moore ............... C12Q 1/6825 424/9.3 |

FOREIGN PATENT DOCUMENTS

| | | |
|---|---|---|
| WO | 2010/111066 A2 | 9/2010 |
| WO | 2013016126 A1 | 1/2013 |

OTHER PUBLICATIONS

Akinc et al., "Exploring polyethylenimine-mediated DNA transfection and the proton sponge hypothesis", J Gene Med 7(5) 657-663 (2005).

Baffa et al., "MicroRNA expression profiling of human metastatic cancers identifies cancer gene targets", J Pathol 219(2) 214-221 (2009).

Bracken et al., "Global analysis of the mammalian RNA degradome reveals widespread miRNA-dependent and miRNA-independent endonucleolytic cleavage", Nucleic Acids Res 39(13) 5658-5668 (2011).

Bremer et al., "Optical imaging of matrix metalloproteinase-2 activity in tumors: feasibility study in a mouse model", Radiology 221(2) 523-529 (2001).

Brown et al., "Target accessibility dictates the potency of human RISC", Nat Struct Mol Biol 12(5) 469-470 (2005).

Buckley et al., "Chromosomal and microRNA expression patterns reveal biologically distinct subgroups of 11q-neuroblastoma", Blin Cancer Res 16(11) 2971-2978 (2010).

Burk et al., "A reciprocal repression between ZEB1 and members of the miR-200 family promotes EMT and invasion in cancer cells", EMBO Rep 9(6) 582-589 (2008).

Caramuta et al., "MicroRNA expression profiles associated with mutational status and survival in malignant melanoma", J Invest Dermatol 130(8) 2062-2070 (2010).

Chen et al., "Inhibition of c-FLIP expression by miR-512-3p contributes to taxol-induced apoptosis in hepatocellular carcinoma cells", Oncol Rep 23(5) 1457-1462 (2010).

Creighton et al., "Molecular profiling uncovers a p53-associated role for microRNA-31 in inhibiting the proliferation of serous ovarian carcinomas and other cancers", Cacncer Res 70(5) 1906-1915 (2010).

Driskell et al., "Quantitative surface-enhanced Raman spectroscopy based analysis of microRNA mixtures", Appl Sepctrosc 63(10) 1107-1114 (2009).

Dykxhoorn et al., "miR-200 enhances mouse breast cancer cell colonization to form distant metastases", PLoS One 4(9) e7181 (2009).

Foekens et al., "Four miRNAs associated with aggressiveness of lymph node-negative, estrogen receptor-positive human breast cancer", Proc Natl Acad Sci USA 105(35) 13021-13026 (2008).

Foley et al., "MicroRNA-184 inhibits neuroblastoma cell survival through targeting the serine/threonine kinase AKT2", Mol Cancer 9:83 (2010).

Gabriely et al., "Human glioma growth is controlled by microRNA-10b", Cancer Res 71(10) 3563-3572 (2011).

Garzon et al., "MicroRNA signatures associated with cytogenetics and prognosis in acute myeloid leukemia", Blood 111(6) 3183-3189 (2008).

Gravgaard et al., "The miRNA-200 family and miRNA-9 exhibit differential expression in primary versus corresponding metastatic tissue in breast cancer", Breast Cancer Res Treat 134(1) 207-217 (2012).

Gregory et al., "The miR-200 family and miR-205 regulate epithelial to mesenchymal transition by targeting ZEB1 and SIP1", Nat Cell Biol 10(5) 593-601 (2008).

Harisinghani et al., "Noninvasive detection of clinically occult lymph-node metastases in prostate cancer", N Engl J Med 348(25) 2491-2499 (2003).

Havelda et al., "In situ detection of miRNAs using LNA probes", Methods Mol Biol 592: 127-136 (2010).

Hu et al., "Antisense oligonucleotide against miR-21 inhibits migration and induces apoptosis in leukemic K562 cells", Leuk Lympohma 51(4) 694-701 (2010).

Huang et al., "Up-regulation of miR-21 by HER2/neu signaling promotes cell invastion", J Biol Chem 284(27) 18515-18524 (2009).

Hui et al., "Comprehensive MicroRNA profiling for head and neck squamous cell carcinomas", Clin Cancer Res 16(4) 1129-1139 (2010).

Hurst et al., Metastamir: the field of metastasis-regulatory microRNA is spreading, Cancer Res 69(19) 7495-7498 (2009).

Husale et al., "DNA nanomechanics allows direct digial detectino of complementary DNA and microRNA targets", Nature 462(7276) 1075-1078 (2009).

Hwang et al., "Smart magnetic fluorescent nanoparticle imaging probes to montior microRNAs", Small 6(1) 81-88 (2010).

Ifediba et al., "In vivo imaging of the systemic delivery of small interfering RNA", Wiley Interdiscip Rev Nanomed Nanobiotechnol 494) 428-437 (2012).

Iorio et al., "MicroRNA dysregulation in cancer: diagnostics, monitoring and therapeutics. A comprehensive review", EMBO Mol Med 4(3) 143-159 (2012).

Jiang et al., "MicroRNA-155 functions as an OncomiR in breast cancer by targeting the suppressor of cytokine signaling 1 gene", Cancer Res 70(8) 3119-3127 (2010).

(56) References Cited

OTHER PUBLICATIONS

Kang et al., "Molecular beacon-based bioimaging of multiple microRNAs during myogenesis", Biomaterials 32(7) 1915-1922 (2011).
Kievit et al., "Chlorotoxin labeled magnetic nanovectors for targeted gene delivery to glioma", ACS Nano 4(8) 4587-4594 (2010).
Kimura et al., "Expression of microRNAs in squamous cell carcinoma of human head and neck and the esophagus: miR-205 and miR-21 are specific markers for HNSCC and ESCC", Oncol Rep 23(6) 1625-1633 (2010).
Kota et al., "Therapeutic microRNA delivery suppresses tumorigenesis in a murine liver cancer model", Cell 137(6) 1005-1017 (2009).
Kumar et al., "Image-guided breast tumor therapy using a small interfering RNA nanodrug", Cancer Res 70(19) 7553-7561 (2010).
Li et al., "Detection of microRNA by fluorescence amplification based on cation-exchange in nanocrystals", Anal Chem 81(23) 9723-9729 (2009).
Li et al., "Development of a low-cost detection method for miRNA microarray", Acta Biochim Biophys Sin (Shanghai) 42(4) 296-301 (2010).
Liu et al., "MicroRNA-21 functions as an oncogenic microRNA in mouse and human lung cancer cells by repressing specific tumor suppressors", J Clin Invest 120(4) 1298-1309 (2010).
Lowery et al., "MicroRNA signatures predict oestrogen receptor, progesterone receptor and HER2/neu recceptor status in breast cancer", Breast Cancer Res 11(3) R27 (2009).
Lu et al., "Imaging individual microRNAs in single mammalian cells in situ", Nucleic Acids Res 37(14) e100 (2009).
Ma et al., "miR-9, a MYC/MYCN-activated microRNA, regulates E-cadherin and cancer metastasis", Nat Cell Biol 12 (3) 247-256 (2010).
Ma et al., "Therapeutic silencing of miR-10b inhibits metastasis in a mouse mammary tumor model", Bat Biotechnol 28(4) 341-347 (2010).
Ma et al., "Tumour invasion and metastasis initiated by microRNA-10b in breast cancer", Nature 449(7163) 682-688 (2007).
Mandir et al., "Rapid determination of RNA accessible sites by surface plasmon resonance detection of hybridization to DNA arrays", Anal Chem 81(21) 8949-8956 (2009).
Manohar et al., "Initial results of in vivo non-invasive cancer imaging in the human breast using near-infrared photoacoustics", Opt Express 15(19) 12277-12285 (2007).
Medarova et al., "Development and application of a dual-purpose nanoparticle platform for delivery and imaging of siRNA in tumors", Methods Mol Biol 555: 1-13 (2009).
Medarova et al., "In vivo imaging of siRNA delivery and silencing in tumors", Nat Med 13(3) 372-377 (2007).
Medarova et al., "In vivo imaging of tumor response to therapy using a dual-modality imaging strategy", Int J Cancer 118(11) 3796-3802 (2006).
Medarova et al., "In vivo multimodal imaging of transplanted pancreatic islets", Nat Protoc 1(1) 429-435 (2006).
Medarova et al., "Multifunctional magnetic nanocarriers for image-tagged SiRNA delivery to intact pancreatic islets", Transplantation 86(9) 1170-1177 (2008).
Yen et al., "Multifunctional Iron Oxide Nanoparticles for Diagnostics, Therapy and Macromolecule Delivery", Theranostics, 3(12): 986-1003 (2013).
Medarova et al., "Multiparametric monitoring of tumor response to chemotherapy by noninvasive imaging", Cancer Res 69(3) 1182-1189 (2009).
Michel et al., "Preoperative breast cancer staging: MR imaging of the axilla with ultrasmall superparamagnetic iron oxide enhancement", Radiology 225(2) 527-536 (2002).
Moore, "Image-guided siRNA and miRNA therapies", Presented (Apr. 2013) International Society for Magnetic Resonance in Medicine. Salt Lake City, Utah, and Feb. (2013) Society of Nuclear Medicine and Molecular Imaging—American Association for Cancer Research, San Diego, CA.

Moore et al., "In vivo targeting of underglycosylated MUC-1 tumor antigen using a multimodal imaging probe", Cancer Res 64(5) 1821-1827 (2004).
Moore et al., "Uptake of dextran-coated monocrystalline iron oxides in tumor cells and macrophages", J Magn Reson Imagin 7(6) 1140-1145 (1997).
Mu et al., "Genetic dissection of the miR-17~92 cluster of microRNAs in Myc-induced B-cell lymphomas", Genes Dev 23(24) 2806-2811 (2009).
Nelson et al., "Microarray-based, high-throughput gene expression profiling of microRNAs", Nat Methods 1(2) 155-161 (2004).
Nicoloso et al. MicroRNAs—the micro steering wheel of tumour metastases, Nat Rev Cancer 9(4) 293-302 (2009).
Nziachristos et al., "Fluorescence molecular tomography resolves protease activity in vivo", Nat Med 8(7) 757-760 (2002).
Nuovo et al., "A methodology for the combined in situ analyses of the precursor and mature forms of microRNAs and correlation with their putative targets", Nat Protoc 4(1) 107-115 (2009).
Poellinger et al., "Near-infrared laser computed tomography of the breast first clinical experience", Arad Radiol 15(12) 1545-1553 (2008).
Pohlman et al., "Electrochemical detection of microRNAs via gap hybridization assay", Anal Chem 82(11) 4434-4440 (2010).
Robb et al. "Specific and potent RNAi in the nucleus of human cells", Nat Struct Mol Biol 12(2) 133-137 (2005).
Rossi et al., "microRNA fingerprinting of CLL patients with chromosome 17p deletion identify a miR-21 score that stratifies early survival", Blood 116(6) 945-952 (2010).
Sempere et al., "Altered MicroRNA expression confined to specific epithelial cell subpopulations in breast cancer", Cancer Res 67(24) 11612-11620 (2007).
Silahtaroglu et al., "Detection of microRNAs in frozen tissue sections by fluorescence in situ hybridization using locked nucleic acid probes and tyramide signal amplification", Nat Protoc 2(10) 2520-2528 (2007).
Soliman et al., "Functional imaging using diffuse optical spectroscopy of neoadjuvant chemotherapy response in women with locally advanced breast cancer", Clin Cancer Res 16(9) 2605-2614 (2010).
Song et al., "In situ hybridization detection of microRNAs", Methods Mol Biol 629: 287-294 (2010).
Song et al., "MicroRNA-21 regulates breast cancer invasion partly by targeting tissue inhibitor of metalloproteinase 3 expression", J Exp Clin Cancer Res 29: 29 (2010).
Takeshita et al., "Systemic delivery of synthetic microRNA-16 inhibits the growth of metastatic prostate tumors via downregulation of multiple cell-cycle genes", Mol Ther 18(1) 181-187 (2010).
Tarbe et al., "Transcriptional profiling of cell lines derived from an orthotopic pancreatic tumor model reveals metastasis-associated genes", Anticancer Res 21(5) 3221-3228 (2001).
Tavazoie et al., "Endogenous human microRNAs that suppress breast cancer metastasis", Nature 451(7175) 147-152 (2008).
Treon et al., "Muc-1 core protein is expressed on multiple myeloma cells and is induced by dexamethasone", Blood 93(4) 1287-1298 (1999).
Valastyan et al., "A Pleiotropically Acting microRNA, miR-31, Inhibits Breast Cancer Metastasis", Cell 137(6) 1032-1046 (2009). Retracted Article.
Valastyan et al., "Concurrent suppression of integrin alpha5, radixin, and RhoA phenocopies the effects of miR-31 on metastasis", Cancer Res 70(12) 5147-5154 (2010). Retracted Article.
Van De Ven et al., "A novel fluorescent imaging agent for diffuse optical tomography of the breast: first clinical experience in patients", Mol Imaging Biol 12(3) 343-348 (2010).
Vidic et al., "MicroRNAs targeting mutant K-ras by electrotransfer inhibit human colorectal adenocarcinoma cell growth in vitro and in vivo", Cancer Gene Ther 17(6) 406-419 (2010).
Wang et al., "Combined small interfering RNA therapy and in vivo magnetic resonance imaging in islet transplantation", Diabetes 60(2) 565-571 (2011).
Wang et al., "Gene networks and microRNAs implicated in aggressive prostate cancer", Cancer Res 69(24) 9490-9497 (2009).
Wu et al. "Suppression of cell growth and invasion by miR-205 in breast cancer", Cell Res 19(4) 439-448 (2009).

(56) References Cited

OTHER PUBLICATIONS

Xu et al., "Ultrahighly sensitive homogeneous detection of DNA and microRNA by using single-silver-nanoparticle counting", Chemistry 16(3) 1010-1016 (2010). Retracted Article.
Yan et al., "MicroRNA miR-21 overexpression in human breast cancer is associated with advanced clinical stage, lymph node metastasis and patient poor prognosis", RNA 14(11) 2348-2360 (2008).
Yigit et al., "Context-dependent differences in miR-10b breast oncogenesis can be targeted for the prevention and arrest of lymph node metastasis", Oncogene 32(12) 1530-1538 (2013).
Yigit et al., "Magnetic nanoparticles for cancer diagnosis and therapy", Pharmaceutical Research 29(5):1180-1188 (2012).
Yoo et al., "Detection of miRNA expression in intact cells using activatable sensor oligonucleotides", Chemistry & Biology 21(2):199-204 (2014).
Zhao et al., "microRNA expression profile and identification of miR-29 as a prognostic marker and pathogenetic factor by targeting CDK6 in mantle cell lymphoma", Blood 115(13) 2630-2639 (2010).
Zhou et al., "High-risk myeloma is associated with global elevation of miRNAs and overexpression of EIF2C2/AGO2", Proc Natl Acad Sci USA 107(17) 7904-7909 (2010).
Zhu et al., "MicroRNA-21 targets tumor suppressor genes in invasion and metastasis", Cell Res 18(3) 350-359 (2008).
Xu et al., "Retraction: Ultrahighly sensitive homogeneous detection of DNA and microRNA by using single-silver-nanoparticle counting", Chemistry 16(48):14225 (2010).

\* cited by examiner

| Log2 (RELATIVE EXPRESSION) LN/TUMOR | miRNA |
|---|---|
| 1.9 | let-7a |
| 3.2 | let-7d |
| 1.1 | let-7c |
| 2.5 | let-7i |
| 2.9 | miR-1 |
| 1.2 | miR-100 |
| 2 | miR-10a |
| 2.3 | miR-10b |
| 1 | miR-340 |
| 2.1 | miR-155 |
| 1.3 | miR-15b |
| 1.1 | miR-186 |
| 0.9 | miR-222 |
| -1.3 | miR-182 |
| -1.1 | miR-210 |
| -1 | miR-193b |
| -1.2 | miR-26a |
| -1.6 | miR-27a |
| -1.4 | miR-29a |
| -1.4 | miR-27b |
| -1.4 | miR-200c |
| -1.9 | miR-29c |
| -2.4 | miR-424 |
| -1 | miR-141 |

GROUP 1 VS. CONTROL GROUP

MIRNA PROFILING COMPOSITIONS AND METHODS OF USE

CROSS-REFERENCE TO RELATED APPLICATIONS

This application is a U.S.C. § 371 National Entry Application of International Application No. PCT/US14/18628, which claims benefit under 35 U.S.C. § 119(e) of U.S. Provisional Application No. 61/770,526 filed Feb. 28, 2013, and U.S. Provisional Application No. 61/862,273 filed Aug. 5, 2013, the contents of each of which are incorporated herein by reference in their entireties.

SEQUENCE LISTING

The instant application contains a Sequence Listing which has been submitted electronically in ASCII format and is hereby incorporated by reference in its entirety. Said ASCII copy, created on Feb. 25, 2014, is named 030258-077162-PCT_SL.txt and is 3,374 bytes in size.

FIELD OF THE INVENTION

The present invention relates to the field of imaging diagnostics.

BACKGROUND OF THE INVENTION

The recent literature abounds in examples of the key role played by miRNAs in determining cell fate. Their fundamental importance is particularly well-defined with regard to cancer emergence, progression, and response to therapy (Gabriely, et al., 2011; Hurst, et al., 2009; Iorio and Croce, 2012; Ma, et al., 2007; Nicoloso, et al., 2009).

Non-coding microRNAs represent potentially valuable new biomarkers for breast cancer detection, staging, and therapy assessment. There are several lines of evidence to suggest that 1) miRNAs are upregulated in a wide range of cancers and can act as tumor suppressors or oncogenes[1-6], 2) modulation of miRNA activity has been linked to tumor outcome[7-13], and 3) specific miRNA signatures have been linked to the tissue type, differentiation state and developmental lineage[14-19]. In addition, the combination of standard disease biomarkers with biomarkers derived from non-coding (nc) RNA expression signatures can deliver more comprehensive information about cancer risk assessment and prognosis[20-25]. The development of nanosensors that are capable of noninvasively identifying miRNA signatures characteristic of metastatic cancers such as metastatic breast cancer would have significant value diagnostically. The only reports of in vivo miRNA detection have recently emerged from a group in Korea, which uses molecular beacon technology[37,38]. These latest studies support the feasibility of imaging miRNA availability in vivo. Still, the molecular beacon technology employed in these studies suffers from low signal-to-background ratios, making quantitative interpretation of signal intensity problematic. There is a need for increased sensitivity in the detection. Besides these studies, the currently established methods for microRNA detection in situ rely on PCR and northern blotting, or high-affinity hybridization probes[39-51]. However, these methods are only applicable in vitro. Consequently, these methods do not permit longitudinal studies, in which the "evolution" of the metastatic phenotype is monitored in an intact physiologic environment. Also, such methods, because they rely on hybridization, report on miRNA availability but not on miRNA activity. Further, the existing methods rely on direct hybridization of the sensor oligo to the miRNA, reflecting a 1:1 ratio of fluorescent probe per miRNA, limiting the sensitivity of detection of a small amount in a cell.

SUMMARY OF THE INVENTION

One aspect of the invention relates to a nanosensor for detection of miRNA activity in a target cell. The nanosensor comprises a delivery particle comprising an iron oxide crystal coated with a polymer and a sensor oligonucleotide covalently attached to the polymer. The sensor oligonucleotide comprises a seed region comprising a nucleic acid sequence that is completely complementary to the target miRNA and comprises a cleavage site which can be engaged and cleaved by the target miRNA, two non-seed regions that each flank the seed region and are each comprised of a nucleic acid sequence that is complementary to the target miRNA to promote hybridization of the sensor oligonucleotide to the target miRNA, and members of a quencher-fluorophore pair. The quencher fluorophore pair members respectively flank the cleavage site and are separated by a distance that permits significant quenching of emitted fluorescent signal.

In one embodiment of the compositions and methods described herein, the nanosensor further comprises a targeting ligand covalently attached to the polymer.

In one embodiment of the compositions and methods described herein, the targeting ligand is a peptide specific for an internalizing receptor located on the exterior plasma membrane of the target cell.

In one embodiment of the compositions and methods described herein, the targeting ligand is selected from the group consisting of RGD, folic acid, peptide EPPT (SEQ ID NO: 11), polyarginine peptide (MPAP), and chlorotoxin.

In one embodiment of the compositions and methods described herein, the polymer is selected from the group consisting of polyethylene glycol PEG, dextran, polyvinylpyrrolidone (PVP), fatty acids, polypeptides, chitosan and gelatin, chitosan, polyethylenimine, and combinations thereof.

In one embodiment of the compositions and methods described herein, the iron oxide crystal is from about 20-30 nm in diameter and the polymer is dextran.

In one embodiment of the compositions and methods described herein, the sensor oligonucleotide and/or to the targeting ligand are covalently attached to the polymer by thiol crosslinking.

In one embodiment of the compositions and methods described herein, the polymer is aminated with eipichlorohydrin.

In one embodiment of the compositions and methods described herein, the entire sensor oligonucleotide nucleic acid sequence is completely complementary to the target miRNA sequence.

In one embodiment of the compositions and methods described herein, the sensor oligonucleotide is RNA, or a combination of RNA and one or more other nucleic acid-like polymers that hybridize with RNA in a sequence dependent manner, wherein at least the entire seed region is RNA.

In one embodiment of the compositions and methods described herein, the other nucleic acid-like polymer is DNA, LNA or a 2-0-Me/phosphorothioate backbone.

In one embodiment of the compositions and methods described herein, the sensor oligonucleotide is from about 18 to about 30 nucleotides in length.

In one embodiment of the compositions and methods described herein, the sensor oligonucleotide is about 20-25 nucleotides in length.

In one embodiment of the compositions and methods described herein, the members are separated by a distance of about 9 to about 30 nucleotides.

In one embodiment of the compositions and methods described herein, the fluorophore of the quencher-fluorophore pair is AlexaFluor® 594, AlexaFluor® 647, IRDye®-700DX, AlexaFluor® 750, IRDye®-800, FITC (fluorescein isothiocyanate), Cy3®, or DyLight®594.

In one embodiment of the compositions and methods described herein, the fluorophore of the quencher-fluorophore pair has an emission maximal over 600 nm.

In one embodiment of the compositions and methods described herein, the quencher-fluorophore pair is Iowa Black Hole RQ® quencher and Cy5® fluorophore, or IRDye®-700DX-QC-1. In one embodiment of the compositions and methods described herein, the delivery particle is functionalized with amines to thereby facilitate endosomal swelling and rupture upon cellular uptake.

In one embodiment of the compositions and methods described herein, the target miRNA is one or more of let-7a, let-7d, let-7c, let-7i, miR-1, miR-100, miR-10a, miR-10b, miR-340, miR-155, miR-15b, miR-186, miR-222, miR-182, miR-210, miR-193b, miR-26a, miR-27a, miR-29a, miR-27b, miR-200c, miR-29c, miR-424, and miR-141.

In one embodiment of the compositions and methods described herein, the delivery particle is covalently attached to the sensor oligonucleotide at a ratio selected from the group consisting of about 1:10, about 1:20, about 1:30, about 1:40, and about 1:50.

In one embodiment of the compositions and methods described herein, the delivery particle is covalently attached to the targeting ligand at a ratio of from about 1:1 to about 1:20.

Another aspect of the invention relates to a method for assessing the activity of one or more target miRNA in a target cell. The method involves delivering an effective amount of one or more nanosensors described herein, to the target cell, detecting fluorescence emitted from the one or more nanosensors, and comparing the fluorescence detected with that of a normal control cell to thereby assess if the expression and/or activity of the target miRNA(s) is high, low or normal in the target cell.

Another aspect of the invention relates to a method for in vivo profiling of miRNA(s) of one or more target cells in a subject. The method involves administering to the subject an effective amount of one or more nanosensors described herein, to thereby contact the nanosensors to the target cell(s), quantitatively detecting in the subject fluorescence emitted from the nanosensors in the target cell(s) to thereby determine the expression and/or activity of target miRNAs in the target cells of the subject, and generating a profile from the expression and/or activity of each target miRNA in each target cell or population thereof from the expression and/or activity that is determined.

In one embodiment, the methods described herein further comprise determining and recording the location of the target cell within the subject based on the location of the nanosensor and/or the location of the emitted fluorescence by performing nuclear magnetic resonance (NMR) imaging and/or optical imaging.

In one embodiment, the methods described herein further comprises comparing the fluorescence detected for each target miRNA with that of normal control cells to thereby generate a profile of each target miRNA in the target cell or population thereof as deviated from normal.

In one embodiment of the methods described herein the steps are repeated periodically to thereby monitor progression of the miRNA expression and/or activity in the target cells over time.

In one embodiment of the methods described herein the target cell is in vivo. In one embodiment of the methods described herein the target cell is in vitro.

In one embodiment of the methods described herein the nanosensors are delivered or administered to thereby produce an intracellular concentration in the target cell of about 250 nM.

In one embodiment of the methods described herein the target cell is of a primary tumor, of a metastatic tumor, of a biopsy, virally infected, parasitically infected, or non-infected pathology.

In one embodiment of the methods described herein the one or more miRNA is one or more of miRNAs selected from the group consisting of let-7a, let-7d, let-7c, let-7i, miR-1, miR-100, miR-10a, miR-10b, miR-340, miR-155, miR-15b, miR-186, miR-222, miR-182, miR-210, miR-193b, miR-26a, miR-27a, miR-29a, miR-27b, miR-200c, miR-29c, miR-424, and miR-141.

In one embodiment of the methods described herein the one or more miRNA comprises miR-10b, miR-155, miR-200C, miR-141, or combinations thereof.

In one embodiment of the methods described herein the target cell is in vivo and delivery is by administration to a subject comprising the target cell.

In one embodiment of the methods described herein administration is by injection.

In one embodiment of the methods described herein the dosage is about 5 mg to about 40 mg of iron/kg subject weight.

In one embodiment of the methods described herein the dose is about 10 mg of iron/kg subject weight.

In one embodiment of the methods described herein detecting is by performance of optical imaging.

Another aspect of the invention relates to a method of detecting metastatic or pro-metastatic breast cancer cells in a subject. The method involves assessing the activity of one or more miRNAs of let-7a, let-7d, let-7c, let-7i, miR-1, miR-100, miR-10a, miR-10b, miR-340, miR-155, miR-15b, miR-186, miR-222, miR-182, miR-210, miR-193b, miR-26a, miR-27a, miR-29a, miR-27b, miR-200c, miR-29c, miR-424, and miR-141, in breast cancer cells of the subject. Assessment is administering to the subject an effective amount of one or more nanosensors described herein to thereby contact breast cancer cells of the subject, wherein the nanosensor comprises a sensor oligonucleotide specific for the one or more miRNAs, detecting fluorescence emitted from the one or more nanosensors, comparing the fluorescence detected with that of a control cell to thereby assess the activity of the target miRNA(s) to a cell, and identifying target cells which have high activity compared to a control cell of at least miR-10b and miR155, and have low activity of at least one or more of miR200c, miR-141 and miR-31, as metastatic or pro-metastatic.

In one embodiment of the methods described herein the method further comprises determining and recording the location of the target cell within the subject based on the location of the nanosensor and/or the location of the emitted fluorescence by performing nuclear magnetic resonance (NMR) imaging and/or optical imaging.

In one embodiment of the methods described herein the method further comprises treating the subject aggressively if metastatic or pro-metastatic cells are identified.

Another aspect of the invention relate to a sensor oligonucleotide comprising a seed region comprising a nucleic acid sequence that is completely complementary to the target miRNA and comprises a cleavage site which can be engaged and cleaved by the target miRNA, two non-seed regions that each flank the seed region and are each comprised of a nucleic acid sequence that is complementary to the target miRNA to promote hybridization of the sensor oligonucleotide to the target miRNA, and members of a quencher-fluorophore pair, wherein the quencher fluorophore pair members respectively flank the cleavage site and are separated by a distance that permits significant quenching of emitted fluorescent signal.

In one embodiment of the herein described compositions, the sensor oligonucleotide has a nucleic acid sequence that is completely complementary to the target miRNA sequence.

In one embodiment of the herein described compositions, the sensor oligonucleotide comprises RNA, or a combination of RNA and one or more other nucleic acid-like polymers that hybridize with RNA in a sequence dependent manner, wherein at least the entire seed region is RNA.

In one embodiment of the herein described compositions, the other nucleic acid-like polymer is DNA, LNA or a 2-0-Me/phosphorothioate backbone.

In one embodiment of the herein described compositions, the sensor oligonucleotide is from about 18 to about 30 nucleotides in length.

In one embodiment of the herein described compositions, the sensor oligonucleotide is about 20-25 nucleotides in length.

In one embodiment of the herein described compositions, the quencher-fluorophore pair members of the sensor oligonucleotide are separated by a distance of about 9 to about 30 nucleotides.

In one embodiment of the herein described compositions, the fluorophore of the quencher-fluorophore pair is selected from the group consisting of AlexaFluor® 594, AlexaFluor® 647, IRDye®-700DX, AlexaFluor® 750, IRDye®-800, FITC, Cy3®, and DyLight®594.

In one embodiment of the herein described compositions, the fluorophore of the quencher-fluorophore pair has an emission maximal over 600 nm.

In one embodiment of the herein described compositions, the quencher-fluorophore pair is Iowa Black Hole RQ® quencher and Cy5® fluorophore, or IRDye®-700DX-QC-1.

In one embodiment of the herein described compositions, the target miRNA is selected from the group consisting of let-7a, let-7d, let-7c, let-7i, miR-1, miR-100, miR-10a, miR-10b, miR-340, miR-155, miR-15b, miR-186, miR-222, miR-182, miR-210, miR-193b, miR-26a, miR-27a, miR-29a, miR-27b, miR-200c, miR-29c, miR-424, and miR-141.

In one embodiment of the herein described compositions, the sensor oligonucleotide further comprises a targeting ligand covalently attached to the polymer. In one embodiment, the targeting ligand is a peptide specific for an internalizing receptor located on the exterior plasma membrane of the target cell. In one embodiment, the targeting ligand is selected from the group consisting of RGD, folic acid, peptide EPPT (SEQ ID NO: 11), polyarginine peptide (MPAP), and chlorotoxin.

Another aspect of the invention relates to a method for in vivo profiling of miRNA(s) of one or more target cells in a subject comprising, delivering to the target cell(s) an effective amount of one or more sensor oligonucleotides described herein, quantitatively detecting in the subject fluorescence emitted from the sensor oligonucleotides in the target cell(s) to thereby determine the activity of target miRNAs in the target cells of the subject, and generating a profile from the activity of each target miRNA in each target cell or population thereof from the activity determined.

Another aspect of the invention relates to a method for assessing the activity of one or more target miRNA in a target cell comprising, delivering to the target cell an effective amount of one or more sensor oligonucleotides described herein, detecting fluorescence emitted from the one or more sensor oligonucleotides, and comparing the fluorescence detected with that of a normal control cell to thereby assess if the activity of the target miRNA(s) is high, low or normal in the target cell.

In one embodiment of the herein described methods, the method further comprises comparing the fluorescence detected for each target miRNA with that of normal control cells to thereby generate a profile of each target miRNA in the target cell or population thereof as deviated from normal.

In one embodiment of the herein described methods, the steps are repeated periodically to thereby monitor progression of the miRNA activity in the target cells over time.

In one embodiment of the herein described methods, the target cell is in vivo.

In one embodiment of the herein described methods, the target cell is in vitro.

In one embodiment of the herein described methods, the sensor oligonucleotides are delivered or administered to thereby produce an intracellular concentration in the target cell of about 250 nM.

In one embodiment of the herein described methods, the target cell is of a primary tumor, of a metastatic tumor, of a biopsy, virally infected, parasitically infected, or non-infected pathology.

In one embodiment of the herein described methods, the or more miRNA is one or more of miRNAs selected from the group consisting of let-7a, let-7d, let-7c, let-7i, miR-1, miR-100, miR-10a, miR-10b, miR-340, miR-155, miR-15b, miR-186, miR-222, miR-182, miR-210, miR-193b, miR-26a, miR-27a, miR-29a, miR-27b, miR-200c, miR-29c, miR-424, and miR-141.

In one embodiment of the herein described methods, the one or more miRNA comprises miR-10b, miR-155, miR-200C, miR-141, or combinations thereof.

In one embodiment of the herein described methods, the target cell is in vivo and delivery is by administration to a subject comprising the target cell.

In one embodiment of the herein described methods, administration is by injection.

In one embodiment of the herein described methods, delivering or administering is by intratumoral injection, transfection, or titration/incubation.

Another aspect of the invention relates to a method of detecting metastatic or pro-metastatic breast cancer cells in a subject comprising, assessing the activity of one or more miRNAs selected from the group consisting of let-7a, let-7d, let-7c, let-7i, miR-1, miR-100, miR-10a, miR-10b, miR-340, miR-155, miR-15b, miR-186, miR-222, miR-182, miR-210, miR-193b, miR-26a, miR-27a, miR-29a, miR-27b, miR-200c, miR-29c, miR-424, and miR-141, in breast cancer cells of the subject by administering to the subject an effective amount of one or more sensor oligonucleotides described herein, to thereby contact breast cancer cells of the subject, wherein the sensor oligonucleotide is specific for the one or more miRNAs, detecting fluorescence emitted from the one or more sensor oligonucleotides, comparing the fluorescence detected with that of a control cell to thereby assess the activity of the target miRNA(s) to a cell, and identifying target cells which have high activity compared to a control cell of at least miR-10b and miR155, and have low activity of at least one or more of miR200c, miR-141 and miR-31, as metastatic or pro-metastatic.

In one embodiment of the herein described methods, administration is by intratumoral injection.

In one embodiment of the herein described methods, the method further comprises determining and recording the location of the target cell within the subject based on the location of the emitted fluorescence by performing optical imaging.

In one embodiment of the herein described methods, the method further comprises treating the subject aggressively if metastatic or pro-metastatic cells are identified.

Definitions

The term "diamagnetic" is used to describe a composition that has a relative magnetic permeability that is less than or equal to 1 and that is repelled by a magnetic field.

The term "paramagnetic" is used to describe a composition that develops a magnetic moment only in the presence of an externally-applied magnetic field.

The term "ferromagnetic" or "ferromagnetic" is used to describe a composition that is strongly susceptible to magnetic fields and is capable of retaining magnetic properties (a magnetic moment) after an externally-applied magnetic field has been removed.

The term "fluorophore" refers to a molecule that absorbs light at a first wavelength and emits light at a second wavelength, where the first wavelength is shorter (higher energy) than the second wavelength. In some embodiments, the first wavelength absorbed by the fluorophore can be in the near-infrared range. Non-limiting examples of fluorophores are described herein. Additional examples of fluorophores are known in the art.

As used herein, the term "cell" is meant to refer to a single cell or a population of such cells. A population of cells can be in vitro or in vivo. A population of cells refers to cells that have one or more common characteristics such as origin, location in the body, tissue type, etc. For example, a population of tumor cells would have similar characteristics. In one embodiment, a population of cells is a specific tissue within the body. In one embodiment, a population of cells is a tumor tissue. In one embodiment, a population of cells are cells which demonstrate a particular pathology (e.g., cancer, or infection by a pathogen). It is recognized that a population of cells may be homogeneous (e.g., the cells are all clonal) or may be heterogeneous in that they may share many commonalties (e.g. receptors, surface markers, location within the body) but have some differences (e.g., genotypic or phenotypic) between them such as those brought about by a developing pathology.

By the term "nucleic acid" is meant any polynucleotide (e.g., DNA or RNA, of natural or semi-synthetic, or synthetic origin). The term nucleic acid includes oligonucleotides containing at least one modified nucleotide (e.g., containing a modification in the base and/or a modification in the sugar) and/or a modification in the phosphodiester bond linking two nucleotides. In some embodiments, the nucleic acid can contain at least one locked nucleotide (LNA). Non-limiting examples of nucleic acids are described herein. Additional examples of nucleic acids are known in the art.

A nucleic acid can be either DNA or RNA. The DNA or RNA can further contain one or more modified nucleotides. By the term "modified nucleotide" is meant a DNA or RNA nucleotide that contains at least one modification in its base and/or at least one modification in its sugar (ribose or deoxyribose). A modified nucleotide can also contain modification in an atom that forms a phosphodiester bond between two adjoining nucleotides in a nucleic acid sequence.

An "effective amount", as used herein, refers to an amount that is sufficient to produce statistically significant, reproducible results. In one embodiment, an effective amount of a nanosensor is an intracellular concentration of about 250 nm.

BRIEF DESCRIPTION OF THE DRAWINGS

(FIG. 3A) The probe consists of dextran-coated magnetic nanoparticles, conjugated to Cy5.5 dye, a tumor-targeting peptide (RGD) and an antisense oligonucleotide for inhibition of miRNA-10b. (FIG. 3B) Flow cytometry of MDA-MB-231 human breast cancer cells, following a 48-hr incubation with MN-anti-miR10b. (FIG. 3C) Confocal microscopy of MDA-MB-231(gfp) human breast cancer cells (visualized as green), following a 48-hr incubation with MN-anti-miR10b, showing the distribution of MN (Cy5.5, visualized as blue) and oligo (visualized as red). (FIG. 3D) qRT-PCR for levels of miRNA-10b expression, following a 48-hr incubation with MN-anti-miR10b.

(FIG. 4A) T2 weighted images and color-coded T2 maps pre and 24-hrs post-injection of the nanoparticles. The tumor is outlined.; (FIG. 4B) T2 (pre-contrast and T2 post-contrast) relaxation times of the tumor.

(FIG. 5A) In vivo imaging of mice before (left) and 24 hours after (right) MN-anti-miR10b administration. Arrows point to lymph nodes. Corresponding bioluminescence image (whole-body and with the tumor masked, inset). The animal was repositioned after injection of luciferin). (FIG. 5B) Ex vivo images of excised tissues (PT, primary tumor; BLNs, brachial lymph nodes; ILN, inguinal lymph nodes; CLNs, cervical lymph nodes). (FIG. 5C) Quantitative analysis of the ex vivo optical images. Muscle tissue was used as a reference ($p \leq 0.0001$). Data are represented as mean±SD. (FIG. 5D) Histology of frozen tumor sections. The nanoparticles were visualized as red (Cy5.5), and the nuclei were visualized as blue (DAPI). (FIG. 5E) Histology of frozen lymph node sections from mice injected with MN-scr-miR (inactive drug that permits the formation of lymph node metastases). The nanoparticles were visualized as red (Cy5.5), the nuclei visualized as blue (DAPI), and the microphages were visualized as green (CD68). H&E: hematoxylin and eosin staining.

(FIG. 6A) Representative bioluminescence images. (FIG. 6B) Quantitative analysis of bioluminescence images. (FIG. 6C) Radiance (photons/sec) in the primary tumors of experimental and control mice indicating no difference in tumor size between the two groups. Data are represented as mean±SEM. (FIG. 6D) H&E staining of frozen lymph node sections from animals treated with MN-anti-miR10b (right) or MN-scr-miR (left). In the control animals, there was extensive tumor cell infiltration (arrowheads) outside of reverse follicles (arrows). In animals treated with MN-anti-miR10b, lymph nodes had normal tissue architecture. (FIG. 6E) Relative expression by qRT-PCR of miR-10b. (FIG. 6F) Induction of the HOXD10 in experimental tumors, shown by Western blotting.

(FIG. 8A) Fluorescence imaging in a cell-free system. Two different scales are shown for sensor oligo concentrations above and below 10 nM, to avoid signal saturation at the higher concentrations when optimal resolution is achieved at the lower concentrations. However, this is a single-shot experiment. (FIG. 8B) Quantification of radiant efficiency from A. (FIG. 8C) Gel electrophoresis after ethidium bromide staining confirming cleavage of the sensor oligo (i.e. there is no detectable band corresponding to intact oligo in the treatment group. In the control group, in which miR-10b is inhibited by antisense oligonucleotides, there is no cleavage of the sensor oligo and the band is preserved).

(FIG. 9A) Epifluorescence optical imaging (Ivis Spectrum). (FIG. 9B) Representative images using epifluorescence optical imaging. (FIG. 9C) Fluorescence microscopy of intact cells. (FIG. 9D) Flow cytometry of intact cells. (FIG. 9E) Quantitative comparison of epifluorescence imaging, flow cytometry, and the gold-standard RT-PCR.

(FIG. 11A) Fluorescence optical imaging. (FIG. 11B) Quantification of radiant efficiency from A. (FIG. 11C) qRT-PCR of miR-10b expression.

(FIG. 12A) The sensor oligonucleotides are composed of RNA bases, are cleavable (non-stabilized by chemical modification) around the seed region, and are labeled with a fluorescent dye-quencher pair, so that upon cleavage of the oligonucleotide by the micro-RNA-RISC, fluorescence enhancement is observed. (FIG. 12B) Upon internalization of the sensor oligos by the cell, the sensors form base pair with their miRNA targets (FIG. 12BI). This binding event leads to the recruitment to the duplex of the endogenous RNA induced silencing complex (RISC) and cleavage of the oligo at a specific position in the seed region (FIG. 12BII). This cleavage results in separation between the quencher and dye located at the ends of the sensor oligo, and fluorescence turn-on. The microRNA is released from the complex and is free to catalyze subsequent cleavage reactions (FIG. 12BIII).

(FIG. 13A) Epifluorescence imaging. Two different scales are shown for sensor oligo concentrations above and below 10 nM, to avoid signal saturation at the higher concentrations when optimal resolution is achieved at the lower concentrations. (FIG. 13B) Quantification of radiant efficiency from FIG. 14A. The results indicated a detection limit of 13.4 nM. (FIG. 13C) Gel electrophoresis followed by ethidium bromide staining confirmed cleavage of the sensor oligo (i.e. there is no detectable band corresponding to intact sensor oligo in the treatment group. In the control group, in which miR-10b is inhibited by antisense oligonucleotides, there is no cleavage of the sensor oligo and the band is preserved).

(FIG. 14A) Radiant efficiency as a function of sensor concentration from epifluorescence optical imaging. (FIG. 14B) Time course of sensor activation. Representative images at 3, 16, 24, and 48 hours of incubation. (FIG. 14C) Quantitative analysis of images shown in FIG. 15B. (FIG. 14D) Fluorescence microscopy of intact cells. (FIG. 14E) Flow cytometry of intact cells. (FIG. 14F) Quantitative analysis of epifluorescence imaging, flow cytometry, and the gold-standard real-time qRT-PCR at a sensor concentration of 250 nM.

DETAILED DESCRIPTION OF THE INVENTION

Figure 1A:
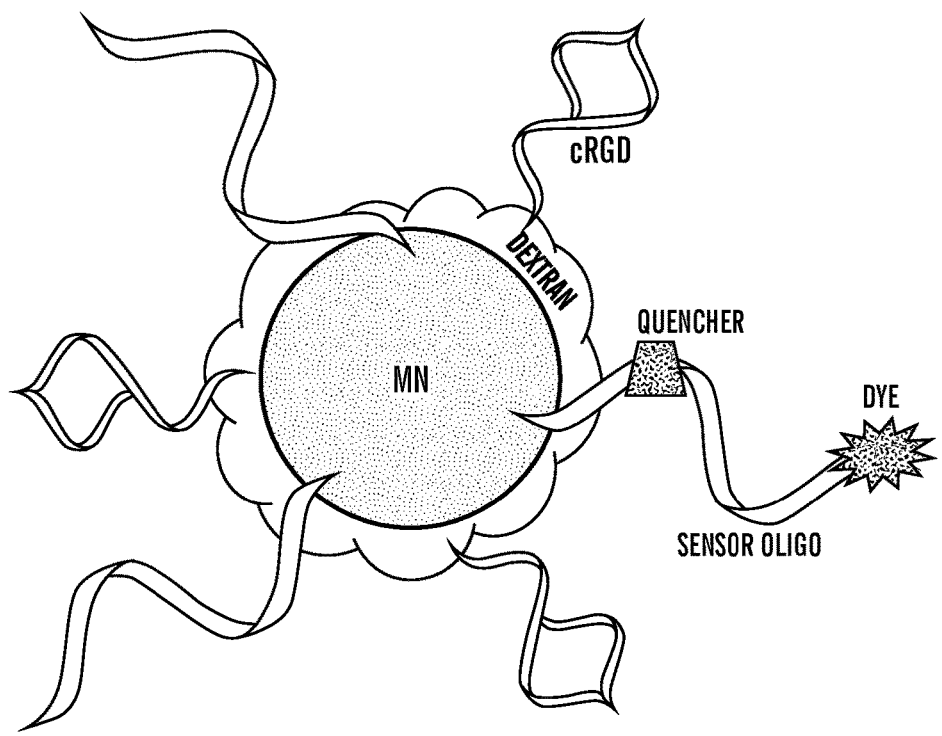
FIG. 1A-FIG. 1B is a diagram that shows the nanosensor design (FIG. 1A) and mechanism of action (FIG. 1B).

Aspects of the present invention arise from the development of an miRNA sensor that detects the amount of expression of a specific miRNA in a sample (e.g., a cell or population thereof). The sensor is highly sensitive and specific for the miRNA targeted for detection (target miRNA). The sensor, referred to herein as the "sensor oligonucleotide" or "sensor oligo", can be delivered to a cell, in vivo or in vitro, for quantitative detection of a specific miRNA present in that cell. Examples of delivery methods are described herein. A plurality of different sensor oligonucleotides can be delivered at once to a cell to measure the expression of a plurality of different miRNAs in the cell. A profile reflective of expression of the miRNAs in the cell can be generated from the collected information. Such profiling of miRNA expression can be used to identify normal versus disease associated miRNA signatures, which, once determined, can be used for diagnostics.

The sensor oligonucleotide can be attached to a solid substrate, to facilitate delivery and/or detection of the sensor oligo. Nanoparticles that are commonly used in noninvasive imaging (e.g., a magnetic nanoparticle) are particularly relevant for use in the compositions described herein. The attached substrate (e.g., nanoparticle) facilitates in vivo delivery and also identification and tracking of the sensor oligonucleotide. The combined sensor oligonucleotide and substrate (e.g., nanoparticle), are referred to herein as a "nanosensor". The nanosensor can be used for noninvasive, sensitive and targeted detection of specific miRNA activity in a live target cell in the context of a whole organism. This powerful technique of detecting miRNA activity in an in vivo cell population can be performed with >95% specificity and nanomolar sensitivity. Assays which utilize these nanosensors are simple, inexpensive ($40/L of assay solution), and amenable to a rapid (about 2 hrs for 96 samples) assay format.

Recent findings indicate that changes in miRNA activity are associated with specific pathologies such as cancer. Identification of such deviations in the miRNA profile of a cell can provide important diagnostic information. The nanosensor described herein can be used to non-invasively determine the miRNA signature of a selected cell population of a patient and provide critical diagnostic information. The nanosensors can also be used to monitor the progression of miRNA expression over time in diseased tissue to monitor disease progression and/or recovery or remission. Such powerful information will allow medical practitioners to develop effective individualized treatment plans for each patient throughout the course of therapy.

One aspect of the invention relates to the sensor oligonucleotide, which can be used for detection of miRNA activity in a target cell. The sensor oligonucleotide is designed to bind the target miRNA such that binding leads to the recruitment to the duplex of the endogenous RNA induced silencing complex (RISC), to produce cleavage of the oligo at a specific position within the seed region. That cleavage results in the emission of a detectable signal. The miRNA present in the cell(s) which received the sensor oligonucleotide (recipient target cells) can be quantitated from the amount of signal that is emitted. The sensor oligonucleotide can be used in the methods described herein to detect miRNA activity. The sensor oligonucleotide is useful in various contexts for use in these methods. The sensor oligonucleotide can be used independently (e.g., not in the context of a nanosensor), or in the context of a larger composition (e.g., linked to a nanoparticle such as in the context of a nanosensor). Furthermore, the sensor oligonucleotide can be in the context of a larger complex (e.g. that lacks a nanoparticle).

Another aspect of the invention relates to the sensor oligonucleotide in the context of a nanosensor, and its use for detection of miRNA activity in a target cell. The nanosensor comprises one or more sensor oligonucleotides that are specific for a miRNA. The sensor oligonucleotide(s) is covalently attached to a nanoparticle, also referred to as a "delivery particle". The nanoparticle/delivery particle component of the nanosensor can be made from a variety of materials, described further herein. As above, the sensor oligonucleotide is designed to bind the target miRNA such that binding leads to the recruitment to the duplex of the endogenous RNA induced silencing complex (RISC), to produce cleavage of the oligo at a specific position within the seed region. That cleavage results in the emission of a detectable signal. The miRNA present in the cell(s) which received the nanosensor (recipient target cells) can be quantitated from the amount of signal that is emitted.

The sensor oligonucleotide is a contiguous, non-branched oligonucleotide with a sequence specifically designed to detect a particular miRNA of interest. The sensor oligonucleotide is made up of different regions determined by their nucleic acid sequence. The sensor oligo has a central seed region which has a nucleic acid sequence that is completely complementary to the target miRNA. The seed region also contains a cleavage site which is cleaved by RISC upon appropriate engagement with the miRNA. The length of the seed region can vary, but is typically from about 5 to about 12 nucleotides. In one embodiment, the seed region is from about 6 to about 9 nucleotides in length. In one embodiment, the seed region is 7 nucleotides, or 8 nucleotides in length. The skilled practitioner will determine the nucleic acid sequence and positioning of the seed region within the sensor oligo for each specific target miRNA. In one embodiment, the seed region is designed so that it hybridizes to the miRNA at about 2-5 nucleotides from the 5' end of the target miRNA.

The seed region is central to the other regions of the sensor oligo. It is flanked on each end by two non-seed regions. The two non-seed regions each have a nucleic acid sequence that is sufficiently complementary to the target miRNA (e.g., completely complementary, or contains some non-complementary bases) to promote hybridization of the sensor oligo to the target miRNA. Mismatches outside of the seed region are to some degree tolerable (e.g., 1, 2 or 3 base mis-matches in one or both non-seed regions). For convenience, these two non-seed regions can be referred to by their location with respect to the seed region. The 5' non-seed region is located 5' to the seed region, and the 3' non-seed region is located 3' to the non-seed region. Their length and sequence promotes hybridization of the sensor oligonucleotide to the target miRNA. In one embodiment, one non-seed region is completely complementary to the target miRNA. In one embodiment, both non-seed regions are completely complementary to the target miRNA.

The length of the sensor oligo can be determined by the skilled practitioner and will depend upon a variety of factors including the target miRNA, the fluorophore indicators, and nucleotide components. In one embodiment, the sensor oligo is at least about 15 nucleotides in length (e.g., 15, 16, 17, 18, 19, etc.). Smaller lengths may also be useful (e.g., 11, 12, 13 or 14 nt). In one embodiment, the sensor oligo is at least 20 nucleotides in length. In one embodiment, the sensor oligo is from about 20 to about 25 nucleotides in length (e.g., 20, 21, 22, 23 or 25 nt). Longer lengths may also be useful (e.g., 26, 27, 28, 29 or more). In one embodiment, the sensor oligo is from about 18 to 30 nucleotides in length (e.g., 19, 20, 21 . . . or 30 nt). Lengths of between 30 and 50 nucleotides may also be of use in specific circumstances.

The nucleotide content of the sensor oligo can be determined by the skilled practitioner depending upon the specific needs of the analysis. The seed region is necessarily composed of nucleotides that allow cleavage of the oligo. Typically, the seed region is RNA, although modifications of the RNA that allow cleavage of the oligo are also envisioned. The non-seed regions can be comprised of RNA, DNA, or modified nucleotides (e.g., those described herein).

The sensor oligonucleotide further contains both members of a quencher-fluorophore pair. Examples of quencher-fluorophore pairs are described herein. The quencher-fluorophore pair members are located outside of the seed region, respectively flanking the cleavage site. The quencher-fluorophore pair members can be conveniently referred to by their location with respect to the seed region, or by their location within the respective non-seed region. In one embodiment, the fluorophore and the quencher are located on respective ends of the sensor oligo (either one being on the 3' or the 5' end). In one embodiment, the fluorophore is internal and the quencher is on the 5' end of the oligonucleotide. In one embodiment, the quencher is internal and the fluorophore is on the 5' end of the oligonucleotide. In one embodiment, both the quencher and the fluorophore are internal.

The quencher-fluorophore pair members are separated from each other by the intervening oligonucleotide. The distance by which they are separated is such that significant quenching of emitted fluorescent signal occurs. The optimal distance of separation of the quencher-fluorophore pair members can vary with respect to the specific dye/quenchers used. In one embodiment, the quencher-fluorophore pair members are separated by a distance of about 9 to about 30 nucleotides. In one embodiment, the pair members are separated by about 10 nucleotides (about 3.4 nm). In one embodiment, the members are separated by about 9 to about 15 nucleotides (e.g., 9, 10, 11, 12, 13, 14, 15). In one embodiment the pair members are separated by about 16, 17, 18, 19, or about 20 nucleotides. In one embodiment, the pair members are separated by about 20 to about 30 nucleotides (e.g., 20, 21, 22, 23, 24, 25, 26, 27, 28, 29 or 30). In one embodiment, the pair members are separated by less than about 30 nucleotides.

Cleavage of the seed region results in separation of the quencher and dye and leads to the emission of a fluorescent signal. The fluorescent signal that is emitted is a direct indication of the presence of the target miRNA in the cell. Detection of the fluorescent signal can be performed to determine the amount (quantitative or semi-quantitative) of the target miRNA in the cell.

The skilled practitioner will appreciate that other possible sensor oligonucleotide and/or nanosensor designs will result in a detectable signal upon cleavage of the seed region. Such designs are also encompassed in the invention. For example, the sensor oligonucleotide that is in the context of a nanosensor can be attached at one end to a second nanoparticle (e.g., magnetic). Separation of the two magnetic nanoparticles upon cleavage results in a reduction in R2 relaxivity. Such magnetic relaxation switching (MRS) is known in the art and can be detected and quantitated by the skilled practitioner.

The nanosensor may optionally further comprise a targeting ligand which facilitates delivery of the nanosensor to a target cell. The targeting ligand can be covalently linked to the nanoparticle (e.g., by way or linkage to a polymer coating on the nanoparticle). A targeting ligand can also be linked more directly to a sensor oligonucleotide (e.g., in the absence of a nanoparticle) to facilitate delivery of the sensor oligonucleotide to a target cell. Examples of targeting ligands include, without limitation, RGD, folic acid, peptide EPPT (SEQ ID NO: 11) (Kumar et al., Cancer Research 2010; 70:7553-7561), polyarginine peptide (MPAP), and chlorotoxin (Kievit et al., ACS Nano. 2010; 4:4587-94). Peptide EPPT (SEQ ID NO: 11) is used to target tumor-specific underglycosylated mucin-1 antigen (Umuc-1). MPAP is an arginine rich cationic peptide that facilitates nanoparticle uptake by electronstatic interaction between the positively charged peptide and the negatively charged cell membrane. In one embodiment, the targeting ligand is a member of a specific binding pair, wherein the other member of the specific binding pair is present on the target cell. Examples of specific binding pairs are known in the art, such as biotin/avidin, antibody binding fragments/antigen, and receptor/ligand. In one embodiment, the targeting ligand is a peptide specific for an internalizing receptor located on the exterior plasma membrane of the target cell. Such targeting peptides are known and commonly used to deliver an agent to a specific cell type or tissue. By the term "targeting peptide" is meant a peptide that is bound by a molecule (e.g., protein, sugar, or lipid, or combination thereof) present in or on the plasma membrane of a target cell (e.g., a cancer cell). As described herein, a targeting peptide can be covalently linked to a secondary molecule or composition (e.g., nanoparticles described herein) to target the secondary molecule or composition to a target cell (e.g., a cancer cell). In some embodiments, a targeting peptide that is covalently linked to a secondary molecule or composition results in the uptake of the secondary molecule or composition by the targeted cell (e.g., cellular uptake by endocytosis or pinocytosis).

Linkage of one or more of the components of the nanosensor (e.g., sensor oligo, targeting ligand) to the delivery particle can be by covalent linkage (e.g., to a polymer coating of the particle). A variety of methods of linkage are known in the art, examples of which are described herein.

The optimal stoichiometry of the delivery particle to the attached components can be determined by the skilled practitioner. In one embodiment, the delivery particle is attached to the sensor oligo at a ratio of about from about 1:10 to about 1:50. In one embodiment, the delivery particle: sensor oligo ratio is 1:5, 1:10, 1:15, 1:20, 1:25; 1:30, 1:35; 1:40, 1:45, or about 1:50. In one embodiment the delivery particle has at least 40 sensor oligos per particle.

A plurality of sensor oligos can be used in the methods described herein to determine the miRNA profile for a plurality of miRNAs in a cell. When a plurality of sensor oligos are used in the method described herein, it is envisioned that each sensor oligo will have incorporated within a unique detection system (e.g., a unique fluorophore pair that emits a signal that can be distinguished from the signal emitted by the accompanying sensor oligo(s)). Specific determination of combinations of detection systems can be performed by the skilled practitioner. The different sensor oligos can be used on their own, or in the context of a nanosensor. One or more of the sensor oligos can be attached to different delivery particles, or a delivery particle can be linked to a plurality of sensor oligos for the detection of multiple miRNA. Multiple nanosensors (e.g., with one or more sensor oligos) and/or sensor oligos can also be delivered as well, to detect multiple miRNAs.

The delivery particle can also be attached to one or more targeting ligands. In one embodiment, the ratio of delivery particle to targeting ligand is from about 1:1 to about 1:50. In one embodiment, the ratio is from about 1:1 to about 1:40. In one embodiment, the ratio is from about 1:1 to about 1:30. In one embodiment, the ratio is from about 1:1 to about 1:20. In one embodiment, the ratio is about 1:10, 1:20, 1:30, 1:40 or about 1:50.

The sensor oligos (e.g., in the context of a nanosensor) described herein can be used in vivo to non-invasively determine miRNA signatures in recipient cells. When repeatedly used for specific target cells they can be used to monitor the progression of the miRNA activity in the target cells over time. Recent findings indicate that specific pathological states are associated with specific miRNA signatures. As such, identification of an miRNA signature associated with a specific pathology or state can provide important diagnostic information.

One aspect of the invention relates to a method for assessing the activity of one or more target miRNA in a target cell. The method involves contacting an effective amount of one or more nanosensors described herein to the target cell under conditions appropriate for uptake of the nanosensor by the target cell. The nanosensors are specific for the miRNA(s) of interest by way of the sensor oligo attached thereto. Signal (e.g., fluorescense) emitted from the one or more nanosensors is then detected and used to determine the amount of the target miRNA in the cell. Either specific amounts or relative amounts can be determined by comparison to results obtained by the same method performed with an appropriate control. The determination of whether the miRNA activity is high, low or normal compared to a normal control cell is made by identifying statistically significant, reproducible results that indicate a higher level of activity, or a lower level of activity, or no significant difference, respectively, in comparison to the normal control. The sensor oligo, in the absence of a delivery particle, can alternatively or in combination, be delivered into the target cell/tissue for use in this method, to assess the activity of one or more target miRNAs therein.

This method can be used to assess the activity of selected miRNA in a specific population of cells suspected of, or having, a known pathology or stage or pathology. Results identified for each miRNA can be used to correlate relevant differences in miRNA activity that are significantly associated with the pathology. In this way, an miRNA signature that is associated with a specific pathology or stage of the pathology can be obtained. Such information can be used in diagnosis of the pathology, and also in monitoring treatment effectiveness. The methods described herein can further be applied to diagnosis of a subject by way of identifying an miRNA signature in a cell population in that individual that is known to be associated with a specific pathology (e.g., cancer).

The skilled practitioner is able to identify relevant differences (e.g., increase or decrease) in expression/activity of an assessed miRNA. A statistically significant, reproducible result is indicative of a relevant difference in miRNA expression/activity. In one embodiment, the increase or decrease in miRNA activity/expression is at least 2× that of an appropriate control cell. In one embodiment, the increase or decrease is at least 3×, 4×, or 5× that of an appropriate control cell. In one embodiment, the increase or decrease is at least 10×, 20×, 30×, 40×, or 50× that of a control cell. In one embodiment, the increase or decrease is at least 100×, 120×, 130×, 140×, 150×, 160×, 170×, 180×, 190× or 200× that of a control cell. Larger fold increases or decreases may also be observed (e.g., 300× or 400×).

The appropriate control cell is determined by the skilled practitioner for the particular cell or pathology under examination. In one embodiment, an appropriate control cell is a cell of the same tissue type that has a normal, healthy phenotype and/or genotype. In one embodiment, the control cell is found in the same tissue as the target cell. In one embodiment, an appropriate control is a cell that exhibits the same pathology, but is located in a different location in the body of a subject. Control cells can also be used to generate pre-established reference numbers for use in comparison to ongoing assays.

The target cell may be in vitro or in vivo. When performed in vivo or in vitro, a sensor oligo in the absence of a delivery particle can also be used, with uptake by the cell accomplished by normal DNA delivery procedures common in the art. Delivery of the nanosensor can be performed, for example, by contacting the target cells with the nanosensors. Such contact can occur under in vivo or in vitro culture conditions. In vitro culture conditions may involve titration and incubation of the cells in culture. For example a solution of the nanosensor is added (e.g., 24-400 µg/ml of iron) to cells growing as a monolayer or in suspension in culture media. Following the addition, the cells are cultured for a given time period (typically 2-72 hours) to allow for uptake of the nanosensor. This method of delivery is demonstrated in WO 2013/016126, the contents of which are incorporated herein by reference. The cells can be washed prior to examination for nanosensor based assessment of miRNA activity (e.g., by fluorescence based methods). In vivo, delivery of the sensor oligo in the absence of a delivery nanoparticle to target tissue can be achieved by direct nucleic acid delivery techniques known in the art such as injection into the tissue (e.g., intratumoral injection) or by delivery with a transfection agent.

Nucleic acid delivery techniques are well known to those of skill in the art and include, but are not limited to, the use of calcium phosphate, liposomes such as lipofectamine, electroporation, and plasmids and vectors including viral vectors. Suitable methods for nucleic acid delivery to a target cell or population include any method by which a nucleic can be introduced into an organelle, a cell, a tissue or an organism, as described herein or as would be known to one of ordinary skill in the art. Such methods include, but are not limited to, direct delivery of DNA such as by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harlan and Weintraub, 1985; U.S. Pat. No. 5,789,215, incorporated herein by reference); by electroporation (U.S. Pat. No. 5,384,253, incorporated herein by reference); by calcium phosphate precipitation; by using DEAE-dextran followed by polyethylene glycol; by direct sonic loading; by liposome mediated transfection; by microprojectile bombardment (PCT Application Nos. WO 94/09699 and 95/06128; U.S. Pat. Nos. 5,610,042; 5,322,783 5,563,055, 5,550,318, 5,538,877 and 5,538,880, each incorporated herein by reference); by agitation with silicon carbide fibers (U.S. Pat. Nos. 5,302,523 and 5,464,765, incorporated herein by reference).

Other in vitro and in vivo methods of delivery of the sensor oligonucleotide or nanosensors include, without limitation, methods known in the art to thereby contact the target cells with an effective amount of the nanosensors. Various routes of in vivo administration are available, examples of which are described herein. The appropriate route of administration and dosage can be determined by the skilled practitioner, and will depend upon various factors including, without limitation, the target cells, the pathology, the nanoparticle composition, the specific detectors (e.g., specific fluorophores) used to identify the presence of the miRNA, and any specific targeting ligands used. In one embodiment, administration is by injection (e.g., intravenous or at the site of pathology). In one embodiment, the dose is about 5 mg to about 40 mg of iron/kg subject weight for an iron oxide based nanoparticle. In one embodiment, the dose is about 10 mg to about 30 mg of iron/kg subject weight for an iron oxide based nanoparticle. In one embodiment, the dose is about 10 mg of iron/kg subject weight for an iron oxide based nanoparticle.

When an miRNA signature is known to be associated with a pathology, that information can be used in diagnosis of the pathology in a subject. The sensor oligo and nanosensor described herein can be used to profile specific miRNAs in the target cells of a subject. Sensor oligos (alone or in the context of a nanosensor) specific for the appropriate target miRNAs are administered to the subject. Following that, the fluorescence emitted from the sensor oligos in the target cells are quantitatively detected in the subject (e.g, by optical imaging of the target cells). A profile of the activity of the target miRNAs is then generated from the information gathered for each miRNA examined in the target cell. In one embodiment, that profile is generated by comparison of the fluorescence detected for each target miRNA as analyzed in the target cells as deviated from that generated in an identically treated normal/control cell. If the profile that is determined for the subject reflects the miRNA signature associated with a specific pathology, that profile is indicative of the presence or the likelihood of development of that pathology in the subject. In one embodiment, the methods of the invention are used to identify the stage of progression of a cancer (e.g., breast cancer). In one embodiment, the stage of progression is metastasis or pro-metastasis (e.g., metastatic breast cancer).

Generation of multiple profiles for specific target cells in a subject over a period of time can be used to track the development of an miRNA signature in the target cells. By association, tracking the development of the miRNA signature will in turn track the development of the pathology. Similarly, repeated generation of a profile over a period of time following diagnosis can be performed to track the regression of the miRNA signature, and by association, track the regression of the pathology (e.g., when the subject is receiving treatment). As such the methods described herein can be performed on a subject who is suspected of having the specific pathology, determined to be at risk for the pathology, or diagnosed with the pathology (e.g., receiving treatment). The appropriate period of time to repeat the methods can be determined by the skilled practitioner. In one embodiment, the period of time is from 1-20 days (1, 2, 3, 4, . . . 20 days). In one embodiment, the period of time is from 1-20 weeks (1, 2, 3, 4, . . . 20 weeks). In one embodiment, the period of time is from 1-24 months (e.g., 1, 2, 3, 4, . . . 24 months).

When relevant, the specific location of the target cell within the subject can also be determined by virtue of the location of the nanosensor and/or the location of the emitted fluorescence, which can both be determined through use of the appropriate imaging techniques. The location of magnetic nanosensors can be identified by performing nuclear magnetic resonance imaging on the subject. The location of the emitted fluorescence from a fluorophore can be performed by optical imaging.

Figure 2:
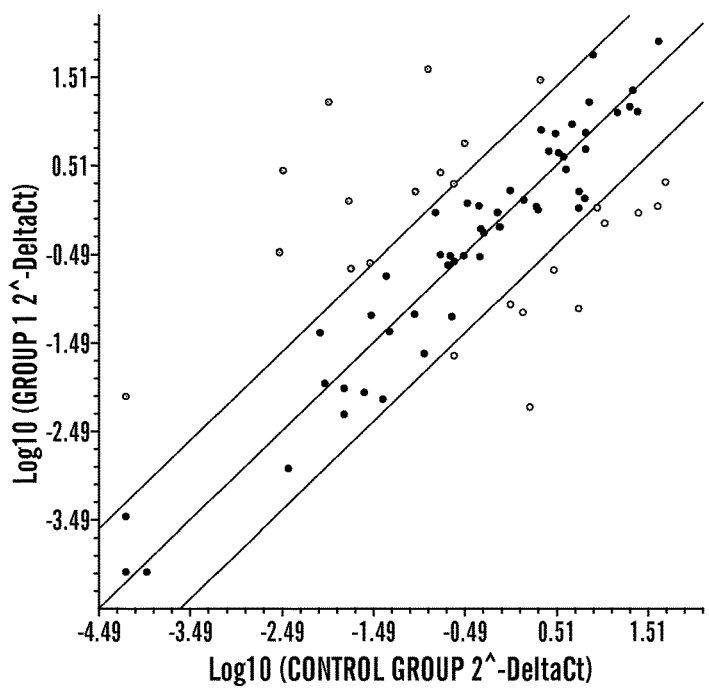
FIG. 2 shows experimental results of microarray analysis of miRNAs. The miRNAs show significant differential expression in lymph node metastases vs. the primary tumor. Top figure is a scatter plot, and the bottom figure is a list of the identified miRNAs.

Signatures of several miRNAs are associated with the pathology of metastatic breast cancer. Relevant miRNAs include, without limitation, let-7a, let-7d, let-7c, let-7i, miR-1, miR-100, miR-10a, miR-10b, miR-340, miR-155, miR-15b, miR-186, miR-222, miR-182, miR-210, miR-193b, miR-26a, miR-27a, miR-29a, miR-27b, miR-200c, miR-29c, miR-424, and miR-141. miRNAs identified as exhibiting higher expression and activity or lower expression and activity in metastatic or pro-metastatic breast cancer are indicated in FIG. 2.

Aspects of the invention recited herein relate to the analysis of expression/activity levels in a target cell (e.g., a cancer cell or a breast cancer cell) by the methods described herein of one or more miRNAs let-7a, let-7d, let-7c, let-7i, miR-1, miR-100, miR-10a, miR-10b, miR-340, miR-155, miR-15b, miR-186, miR-222, miR-182, miR-210, miR-193b, miR-26a, miR-27a, miR-29a, miR-27b, miR-200c, miR-29c, miR-424, and miR-141. In one embodiment, all of the miRNAs are analyzed. In one embodiment, a subset of the miRNAs (miRNAs let-7a, let-7d, let-7c, let-7i, miR-1, miR-100, miR-10a, miR-10b, miR-340, miR-155, miR-15b, miR-186, miR-222, miR-182, miR-210, miR-193b, miR-26a, miR-27a, miR-29a, miR-27b, miR-200c, miR-29c, miR-424, and miR-141) which excludes one or more of the miRNAs (let-7a, let-7d, let-7c, let-7i, miR-1, miR-100, miR-10a, miR-10b, miR-340, miR-155, miR-15b, miR-186, miR-222, miR-182, miR-210, miR-193b, miR-26a, miR-27a, miR-29a, miR-27b, miR-200c, miR-29c, miR-424, and miR-141). In one embodiment, the subset of miRNAs is one or more of miR-10b, miR-155, miR-200c and miR-141. In one embodiment, the subset of miRNAs includes one or more of let-7a, let-7d, let-7i, and miR-1. In one embodiment, the subset of miRNAs includes one or more of miR-424, miR-29c, and miR-27a. In one embodiment, the expression/activity of miR-21 and/or miR-31 and/or one or more other members of the miR-200 family is also analyzed with miRNAs specified herein. Detection of significant differential expression of the analyzed miRNAs in comparison to a control cell is indicative of the breast cancer cells being in a metastatic or pro-metastatic state. In one embodiment, a control cell is a normal breast cell, or a cell from the primary tumor.

Identification of miRNA signatures associated with metastatic breast cancer in a target cell can be used to detect metastatic or pro-metastatic cancer cells (e.g., breast cancer) in a subject. As such, one aspect of the invention relates to a method for detecting metastatic or pro-metastatic breast cancer cells in a subject. The method involves assessing the expression/activity of one or more miRNAs in breast cancer cells of a subject by the methods described herein, and identifying cells which exhibit pro-metastatic miRNA signatures. The specific location of the target cells which exhibit the pro-metastatic signature can further be identified by determination of the location of the nanosensor and/or the location of the emitted fluorescence from the sensor oligos. This can be accomplished by performing nuclear magnetic resonance imaging and/or optical imaging. The specific parameters of the imaging will be determined based on the composition of the specific nanosensor and/or sensor oligo used.

Following detection of a pathology, a treatment regimen appropriate for that pathology (e.g., for metastatic breast cancer) can be administered to the subject. In the absence of detection, the more aggressive treatment regimen can be withheld as unnecessary, and a more appropriate, less aggressive therapy can be pursued. Examples of chemotherapeutic treatments for aggressive cancer therapy are described herein.

The experiments detailed herein exemplify the identification of pro-metastatic miRNA signatures for breast cancer. These methods can further be applied to determining pro-metastatic miRNA signatures for other forms of cancer. Examples of various other forms of cancer are described herein.

Nanoparticles

The nanoparticle, also referred to herein as the delivery particle, is a spherical, ellipsoidal or amorphous shaped object with a diameter from about 2 nm to about 200 nm (e.g., the diameter fall within a range from about 10 nm to 200 nm, from about 2 nm to 100 nm, from about 2 nm to 40 nm, from about 2 nm to 30 nm, from about 2 nm to 20 nm, from about 2 nm to 15 nm, from about 100 nm to 200 nm, and from about 150 nm to 200 nm). In one embodiment the nanoparticle has a diameter from about 10 nm to 30 nm. In one embodiment, the nanoparticle has a diameter from about 20 nm to 30 nm.

The nanoparticle object typically has a polymer coating (e.g., polyethylene glycol PEG, dextran, polyvinylpyrrolidone (PVP), fatty acids, polypeptides, chitosan and gelatin, chitosan, polyethylenimine, and combinations thereof). Combinations of polymers (co-polymers) are also known and can be used. Specifically chitosan, polyethylene glycol and polyethylenimine have been used (Kievit et al., ACS Nano. 2010; 4:4587-94). Various polymers suitable for use in the nanoparticle are known in the art and described herein.

The surface of the nanoparticle can further be functionalized with a chemical group such as amines (e.g., via the polymer coating). Such functionalization will promote endosomal swelling and rupture upon cellular uptake.

In one embodiment the nanoparticle is magnetic. The term "magnetic" is used to describe a composition that is responsive to a magnetic field. Non-limiting examples of magnetic compositions (e.g., any of the therapeutic nanoparticles described herein) can contain a material that is paramagnetic, superparamagnetic, ferromagnetic, or diamagnetic. Non-limiting examples of magnetic compositions contain a metal oxide selected from the group of: magnetite; ferrites (e.g., ferrites of manganese, cobalt, and nickel); Fe(II) oxides; and hematite, and metal alloys thereof. Additional magnetic materials are described herein and are known in the art.

The nanoparticle can contain a core of a magnetic material (e.g., a therapeutic magnetic nanoparticle). In one embodiment the magnetic material or particle can be a diamagnetic, paramagnetic, superparamagnetic, or ferromagnetic material, or combinations thereof, that is responsive to a magnetic field. The magnetic nanoparticle can contain a core of a magnetic material containing a metal oxide examples of which include, without limitation, magnetite; ferrites (e.g., ferrites of manganese, cobalt, and nickel); Fe(II) oxides, and hematite, and metal alloys thereof. The core of magnetic material can be formed by converting metal salts to metal oxides using methods known in the art (e.g., Kieslich et al, Inorg. Chem. 2011). In one embodiment, the nanoparticle contains cyclodextrin gold or quantum dots. Methods that can be used to generate magnetic nanoparticles are described in Medarova et al, Methods Mol. Biol. 555: 1-13, 2009; and Medarova et al, Nature Protocols 1:429-431, 2006. Additional magnetic materials and methods of making magnetic materials are known in the art. Magnetic nanoparticle suitable for imaging will facilitate the determination of the position or localization of the nanosensors described herein. (e.g., following the administration of one or more doses of a magnetic nanosensors).

In one embodiment, the nanoparticle does not contain a magnetic material. For example, the nanoparticle can contain, at least in part, a polymer core (e.g., poly(lactic-co-glycolic acid)). Such a non-magnetic nanoparticle can contain any of the polymers described herein, or combinations thereof.

Any number of art known materials can be used to prepare nanoparticles (magnetic or non-magnetic), including, but not limited to, gums (e.g., Acacia, Guar), chitosan, gelatin, sodium alginate, and albumin. Additional polymers that can be used to generate the therapeutic nanoparticles described herein are known in the art. For example, polymers that can be used to generate the therapeutic nanoparticles include, but are not limited to, cellulosics, poly(2-hydroxy ethyl methacrylate), poly(N-vinyl pyrrolidone), poly(methyl methacrylate), poly(vinyl alcohol), poly(acrylic acid), polyacrylamide, poly(ethylene-co-vinyl acetate), poly(ethylene glycol), poly(methacrylic acid), polylactides (PLA), polyglycolides (PGA), poly(lactide-co-glycolides) (PLGA), polyanhydrides, polyorthoesters, polycyanoacrylate and polycaprolactone. A combination of two or more polymers may also make up the nanoparticle.

Method for the synthesis of iron oxide nanoparticles include, for example, physical and chemical methods. For example, iron oxides can be prepared by co-precipitation of $Fe^{2+}$ and $Fe^{3+}$ salts in an aqueous solution. The resulting core consists of magnetite ($Fe_3C''4$), maghemite ($y$-$Fe^2C)^3$) or a mixture of the two. The anionic salt content (chlorides, nitrates, sulphates etc), the $Fe^{2+}$ and $Fe^{3+}$ ratio, pH and the ionic strength in the aqueous solution all play a role in controlling the size. It is important to prevent the oxidation of the synthesized nanoparticles and protect their magnetic properties by carrying out the reaction in an oxygen free environment under inert gas such as nitrogen or argon. The coating materials can be added during the co-precipitation process in order to prevent the agglomeration of the iron oxide nanoparticles into microparticles. The skilled practitioner will appreciate that any number of art known surface coating materials can be used for stabilizing iron oxide nanoparticles, among which are synthetic and natural polymers, such as, for example, polyethylene glycol (PEG), dextran, polyvinylpyrrolidone (PVP), fatty acids, polypeptides, chitosin, gelatin, and combinations thereof.

Suitable polymers that can be used to coat the core of magnetic material include without limitation: polystyrenes, polyacrylamides, polyetherurethanes, polysulfones, fluorinated or chlorinated polymers such as polyvinyl chloride, polyethylenes, and polypropylenes, polycarbonates, and polyesters. Additional examples of polymers that can be used to coat the core of magnetic material include polyolefins, such as polybutadiene, polydichlorobutadiene, polyisoprene, polychloroprene, polyvinylidene halides, polyvinylidene carbonate, and polyfluorinated ethylenes. A number of copolymers, including styrene/butadiene, alpha-methyl styrene/dimethyl siloxane, or other polysiloxanes can also be used to coat the core of magnetic material (e.g., polydimethyl siloxane, polyphenylmethyl siloxane, and polytrifluoropropylmethyl siloxane). Additional polymers that can be used to coat the core of magnetic material include polyacrylonitriles or acrylonitrile-containing polymers, such as poly alpha-acrylanitrile copolymers, alkyd or terpenoid resins, and polyalkylene polysulfonates. In one embodiment, the polymer coating is dextran.

U.S. Pat. No. 4,421,660 note that polymer coated particles of an inorganic material are conventionally prepared by (1) treating the inorganic solid with acid, a combination of acid and base, alcohol or a polymer solution; (2) dispersing an addition polymerizable monomer in an aqueous dispersion of a treated inorganic solid and (3) subjecting the resulting dispersion to emulsion polymerization conditions, (col. 1, lines 21-27) U.S. Pat. No. 4,421,660 also discloses a method for coating an inorganic nanoparticles with a polymer, which comprises the steps of (1) emulsifying a hydrophobic, emulsion polymerizable monomer in an aqueous colloidal dispersion of discrete particles of an inorganic solid and (2) subjecting the resulting emulsion to emulsion polymerization conditions to form a stable, fluid aqueous colloidal dispersion of the inorganic solid particles dispersed in a matrix of a water-insoluble polymer of the hydrophobic monomer (col. 1, lines 42-50). Alternatively, polymer-coated magnetic material can be obtained commercially that meets the starting requirements of size. For example, commercially available ultrasmall superparamagnetic iron oxide nanoparticles include NCI 00150 Injection (Nycomed Amersham, Amersham Health) and Ferumoxytol (AM AG Pharmaceuticals, Inc.).

The material used in the composition of the nanoparticles, the methods for preparing, coating, and methods for controlling the size of the nanoparticles can vary substantially. Key issues include the biodegradability, toxicity profile, and pharmacokinetics/pharmacodynamics of the nanoparticles. The composition and/or size of the nanoparticles are key determinants of their biological fate. For example, larger nanoparticles are typically taken up and degraded by the liver, whereas smaller nanoparticles (<30 nm in diameter)

typically circulate for a long time (sometimes over 24-hr blood half-life in humans) and accumulate in lymph nodes and the interstitium of organs with hyperpermeable vasculature, such as tumors.

In one embodiment, the polymer coating over the core (magnetic or non-magnetic) is suitable for attaching or coupling one or more biological agents (e.g., such as any of the nucleic acids, fluorophores, or targeting peptides described herein). One or more biological agents (e.g., a nucleic acid, fluorophore, or targeting peptide) can be fixed to the polymer coating by chemical coupling (covalent bonds). In one embodiment, the nanoparticle is formed by a method that includes coating the core material with a polymer that is relatively stable in water. In one embodiment, the nanoparticle is formed by a method that includes coating a magnetic material with a polymer or absorbing the magnetic material into a thermoplastic polymer resin having reducing groups thereon. A coating can also be applied to a magnetic material using the methods described in U.S. Pat. Nos. 5,834,121, 5,395,688, 5,356,713, 5,318,797, 5,283,079, 5,232,789, 5,091,206, 4,965,007, 4,774,265, 4,770,183, 4,654,267, 4,554,088, 4,490,436, 4,336,173, and 4,421,660; and WO10/111066 (each disclosure of which is incorporated herein by reference).

Quencher-Fluorophore Pairs

The sensor oligonucleotide contains both members of a quencher-fluorophore pair positioned within the oligonucleotide such that the intact oligonucleotide emits minimal to no fluorescence. Fluorescence resonance energy transfer (FRET) is a form of molecular energy transfer (MET), a process by which energy is passed non-radioactively between a donor molecule and an acceptor molecule. FRET arises from the properties of certain chemical compounds; when excited by exposure to particular wavelengths of light, they emit light (i.e., they fluoresce) at a different wavelength. Such compounds are termed fluorophores. In FRET, energy is passed non-radioactively over a long distance (e.g., 10-100 Angstroms) between a donor molecule, which is a fluorophore, and an acceptor molecule, which is a quencher. The donor absorbs a photon and transfers this energy non-radioactively to the acceptor (Forster, 1949, Z. Naturforsch. A4: 321-327; Clegg, 1992, Methods Enzymol. 211: 353-388). When the excited-state energy of the donor is transferred to a non-fluorophore acceptor, the fluorescence of the donor is quenched without subsequent emission of fluorescence by the acceptor. In this case, the acceptor functions as a quencher. In order for energy transfer to occur, the donor and acceptor molecules must typically be in close proximity (e.g., up to 70 to 100 Angstroms) (Clegg, 1992, Methods Enzymol. 211: 353-388; Selvin, 1995, Methods Enzymol. 246: 300-334). The efficiency of energy transfer falls off rapidly with the distance between the donor and acceptor molecules. Effectively, this means that FRET can most efficiently occur up to distances of about 70 Angstroms. In one embodiment, the fluorophore and quencher are between about 3 nucleotides and about 20 nucleotides apart on the same oligonucleotide. In one embodiment, the distance is between about 6 nucleotides and about 19 nucleotides.

In one embodiment, the quencher-fluorophore is suitable for optical imaging, such as dyes that have an emission maximum over 600 nm. Examples of dyes are AlexaFluor® 594, AlexaFluor® 647, IRDye®-700DX, AlexaFluor® 750, IRDye®-800, FITC, Cy3®, Cy5®, DyLight594®, and IRDye-700DX®. Other fluorophores include, without limitatin, fluorescein, 5-carboxyfluorescein (FAM), 2'7'-dimethoxy-4'5'-dichloro-6-carboxyfluorescein (JOE), rhodamine, 6-carboxyrhodamine (R6G), N,N,N',N'-tetramethyl-6-carboxyrhodamine (TAMRA), 6-carboxy-X-rhodamine (ROX), 4-(4'-dimethylaminophenylazo) benzoic acid (DABCYL), and 5-(2'-aminoethyl)aminonaphthalene-1-sulfonic acid (EDANS). In one embodiment, the quencher is a Black Hole Quencher®, an IOWA Black® quencher, an Eclipse® Dark quencher and a DABCYL quencher and a derivative thereof. In one embodiment the quencher-fluorophore pair is is Iowa Black Hole RQ® quencher and Cy5® fluorophore, or IRDye®-700DX-QC-1.

Targeting Peptides

The sensor oligo or nanosensor described herein can also contain one or more targeting peptides covalently-linked thereto. Covalent linkage to the nanosensor is typically by linkage to the nanoparticle therein. Targeting peptides can be used to deliver an agent (e.g., the sensor oligo or nanosensor described herein) to a specific cell type or tissue. Targeting peptides can also further promote uptake of the sensor oligo or nanosensor by the target cell (e.g., by binding to a receptor that is internalized). Targeting peptides often contain an amino acid sequence that is recognized by a molecule present on the surface of a cell (e.g., a cell type present in a target tissue). For example, a targeting peptide comprising an RGD peptide specifically binds to $\alpha v \beta 3$ integrin expressed in the plasma membrane of breast cancer cells. Other targeting peptides that can be covalently-linked to any of the therapeutic nanoparticles described herein include: CendR, which binds to Neuropilin-1, an EPPT peptide (SEQ ID NO: 11), a contiguous sequence of amino acids (e.g., at least 10, 15, or 20) present within galectin-3, a contiguous sequence of amino acids (e.g., at least 10, 15, or 20) present within gonadotropin-releasing hormone, NYLH-NHPYGTVG (SEQ ID NO: 1), SNPFSKPYGLTV (SEQ ID NO: 2), GLHESTFTQRRL (SEQ ID NO: 3), YPHYS-LPGSSTL (SEQ ID NO: 4), SSLEPWHRTTSR (SEQ ID NO: 5), LPLALPRHNASV (SEQ ID NO: 6), pAla-(Arg)7-Cys (SEQ ID NO: 12) (e.g., CM-PA1a-(Arg)7-Cys (SEQ ID NO: 12)), a contiguous sequence of amino acids (e.g., at least 10, 15, or 20) present within somatostatin, a contiguous sequence of amino acids (e.g., at least 10, 15, or 20) present within cholecystokinin-A, a contiguous sequence of amino acids (e.g., at least 10, 15, or 20) present within cholecystokinin-B, a contiguous sequence of amino acids (e.g., at least 10, 15, or 20) present within glucagon-like peptide-1, a contiguous sequence of amino acids (e.g., at least 10, 15, or 20) present in bombesin, a contiguous sequence of amino acids (e.g., at least 10, 15, or 20) present within neuropeptide-Y, a contiguous sequence of amino acids (e.g., at least 10, 15, or 20) present within vasoactive intestinal peptide, a contiguous sequence of amino acids (e.g., at least 10, 15, or 20) present within gastrin-1, a contiguous sequence of amino acids (e.g., at least 10, 15, or 20) present within neurotensin, a contiguous sequence of amino acids (e.g., at least 10, 15, or 20) present within vascular endothelial growth factor, a contiguous sequence of amino acids (e.g., at least 10, 15, or 20) present within endoglin, or a contiguous sequence of amino acids (e.g., at least 10, 15, or 20) present within epithelial growth factor. Additional examples of targeting peptides are described in U.S. Patent Application Publication No. 2008/00056998 (herein incorporated by reference in its entirety).

In one embodiment, the targeting peptide can be covalently linked to the nanoparticle at its N-terminus or at its C-terminus. In one embodiment, the targeting peptide can be covalently linked to the nanoparticle through an amino acid side chain. Linkage can be achieved through routine methods, for example, through a chemical moiety containing a disulfide bond, an amide bond, or a thioether bond.

Non-limiting examples of methods of covalently linking a targeting peptide to a nanoparticle are described in Hofmann et al, Proc. Nat. Acad. Sci. U.S.A. 10:3516-3518, 2007; Chan et al, PLoS ONE 2(11): e1 164, 2007; U.S. Pat. No. 7,125,669; U.S. Patent Application Publication No. 20080058224; U.S. Patent Application Publication No. 20090275066; and Mateo et al, Nature Protocols 2: 1022-1033, 2007 (each of which are incorporated by reference in their entirety). In one embodiment, the nanoparticle can be activated for attachment with a targeting peptide, for example the therapeutic nanoparticle can be epoxy-activated, carboxyl-activated, iodoacetyl-activated, aldehyde-terminated, amine-terminated, or thiol-activated.

Modified Nucleotides

In one embodiment, the nucleic acid molecule of the sensor oligo described herein can contain at least one modified nucleotide (a nucleotide containing a modified base or sugar). In one embodiment, the nucleic acid molecule can contain at least one modification in the phosphate (phosphodiester) backbone. The introduction of these modifications can increase the stability, or improve the hybridization or solubility of the nucleic acid molecule.

The nucleic acid molecules described herein can contain one or more (e.g., 2, 3, 4, 5, 6, 7, 8, etc) modified nucleotides. The modified nucleotides can contain a modified base or a modified sugar. Non-limiting examples of modified bases include: 8-oxo-N6-methyladenine, 7-deazaxanthine, 7-deazaguanine, N4, N4-ethanocytosin, N6, N6-ethano-2,6-diaminopurine, 5-(C3-C6)-alkynyl-cytosine, pseudoisocytosine, 2-hydroxy-5-methyl-4-triazolopyridin, isocytosine, isoguanine, 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Additional examples of modified bases include, without limitation, those nucleobases described in U.S. Pat. Nos. 5,432,272 and 3,687,808 (herein incorporated by reference), Freier et al, Nucleic Acid Res. 25:4429-4443, 1997; Sanghvi, Antisense Research and Application, Chapter 15, Ed. S. T. Crooke and B. Lebleu, CRC Press, 1993; Englisch, et al, Angewandte Chemie 30:613-722, 1991; Kroschwitz, Concise Encyclopedia of Polymer Science and Engineering, John Wiley & Sons, pp. 858-859, 1990; and Cook, Anti-Cancer Drug Design 6:585-607, 1991. Additional non-limiting examples of modified bases include universal bases (e.g., 3-nitropyrole and 5-nitro indole). Other modified bases include pyrene and pyridyloxazole derivatives, pyrenyl, pyrenylmethylglycerol derivatives, and the like. Other preferred universal bases include pyrrole, diazole, or triazole derivatives, including those universal bases known in the art.

In one embodiment, the modified nucleotide can contain a modification in its sugar moiety. For example, modified nucleotides that contain a modified sugar are locked nucleotides (LNAs). LNA monomers are described in WO 99/14226 and U.S. Patent Application Publications Nos. 20110076675, 20100286044, 20100279895, 20100267018, 20100261175, 20100035968, 20090286753, 20090023594, 20080096191, 20030092905, 20020128381, and 20020115080 (herein incorporated by reference). Other LNAs are disclosed in U.S. Pat. No. 6,043,060, U.S. Pat. No. 6,268,490, WO 01/07455, WO 01/00641, WO 98/39352, WO 00/56746, WO 00/56748, and WO 00/66604 (herein incorporated by reference), as well as in Morita et al, Bioorg. Med. Chem. Lett. 12(1):73-76, 2002; Hakansson et al, Bioorg. Med. Chem. Lett. 11(7):935-938, 2001; Koshkin et al, J. Org. Chem. 66(25):8504-8512, 2001; Kvaerno et al, J. Org. Chem. 66(16):5498-5503, 2001; Hakansson et al, J. Org. Chem. 65(17):5161-5166, 2000; Kvaerno et al, J. Org. Chem. 65(17):5167-5176, 2000; Pfundheller et al, Nucleosides Nucleotides 18(9):2017-2030, 1999; and Kumar et al, Bioorg. Med. Chem. Lett. 8(16):2219-2222, 1998. In one embodiment, the modified nucleotide is an oxy-LNA monomer, such as those described in WO 03/020739.

Modified nucleotides may also include antagomirs (2'-0-methyl-modified, cholesterol-conjugated single stranded RNA analogs); ALN (a-L-LNA); ADA (2'-N-adamantylmethyl carbonyl-2'-amino-LNA); P YR (2'-N-pyrenyl-1-methyl-2'-amino-LNA); OX (oxetane-LNA); ENA (2'-0, 4"-C-ethylene bridged nucleic acid); AENA (2'-deoxy-2'-N, 4'-C-ethylene-LNA); CLNA (2',4'-carbocyclic-LNA); and CENA (2',4'-carbocyclic-ENA); HM-modified DNAs (4'-C-hydroxymethyl-DNA); 2'-substituted RNAs (with 2'-0-methyl, 2'-fluoro, 2'-aminoethoxymethyl, 2'-aminopropoxymethyl, 2'-aminoethyl, 2'-guanidinoethyl, 2'-cyanoethyl, 2'-aminopropyl); and RNAs with radical modifications of the ribose sugar ring, such as Unlocked Nucleic Acid (UNA), Altritol Nucleic Acid (ANA) and Hexitol Nucleic Acid (FiNA) (see, Bramsen et al, Nucleic Acids Res. 37:2867-81, 2009).

The nucleic acids described herein can also contain a modification in the phosphodiester backbone. For example, at least one linkage between any two contiguous (adjoining) nucleotides in the molecule can be connected by a moiety containing 2 to 4 groups/atoms selected from the group of: —CH2—, —O—, —S—, —NRH—, >C=0, >C=NRH, >C=S, —Si(R")2—, —SO—S(0)2—, —P(0)2—, —PO(BH3)—, —P(0,S)—, —P(S)2—, —PO(R")—, —PO(OCH3)—, and —PO(NHRH)—, where RH is selected from hydrogen and Ci_4-alkyl, and R" is selected from Ci_6-alkyl and phenyl. Illustrative examples of such linkages are —CH2—CH2—CH2—, —CH2—CO—CH2—, CH2—CHOH—CH2—, —O—CH2—O—, —O—CH2—CH2—, —O—CH2—CH= (including R5 when used as a linkage to a succeeding monomer), —CH2—CH2—O—, —NRH—CH2—CH2—, —CH2—CH2—NRH—, —CH2—NRH—CH2—, —O—CH2—CH2—NRH—, —NRH—CO—O—, —NRH—CO—NRH—, —NRH—CS—NRH—, —NRH—C(=NRH)—NRH—, —NRH—CO—CH2—NRH—, —O—CO—O—, —O—CO—CH2—O—, —O—CH2—CO—O—, —CH2—CO—NRH—, —O—CO—NRH—, —NRH—CO—CH2—, —O—CH2—CO—NRH—, —O—CH2—CH2—NRH—, —CH=N—O—, —CH2—NRH—O—, —CH2—O—N= (including R5 when used as a linkage to a succeeding monomer), —CH2—O—NRH—, —CO—NRH—CH2—, —CH2—NRH—O—, —CH2—NRH—CO—, —O—NRH—CH2—, —O—NRH—, —O—CH2—S—, —S—CH2—O—, —CH2—CH2—S—, —O—CH2—CH2—S—, —S—CH2—CH= (including R5 when used as a linkage to a succeeding monomer), —S—CH2—CH2—, —S—CH2—CH2—O—, —S—CH2—CH2—S—, —CH2—S—CH2—, —CH2—SO—CH2—, —CH2—S02—CH2—, —O—SO—O—, —O—S(0)2—O—, —O—S(0)2—CH2—, —O—S(0)2—NRH—, —NRH—S(0)2—CH2—, —O—S(0)2—CH2—, —O—P(0)2—O—, —O—P(0,S)—O—, —O—P(S)2—O—, —S—P(0)2—O—, —S—P(0,S)—O—, —S—P(S)2—O—, —O—P(0,S)—S—, —O—P(S)2—s—, —s—P(0)2—S—, —S—P(0,S)—S—, —S—P(S)2—S—, —O—PO(R")—o—, —o—PO(OCH3)—O—, —O—PO—(OCH2CH3)—O—, —O—PO(OCH2S—R)—O—, —O—PO(BH3)—O—, —O—PO(NHRN)—O—, —O—P(0)2—NRH—, —NRH—P(0)2—O—, —O—P(0,NRH)2—O—, —CH2—P(0)2—O—, —O—P(0)2—CH2—, and —O—Si(R")2—O—; among which —CH2—CO—NRH—, —CH2—NRH—O—, —S—CH2—O—, —O—P(0)2—O—, —O—P(0,S)—O—, —O—P(S)2—O—, —NRH—P(0)2—O—, —O—P(0,NRH)—O—, —O—PO(R")—O—, —O—PO(CH3)—O—, and —O—PO(NHRN)—O—, where RH is selected form hydrogen and $C_{i\_4}$-alkyl, and R" is selected from $C_{i\_6}$-alkyl and phenyl. Further illustrative examples are given in Mesmaeker et. al, Curr. Opin. Struct. Biol. 5:343-355, 1995; and Freier et al, Nucleic Acids Research 25:4429-43, 1997. The left-hand side of the inter-nucleoside linkage is bound to the 5-membered ring as substituent P* at the 3'-position, whereas the right-hand side is bound to the 5'-position of a preceding monomer.

In one embodiment, the deoxyribose phosphate backbone of the nucleic acid is modified to generate peptide nucleic acids (see Hyrup et al, Bioorganic & Medicinal Chem. 4(1): 5-23, 1996). Peptide nucleic acids (PNAs) are nucleic acid mimics, e.g., DNA mimics, in which the deoxyribose phosphate backbone is replaced by a pseudopeptide backbone and only the four natural nucleobases are retained. The neutral backbone of PNAs allows for specific hybridization to DNA and RNA under conditions of low ionic strength. The synthesis of PNA oligomers can be performed using standard solid phase peptide synthesis protocols, e.g., as described in Hyrup et al, 1996, supra; Perry-O'Keefe et al, Proc. Natl. Acad. Sci. U.S.A. 93: 14670-675, 1996. PNAs can be modified, e.g., to enhance their stability or cellular uptake, by attaching lipophilic or other helper groups to PNA, by the formation of PNA-DNA chimeras, or by the use of liposomes or other techniques of delivery known in the art. For example, PNA-DNA chimeras can be generated which may combine the advantageous properties of PNA and DNA. Such chimeras allow DNA recognition enzymes, e.g., RNAse H, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup, 1996, supra). The synthesis of PNA-DNA chimeras can be performed as described in Hyrup, 1996, supra, and Finn et al, Nucleic Acids Res. 24:3357-63, 1996. For example, a DNA chain can be synthesized on a solid support using standard phosphoramidite coupling chemistry and modified nucleoside analogs. Compounds such as 5'-(4-methoxytrityl)amino-5'-deoxy-thymidine phosphoramidite can be used as a link between the PNA and the 5' end of DNA (Mag et al, Nucleic Acids Res., 17:5973-88, 1989). PNAmonomers are then coupled in a stepwise manner to produce a chimeric molecule with a 5' PNA segment and a 3' DNA segment (Finn et al, Nucleic Acids Res. 24:3357-63, 1996). Alternatively, chimeric molecules can be synthesized with a 5' DNA segment and a 3' PNA segment (Peterser et al, Bioorganic Med. Chem. Lett. 5: 1119-11124, 1975).

In one embodiment, any of the nucleic acids described herein can be modified at either the 3' or 5' end (e.g. depending on how the nucleic acid is covalently-linked to an additional molecule in a larger composition such as a nanoparticle) by any type of modification known in the art. For example, either end may be capped with a protecting group, attached to a flexible linking group, or attached to a reactive group to aid in attachment to the substrate surface (the polymer coating). Non-limiting examples of 3' or 5' blocking groups include: 2-amino-2-oxyethyl, 2-aminobenzoyl, 4-aminobenzoyl, acetyl, acetyloxy, (acetylamino)methyl, 3-(9-acridinyl), tricyclo[3.3.1.1(3,7)]dec-1-yloxy, 2-aminoethyl, propenyl, (9-anthracenylmethoxy)carbonyl, (1,1-dmimethylpropoxy)carbonyl, (1,1-dimethylpropoxy) carbonyl, [1-methyl-1-[4-(phenylazo)phenyl]ethoxy]carbonyl, bromoacetyl, (benzoylamino)methyl, (2-bromoethoxy) carbonyl, (diphenylmethoxy)carbonyl, 1-methyl-3-oxo-3-phenyl-1-propenyl, (3-bromo-2-nitrophenyl)thio, (1,1-dimethylethoxy)carbonyl, [[(1,1-dimethylethoxy)carbonyl] amino]ethyl, 2-(phenylmethoxy)phenoxy, (1=[1,1'-biphenyl]-4-yl-1-methylethoxy) carbonyl, bromo, (4-bromophenyl)sulfonyl, 1H-benzotriazol-1-yl, [(phenylmethyl) thio]carbonyl, [(phenylmetyl)thio]methyl, 2-methylpropyl, 1,1-dimethylethyl, benzoyl, diphenylmethyl, phenylmethyl, carboxyacetyl, aminocarbonyl, chlorodifluoro acetyl, trifluoromethyl, cyclohexylcarbonyl, cycloheptyl, cyclohexyl, cyclohexylacetyl, chloro, carboxymethyl, cyclopentylcarbonyl, cyclopentyl, cyclopropylmethyl, ethoxycarbonyl, ethyl, fluoro, formyl, 1-oxohexyl, iodo, methyl, 2-methoxy-2-oxoethyl, nitro, azido, phenyl, 2-carboxybenzoyl, 4-pyridinylmethyl, 2-piperidinyl, propyl, 1-methylethyl, sulfo, and ethenyl. Additional examples of 5' and 3 ' blocking groups are known in the art. In some embodiments, the 5' or 3' blocking groups prevent nuclease degradation of the molecule.

The nucleic acids described herein can be synthesized using any methods known in the art for synthesizing nucleic acids (see, e.g., Usman et al, J. Am. Chem. Soc. 109:7845, 1987; Scaringe et al, Nucleic Acid Res. 18:5433, 1990; Wincott et al, Methods Mol. Biol. 74:59, 1997; and Milligan, Nucleic Acid Res. 21:8783, 1987). These typically make use of common nucleic acid protecting and coupling groups. Synthesis can be performed on commercial equipment designed for this purpose, e.g., a 394 Applied Biosystems, Inc. synthesizer, using protocols supplied by the manufacturer. Additional methods for synthesizing the molecules described herein are known in the art. Alternatively, the nucleic acids can be specially ordered from commercial vendors that synthesize oligonucleotides.

Linkage of Sensor Oligo and Nanoparticle

In one embodiment, the sensor oligo nucleic acid is attached to the nanoparticle at its 5' end. In one embodiment, the nucleic acid is attached to the nanoparticle at its 3' end. In one embodiment, the nucleic acid is attached to the nanoparticle through a base present in the nucleic acid. In one embodiment, the nucleic acid (e.g., any of the nucleic acids or modified nucleic acids described herein) is attached to the nanoparticle (e.g., to the polymer coating of the therapeutic nanoparticle) through a chemical moiety that contains a thioether bond or a disulfide bond. In one embodiment, the nucleic acid is attached to the nanoparticle through a chemical moiety that contains an amide bond.

A variety of different methods can be used to covalently link a nucleic acid to a nanoparticle. Non-limiting examples of methods that can be used to link a nucleic acid to a magnetic particle are described in EP 0937097; U.S. Pat. No. RE41005; Lund et al, Nucleic Acid Res. 16: 10861, 1998;

Todt et al, Methods Mol. Biol. 529:81-100, 2009; Brody et al, J. Biotechnol. 74:5-13, 2000; Ghosh et al, Nucleic Acids Res. 15:5353-5372, 1987; U.S. Pat. No. 5,900,481; U.S. Pat. No. 7,569,341; U.S. Pat. No. 6,995,248; U.S. Pat. No. 6,818,394; U.S. Pat. No. 6,811,980; U.S. Pat. No. 5,900,481; and U.S. Pat. No. 4,818,681 (each of which is incorporated by reference in its entirety). In some embodiments, carboiimide is used for the end-attachment of a nucleic acid to a nanoparticle. In some embodiments, the nucleic acid is attached to the nanoparticle through the reaction of one of its bases with an activated moiety present on the surface of the nanoparticle (e.g., the reaction of an electrophilic base with a nucleophilic moiety on the surface of the nanoparticle, or the reaction of a nucleophilic base with a electrophilic residue on the surface of the nanoparticle). In some embodiments, a 5'-NH2 modified nucleic acid is attached to a nanoparticle containing CNBr-activated hydroxyl groups (see, e.g., Lund et al, supra). Additional methods for attaching an amino-modified nucleic acid to a nanoparticle are described below. In some embodiments, a 5'-phosphate nucleic acid is attached to a nanoparticle containing hydroxyl groups in the presence of a carbodiimide (see, e.g., Lund et al, supra). Other methods of attaching a nucleic acid to a nanoparticle include carboiimide-mediated attachment of a 5'-phosphate nucleic acid to a NH2 group on a nanoparticle, and carboiimide-mediated attachment of a 5'-NH2 nucleic acid to a nanoparticle having carboxyl groups (see, e.g., Lund et al, supra).

In one embodiment, a nucleic acid can be produced that contains a reactive amine or a reactive thiol group. The amine or thiol in the nucleic acid can be linked to another reactive group. The two common strategies to perform this reaction are to link the nucleic acid to a similar reactive moiety (amine to amine or thiol to thiol), which is called homobifunctional linkage, or to link to the nucleic acid to an opposite group (amine to thiol or thiol to amine), known as heterobifunctional linkage. Both techniques can be used to attach a nucleic acid to a nanoparticle (see, for example, Misra et al, Bioorg. Med. Chem. Lett. 18:5217-5221, 2008; Mirsa et al, Anal. Biochem. 369:248-255, 2007; Mirsa et al, Bioorg. Med. Chem. Lett. 17:3749-3753, 2007; and Choithani et al, Methods Mo I Biol. 381: 133-163, 2007).

Traditional attachment techniques, especially for amine groups, have relied upon homobifunctional linkages. One of the most common techniques has been the use of bisaldehydes such as glutaraldehyde. Disuccinimydyl suberate (DSS), commercialized by Syngene (Frederick, Md.) as synthetic nucleic acid probe (SNAP) technology, or the reagent p-phenylene diisothiocyanate can also be used to generate a covalent linkage between the nucleic acid and the nanoparticle. N,N'-o-phenylenedimaleimide can be used to cross-link thiol groups. With all of the homobifunctional cross-linking agents, the nucleic acid is initially activated and then added to the nanoparticle (see, for example, Swami et al, Int. J. Pharm. 374: 125-138, 2009, Todt et al, Methods Mol. Biol. 529:81-100, 2009; and Limanskii, Biofizika 51:225-235, 2006).

Heterobifunctional linkers can also be used to attach a nucleic acid to a nanoparticle. For example, N-succinidimidyl-3-(2-pyridyldithio)proprionate (SPDP) initially links to a primary amine to give a dithiol-modified compound. This can then react with a thiol to exchange the pyridylthiol with the incoming thiol (see, for example, Nostrum et al, J. Control Release 15; 153(1):93-102, 2011, and Berthold et al, Bioconjug. Chem. 21:1933-1938, 2010).

An alternative approach for thiol use has been a thiol-exchange reaction. If a thiolated nucleic acid is introduced onto a disulfide of a nanoparticle, a disulfide-exchange reaction can occur that leads to the nucleic acid being covalently bonded to the nanoparticle by a disulfide bond. A multitude of potential cross-linking chemistries are available for the heterobifunctional cross-linking of amines and thiols. Generally, these procedures have been used with a thiolated nucleotide. Reagents typically employed have been NHS (N-hydroxysuccinimide ester), MBS (m-maleimidobenzoyl-N-succinimide ester), and SPDP (a pyridyldisulfide-based system). The heterobifunctional linkers commonly used rely upon an aminated nucleic acid.

Pharmaceutical Compositions

Another aspect of the invention relates to a pharmaceutical composition that contains one or more sensor oligonucleotides and/or nanosensors described herein. A pharmaceutical composition typically contains the active components formulated in the appropriate dosage with a pharmaceutically acceptable carrier. The pharmaceutical compositions can be formulated in any manner known in the art. Pharmaceutical compositions are formulated to be compatible with their intended route of administration (e.g., intravenous, intraarterial, intramuscular, intradermal, subcutaneous, or intraperitoneal). The compositions can include a sterile diluent (e.g., sterile water or saline), a fixed oil, polyethylene glycol, glycerine, propylene glycol or other synthetic solvents, antibacterial or antifungal agents such as benzyl alcohol or methyl parabens, chlorobutanol, phenol, ascorbic acid, thimerosal, and the like, antioxidants such as ascorbic acid or sodium bisulfite, chelating agents such as ethylenediaminetetraacetic acid, buffers such as acetates, citrates, or phosphates, and isotonic agents such as sugars (e.g., dextrose), polyalcohols (e.g., manitol or sorbitol), or salts (e.g., sodium chloride), or any combination thereof. Liposomal suspensions can also be used as pharmaceutically acceptable carriers (see, e.g., U.S. Pat. No. 4,522,811). Preparations of the compositions can be formulated and enclosed in ampules, disposable syringes, or multiple dose vials. Where required (as in, for example, injectable formulations), proper fluidity can be maintained by, for example, the use of a coating such as lecithin, or a surfactant. Absorption of the therapeutic nanoparticles can be prolonged by including an agent that delays absorption (e.g., aluminum monostearate and gelatin). Alternatively, controlled release can be achieved by implants and microencapsulated delivery systems, which can include biodegradable, biocompatible polymers (e.g., ethylene vinyl acetate, polyanhydrides, polyglycolic acid, collagen, polyorthoesters, and polylactic acid; Alza Corporation and Nova Pharmaceutical, Inc.). Compositions containing one or more of any of the therapeutic nanoparticles described herein can be formulated for parenteral (e.g., intravenous, intraarterial, intramuscular, intradermal, subcutaneous, or intraperitoneal) administration in dosage unit form (i.e., physically discrete units containing a predetermined quantity of active compound for ease of administration and uniformity of dosage).

As used here, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) C2-C12 alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

Routes of Administration

The specific route of administration of the sensor oligo or nanosensor will be determined by the skilled practitioner depending upon the specific circumstances. Systemic or localized routes of administration can be used to ultimately deliver an effective amount of the sensor oligo or nanosensor to the target cell. A variety of routes of administration of imaging agents are known in the art and can be adapted to the specific methods described herein. Routes of administration include, without limitation, mucosal, pulmonary, topical, or other localized or systemic route (e.g, enteral and parenteral). In one embodiment, administration is by direct injection into the pathology site (e.g., into a tumor).

The phrases "parenteral administration" and "administered parenterally" as used herein means modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion.

Target Cells

The term "target cells" as used herein, refers to the cells in which the miRNA analysis is desired. It also refers to the cells to which the sensor oligo/nanosensors are delivered. Target cells may be in vitro, such as cells in culture or cells from a biopsy. Target cells may be in vivo. Target cells may be cells that are infected with a pathogen. In one embodiment, target cells are known to have or at risk for, or suspected of developing a pathology. Various pathologies are described herein. In one embodiment, target cells are cancer cells (e.g., primary tumor, metastatic tumor, or pro-metastatic tumor cells).

Diseases and Pathologies

The methods described herein can be used to identify the miRNA signature of a disease or pathology, or of a specific phase or stage of progression of a disease or pathology. In one embodiment, the pathology is uncontrolled cell growth. In one embodiment, the disease is cancer (e.g., breast cancer). In one embodiment, the cancer is breast cancer, a melanoma, adrenal gland cancer, biliary tract cancer, bladder cancer, brain or central nervous system cancer, bronchus cancer, blastoma, carcinoma, a chondrosarcoma, cancer of the oral cavity or pharynx, cervical cancer, colon cancer, colorectal cancer, esophageal cancer, gastrointestinal cancer, glioblastoma, hepatic carcinoma, hepatoma, kidney cancer, leukemia, liver cancer, lung cancer, lymphoma, non-small cell lung cancer, osteosarcoma, ovarian cancer, pancreas cancer, peripheral nervous system cancer, prostate cancer, sarcoma, salivary gland cancer, small bowel or appendix cancer, small-cell lung cancer, squamous cell cancer, stomach cancer, testis cancer, thyroid cancer, urinary bladder cancer, uterine or endometrial cancer, or vulval cancer.

In one embodiment, the disease or pathology results from infection with a pathogen (e.g., virus, bacteria, or parasite). In one embodiment the virus is HIV. In one embodiment, the disease or pathology is a developmental disorder. In one embodiment the disease or pathology is an inflammation related disorder. In one embodiment, the disease or pathology is an autoimmune disorder. In one embodiment the disease or pathology is a neurological disorder. Such diseases or disorders includes, without limitation, Huntington's disease, Parkinson's disease, Multiple Sclerosis, Alzheimer's disease, multiple system atrophy (MSA), spino-cerebellar atrophy, motor neuronopathy, epilepsy or seizures, peripheral neuropathy, cerebral palsy, glaucoma (e.g., angle closure or open angle), age related loss of neurons or neuronal connectivity and related deterioration of sensory, motor, reflect, or cognitive abilities.

Chemotherapeutic Agents

Treatment of metastatic cancer can include, without limitation, administration of one or more of the following cyclophosphamide, mechlorethamine, chlorambucil, melphalan, daunorubicin, doxorubicin, epirubicin, idarubicin, mitoxantrone, valrubicin, paclitaxel, docetaxel, etoposide, teniposide, tafluposide, azacitidine, azathioprine, capecitabine, cytarabine, doxifluridine, fluorouracil, gemcitabine, mercaptopurine, methotrexate, tioguanine, bleomycin, carboplatin, cisplatin, oxaliplatin, bortezomib, carfilzomib, salinosporamide A, all-trans retinoic acid, vinblastine, vincristine, vindesine, and vinorelbine) and/or an analgesic (e.g., acetaminophen, diclofenac, diflunisal, etodolac, fenoprofen, flurbiprofen, ibuprofen, indomethacin, ketoprofen, ketorolac, meclofenamate, mefenamic acid, meloxicam, nabumetone, naproxen, oxaprozin, phenylbutazone, piroxicam, sulindac, tolmetin, celecoxib, buprenorphine, butorphanol, codeine, hydrocodone, hydromorphone, levorphanol, meperidine, methadone, morphine, nalbuphine, oxycodone, oxymorphone, pentazocine, propoxyphene, and tramadol.

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Other than in the operating examples, or where otherwise indicated, all numbers expressing quantities of ingredients or reaction conditions used herein should be understood as modified in all instances by the term "about." The term "about" when used to described the present invention, in connection with percentages means±1%.

In one respect, the present invention relates to the herein described compositions, methods, and respective component (s) thereof, as essential to the invention, yet open to the inclusion of unspecified elements, essential or not ("comprising"). In some embodiments, other elements to be included in the description of the composition, method or respective component thereof are limited to those that do not materially affect the basic and novel characteristic(s) of the invention ("consisting essentially of"). This applies equally to steps within a described method as well as compositions and components therein. In other embodiments, the inventions, compositions, methods, and respective components thereof, described herein are intended to be exclusive of any element not deemed an essential element to the component, composition or method ("consisting of").

All patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The present invention may be as defined in any one of the following numbered paragraphs.

1. A nanosensor for detection of miRNA activity in a target cell comprising:
   a) a delivery particle comprising an iron oxide crystal coated with a polymer; and
   b) a sensor oligonucleotide covalently attached to the polymer, comprising:
      i) a seed region comprising a nucleic acid sequence that is completely complementary to the target miRNA and comprises a cleavage site which can be engaged and cleaved by the target miRNA;
      ii) two non-seed regions that each flank the seed region and are each comprised of a nucleic acid sequence that is complementary to the target miRNA to promote hybridization of the sensor oligonucleotide to the target miRNA; and
      iii) members of a quencher-fluorophore pair;
   wherein the quencher fluorophore pair members respectively flank the cleavage site and are separated by a distance that permits significant quenching of emitted fluorescent signal.

2. The nanosensor of paragraph 1, further comprising a targeting ligand covalently attached to the polymer.

3. The nanosensor of paragraph 2, wherein the targeting ligand is a peptide specific for an internalizing receptor located on the exterior plasma membrane of the target cell.

4. The nanosensor of any one of paragraphs 2-3, wherein the targeting ligand is selected from the group consisting of RGD, folic acid, peptide EPPT (SEQ ID NO: 11), polyarginine peptide (MPAP), and chlorotoxin.

5. The nanosensor of any one of paragraphs 2-4, wherein the polymer is selected from the group consisting of polyethylene glycol PEG, dextran, polyvinylpyrrolidone (PVP), fatty acids, polypeptides, chitosan and gelatin, chitosan, polyethylenimine, and combinations thereof.

6. The nanosensor of any one of paragraphs 1-4, wherein the iron oxide crystal is from about 20-30 nm in diameter and the polymer is dextran.

7. The nanosensor of any one of paragraphs 2-6, wherein the sensor oligonucleotide and/or to the targeting ligand are covalently attached to the polymer by thiol crosslinking 8. The nanosensor of any one of paragraphs 1-7, wherein the polymer is aminated with eipichlorohydrin.

9. The nanosensor of any one of paragraphs 1-8, wherein the entire sensor oligonucleotide nucleic acid sequence is completely complementary to the target miRNA sequence.

10. The nanosensor of any one of paragraphs 1-9, wherein the sensor oligonucleotide is RNA, or a combination of RNA and one or more other nucleic acid-like polymers that hybridize with RNA in a sequence dependent manner, wherein at least the entire seed region is RNA.

11. The nanosensor of any one of paragraphs 1-10, wherein the other nucleic acid-like polymer is DNA, LNA or a 2-0-Me/phosphorothioate backbone.

12. The nanosensor of any one of paragraphs 1-11, wherein the sensor oligonucleotide is from about 18 to about 30 nucleotides in length.

13. The nanosensor of any one of paragraphs 1-12, wherein the sensor oligonucleotide is about 20-25 nucleotides in length.

14. The nanosensor of any one of paragraphs 1-13, wherein the members are separated by a distance of about 9 to about 30 nucleotides.

15. The nanosensor of any one of paragraphs 1-14, wherein the fluorophore of the quencher-fluorophore pair is selected from the group consisting of AlexaFluor® 594, AlexaFluor® 647, IRDye®-700DX, AlexaFluor® 750, IRDye®-800, FITC, Cy3®, and DyLight®594.

16. The nanosensor of any one of paragraphs 1-15, wherein the fluorophore of the quencher-fluorophore pair has an emission maximal over 600 nm.

17. The nanosensor of any one of paragraphs 1-16, wherein the quencher-fluorophore pair is Iowa Black Hole RQ® quencher and Cy5® fluorophore, or IRDye®-700DX-QC-1.

18. The nanosensor of any one of paragraphs 1-17, wherein the delivery particle is functionalized with amines to thereby facilitate endosomal swelling and rupture upon cellular uptake.

19. The nanosensor of any one of paragraphs 1-18, wherein the target miRNA is selected from the group consisting of let-7a, let-7d, let-7c, let-7i, miR-1, miR-100, miR-10a, miR-10b, miR-340, miR-155, miR-15b, miR-186, miR-222, miR-182, miR-210, miR-193b, miR-26a, miR-27a, miR-29a, miR-27b, miR-200c, miR-29c, miR-424, and miR-141.

20. The nanosensor of any one of paragraphs 1-19, wherein the delivery particle is covalently attached to the sensor oligonucleotide at a ratio selected from the group consisting of about 1:10, about 1:20, about 1:30, about 1:40, and about 1:50.

21. The nanosensor of any one of paragraphs 2-20, wherein the delivery particle is covalently attached to the targeting ligand at a ratio of from about 1:1 to about 1:20.

22. A method for assessing the activity of one or more target miRNA in a target cell comprising,
   a) delivering an effective amount of one or more nanosensors of any one of paragraphs 1-21 to the target cell;
   b) detecting fluorescence emitted from the one or more nanosensors; and
   c) comparing the fluorescence detected with that of a normal control cell to thereby assess if the activity of the target miRNA(s) is high, low or normal in the target cell.

23. A method for in vivo profiling of miRNA(s) of one or more target cells in a subject comprising,
   a) administering to the subject an effective amount of one or more nanosensors of any one of paragraphs 1-21 to thereby contact the nanosensors to the target cell(s);
   b) quantitatively detecting in the subject fluorescence emitted from the nanosensors in the target cell(s) to thereby determine the activity of target miRNAs in the target cells of the subject; and
   c) generating a profile from the activity of each target miRNA in each target cell or population thereof from the activity determined in step b).

24. The method of paragraph 23 further comprising determining and recording the location of the target cell within the subject based on the location of the nanosensor and/or the location of the emitted fluorescence by performing nuclear magnetic resonance (NMR) imaging and/or optical imaging.

25. The method of any one of paragraphs 23 or 24 further comprising comparing the fluorescence detected for each target miRNA with that of normal control cells to thereby generate a profile of each target miRNA in the target cell or population thereof as deviated from normal.

26. The method of any one of paragraphs 22-25, wherein the steps are repeated periodically to thereby monitor progression of the miRNA activity in the target cells over time.

27. The method of paragraph 22, wherein the target cell is in vivo.

28. The method of paragraph 22, wherein the target cell is in vitro.

29. The method of any one of paragraphs 22-23, wherein the nanosensors are delivered or administered to thereby produce an intracellular concentration in the target cell of about 250 nM.

30. The method of any one of paragraphs 22-29 wherein the target cell is of a primary tumor, of a metastatic tumor, of a biopsy, virally infected, parasitically infected, or non-infected pathology.

31. The method of any one of paragraphs 22-30, wherein the one or more miRNA is one or more of miRNAs selected from the group consisting of let-7a, let-7d, let-7c, let-7i, miR-1, miR-100, miR-10a, miR-10b, miR-340, miR-155, miR-15b, miR-186, miR-222, miR-182, miR-210, miR-193b, miR-26a, miR-27a, miR-29a, miR-27b, miR-200c, miR-29c, miR-424, and miR-141.

32. The method of any one of paragraphs 22-30, wherein the one or more miRNA comprises miR-10b, miR-155, miR-200C, miR-141, or combinations thereof.

33. The method of paragraph 22, wherein the target cell is in vivo and delivery is by administration to a subject comprising the target cell.

34. The method any one of paragraphs 22-31, wherein administration is by injection.

35. The method of any one of paragraphs 22-34, wherein the dosage is about 5 mg to about 40 mg of iron/kg subject weight.

36. The method of any one of paragraphs 22-35, wherein the dose is about 10 mg of iron/kg subject weight.

37. The method of any one of paragraphs 22-36, wherein detecting is by performance of optical imaging.

38. A method of detecting metastatic or pro-metastatic breast cancer cells in a subject comprising, assessing the activity of one or more miRNAs selected from the group consisting of let-7a, let-7d, let-7c, let-7i, miR-1, miR-100, miR-10a, miR-10b, miR-340, miR-155, miR-15b, miR-186, miR-222, miR-182, miR-210, miR-193b, miR-26a, miR-27a, miR-29a, miR-27b, miR-200c, miR-29c, miR-424, and miR-141, in breast cancer cells of the subject by:
   a) administering to the subject an effective amount of one or more nanosensors of paragraph 1-21 to thereby contact breast cancer cells of the subject, wherein the nanosensor comprises a sensor oligonucleotide specific for the one or more miRNAs;
   b) detecting fluorescence emitted from the one or more nanosensors;
   c) comparing the fluorescence detected with that of a control cell to thereby assess the activity of the target miRNA(s) to a cell; and
   d) identifying target cells which have high activity compared to a control cell of at least miR-10b and miR155, and have low activity of at least one or more of miR200c, miR-141 and miR-31, as metastatic or pro-metastatic.

39. The method of paragraph 38 further comprising determining and recording the location of the target cell within the subject based on the location of the nanosensor and/or the location of the emitted fluorescence by performing nuclear magnetic resonance (NMR) imaging and/or optical imaging.

40. The method of any one of paragraphs 38 or 39, further comprising treating the subject aggressively if metastatic or pro-metastatic cells are identified.

41. A sensor oligonucleotide comprising:
   a) a seed region comprising a nucleic acid sequence that is completely complementary to the target miRNA and comprises a cleavage site which can be engaged and cleaved by the target miRNA;
   b) two non-seed regions that each flank the seed region and are each comprised of a nucleic acid sequence that is complementary to the target miRNA to promote hybridization of the sensor oligonucleotide to the target miRNA; and
   c) members of a quencher-fluorophore pair;
   wherein the quencher fluorophore pair members respectively flank the cleavage site and are separated by a distance that permits significant quenching of emitted fluorescent signal.

42. The sensor oligonucleotide of paragraph 41, that has a nucleic acid sequence that is completely complementary to the target miRNA sequence.

43. The sensor oligonucleotide of any one of paragraphs 41-42, that comprises RNA, or a combination of RNA and one or more other nucleic acid-like polymers that hybridize with RNA in a sequence dependent manner, wherein at least the entire seed region is RNA.

44. The sensor oligonucleotide of paragraph 43, wherein the other nucleic acid-like polymer is DNA, LNA or a 2-0-Me/phosphorothioate backbone.

45. The sensor oligonucleotide of any one of paragraphs 41-44, that is from about 18 to about 30 nucleotides in length.

46. The sensor oligonucleotide of any one of paragraphs 41-45 that is about 20-25 nucleotides in length.

47. The sensor oligonucleotide of any one of paragraphs 41-46, wherein the quencher-fluorophore pair members are separated by a distance of about 9 to about 30 nucleotides.

48. The sensor oligonucleotide of any one of paragraphs 41-47, wherein the fluorophore of the quencher-fluorophore pair is selected from the group consisting of AlexaFluor® 594, AlexaFluor® 647, IRDye®-700DX, AlexaFluor® 750, IRDye®-800, FITC, Cy3®, and DyLight®594.

49. The sensor oligonucleotide of any one of paragraphs 41-48, wherein the fluorophore of the quencher-fluorophore pair has an emission maximal over 600 nm.

50. The sensor oligonucleotide of any one of paragraphs 41-49, wherein the quencher-fluorophore pair is Iowa Black Hole RQ® quencher and Cy5® fluorophore, or IRDye®-700DX-QC-1.

51. The sensor oligonucleotide of any one of paragraphs 41-50, wherein the target miRNA is selected from the group consisting of let-7a, let-7d, let-7c, let-7i, miR-1, miR-100, miR-10a, miR-10b, miR-340, miR-155, miR-15b, miR-186, miR-222, miR-182, miR-210, miR-193b, miR-26a, miR-27a, miR-29a, miR-27b, miR-200c, miR-29c, miR-424, and miR-141.

52. The sensor oligonucleotide of any one of paragraphs 41-54, further comprising a targeting ligand covalently attached to the polymer.

53. The sensor oligonucleotide of paragraph 52, wherein the targeting ligand is a peptide specific for an internalizing receptor located on the exterior plasma membrane of the target cell.

54. The sensor oligonucleotide of any one of paragraphs 52-53, wherein the targeting ligand is selected from the group consisting of RGD, folic acid, peptide EPPT (SEQ ID NO: 11), polyarginine peptide (MPAP), and chlorotoxin.

55. A method for in vivo profiling of miRNA(s) of one or more target cells in a subject comprising,
    a) delivering to the target cell(s) an effective amount of one or more sensor oligonucleotides of any one of paragraphs 41-54;
    b) quantitatively detecting in the subject fluorescence emitted from the sensor oligonucleotides in the target cell(s) to thereby determine the activity of target miRNAs in the target cells of the subject; and
    c) generating a profile from the activity of each target miRNA in each target cell or population thereof from the activity determined in step b).

56. A method for assessing the activity of one or more target miRNA in a target cell comprising,
    a) delivering to the target cell an effective amount of one or more sensor oligonucleotides of any one of paragraphs 41-54;
    b) detecting fluorescence emitted from the one or more sensor oligonucleotides; and
    c) comparing the fluorescence detected with that of a normal control cell to thereby assess if the activity of the target miRNA(s) is high, low or normal in the target cell.

57. The method of any one of paragraphs 55 or 56 further comprising comparing the fluorescence detected for each target miRNA with that of normal control cells to thereby generate a profile of each target miRNA in the target cell or population thereof as deviated from normal.

58. The method of any one of paragraphs 55-57, wherein the steps are repeated periodically to thereby monitor progression of the miRNA activity in the target cells over time.

59. The method of paragraph 56, wherein the target cell is in vivo.

60. The method of paragraph 56, wherein the target cell is in vitro.

61. The method of any one of paragraphs 55-60, wherein the sensor oligonucleotides are delivered or administered to thereby produce an intracellular concentration in the target cell of about 250 nM.

62. The method of any one of paragraphs 55-61 wherein the target cell is of a primary tumor, of a metastatic tumor, of a biopsy, virally infected, parasitically infected, or non-infected pathology.

63. The method of any one of paragraphs 55-61, wherein the one or more miRNA is one or more of miRNAs selected from the group consisting of let-7a, let-7d, let-7c, let-7i, miR-1, miR-100, miR-10a, miR-10b, miR-340, miR-155, miR-15b, miR-186, miR-222, miR-182, miR-210, miR-193b, miR-26a, miR-27a, miR-29a, miR-27b, miR-200c, miR-29c, miR-424, and miR-141.

64. The method of any one of paragraphs 55-62, wherein the one or more miRNA comprises miR-10b, miR-155, miR-200C, miR-141, or combinations thereof.

65. The method of any one of paragraphs 56-64, wherein the target cell is in vivo and delivery is by administration to a subject comprising the target cell.

66. The method any one of paragraphs 55-65, wherein administration is by injection.

67. The method of any one of paragraphs 22-37, and 55-65, wherein delivering or administering is by intratumoral injection, transfection, or titration/incubation.

68. A method of detecting metastatic or pro-metastatic breast cancer cells in a subject comprising, assessing the activity of one or more miRNAs selected from the group consisting of let-7a, let-7d, let-7c, let-7i, miR-1, miR-100, miR-10a, miR-10b, miR-340, miR-155, miR-15b, miR-186, miR-222, miR-182, miR-210, miR-193b, miR-26a, miR-27a, miR-29a, miR-27b, miR-200c, miR-29c, miR-424, and miR-141, in breast cancer cells of the subject by:
    a) administering to the subject an effective amount of one or more sensor oligonucleotides of any one of paragraphs 41-54 to thereby contact breast cancer cells of the subject, wherein the sensor oligonucleotide is specific for the one or more miRNAs;
    b) detecting fluorescence emitted from the one or more sensor oligonucleotides;
    c) comparing the fluorescence detected with that of a control cell to thereby assess the activity of the target miRNA(s) to a cell; and
    d) identifying target cells which have high activity compared to a control cell of at least miR-10b and miR155, and have low activity of at least one or more of miR200c, miR-141 and miR-31, as metastatic or pro-metastatic.

69. The method of paragraph 68, wherein administration is by intratumoral injection.

70. The method of any one of paragraphs 68-69 further comprising determining and recording the location of the target cell within the subject based on the location of the emitted fluorescence by performing optical imaging.

71. The method of any one of paragraphs 68 or 70, further comprising treating the subject aggressively if metastatic or pro-metastatic cells are identified.

The invention is further illustrated by the following examples, which should not be construed as further limiting.

EXAMPLES

Example 1—Development of Nanosensors

The following experiments were performed in order to develop nanosensors that are capable of noninvasively identifying miRNA signatures characteristic of metastatic breast cancer. The approach taken was highly multidisciplinary and drew upon multiple fields, including bioinformatics, molecular biology, nanoparticle engineering, and noninvasive imaging. In the course of the project, miRNAs reflective of breast cancer metastasis were identified and will be further confirmed, with additional miRNA's being identified utilizing bioinformatics and gene expression analysis to obtain a set of candidate miRNAs whose differential expression in primary tumors and metastases is linked to the metastatic phenotype. Further, a design for nanoparticle-based diagnostic nanosensors was proposed for the noninvasive detection of metastatic microRNA signatures. The proposed nanosensors have two core components: a) a magnetic nanoparticle (MN) component that accumulates in primary tumor cells and lymph node metastases and serve as an MRI-guided delivery vehicle; and b) a component consisting of multiple sensor oligos complementary to target miRNA and attached to the nanoparticle surface; this component can be detected by optical imaging methods.

MRI has been used to monitor nanoparticle uptake by target tissues in a semi-quantitative manner, as described in preliminary results and prior publications[26,27]. The miRNA detection component consists of oligos modified with a quencher-fluorophore pair that serve as a substrate for target miRNA. Cleavage of the substrate oligo by the cognate miRNA leads to de-quenching and a fluorescent turn-on. This quenching-dequenching mechanism of detection is well-established in vivo[28-30].

The significance of the approach is in the capacity to non-invasively detect miRNA activity in vivo. This new capability can identify novel metastatic phenotypes and gene regulatory networks in cancer, increase the understanding of miRNA function in cancer and metastasis, identify miRNA signatures of metastasis in the in vivo setting; and provide a new target validation strategy for therapeutic development, and possibly a diagnostic approach.

The magnetic nanoparticles are already in clinical use, including for lymph node detection and staging of breast cancer patients[31, 32]. This modification of the previously developed technology is applicable to the clinical setting. The clinical feasibility of the method is underscored further by the fact that optical imaging methods have already been applied for clinical breast imaging[33-36]. In addition, one can envision a utility for the method using MRI guided laparoscopic or intraoperative diagnostics.

This technology will provide new information about epigenetic signatures of breast cancer metastasis. It will establish a new methodology for differentiating between the metastatic and nonmetastatic phenotype. Based on these studies, one can envision the design of clinical tests that use biopsy or serum samples and focus on the differentially expressed miRNAs identified herein. This test can be employed to diagnose the presence of metastatic disease or to inform therapy. It also can be used for noninvasive in vivo profiling of microRNA signatures.

The only reports of in vivo miRNA detection have recently emerged from a group in Korea, which uses molecular beacon technology[37,38]. These studies support the feasibility of imaging miRNA availability in vivo. However the molecular beacon technology suffers from low signal-to-background ratios, making quantitative interpretation of signal intensity problematic. Besides these studies, the currently established methods for microRNA detection in situ rely on PCR and northern blotting, or high-affinity hybridization probes[39-51]. One drawback of the presently available methods is that they are only applicable in vitro. Consequently, these methods do not permit longitudinal studies, in which the "evolution" of the metastatic phenotype is monitored in an intact physiologic environment. Another drawback is that they rely on hybridization, and so report on miRNA availability but not on miRNA activity. Another drawback of the currently established methods is that they rely on direct hybridization of the sensor oligo to the miRNA, reflecting a 1:1 ratio of fluorescent probe per miRNA.

Use of the nanoparticle-based diagnostic nanosensors produces increased sensitivity over the molecular beacon technology, since it does not rely on hybridization between the miRNA and mRNA but on catalytic cleavage of the target probe by the miRNA. It is also amenable to in vivo detection. It also reports directly on miRNA activity because it relies on cleavage of the substrate by the miRNA, i.e. on its catalytic properties. Another advantage is that this technology employs a powerful signal amplification strategy. Namely each cell can take up over $1 \times 10^6$ nanoparticles with attached sensor oligos.[52] Each miRNA cleaves its substrate catalytically, leading to powerful signal amplification resulting from the cleavage of millions of synthetic substrates on the nanoparticles by the cognate miRNA.

Experimental Strategy

Figure 1B:
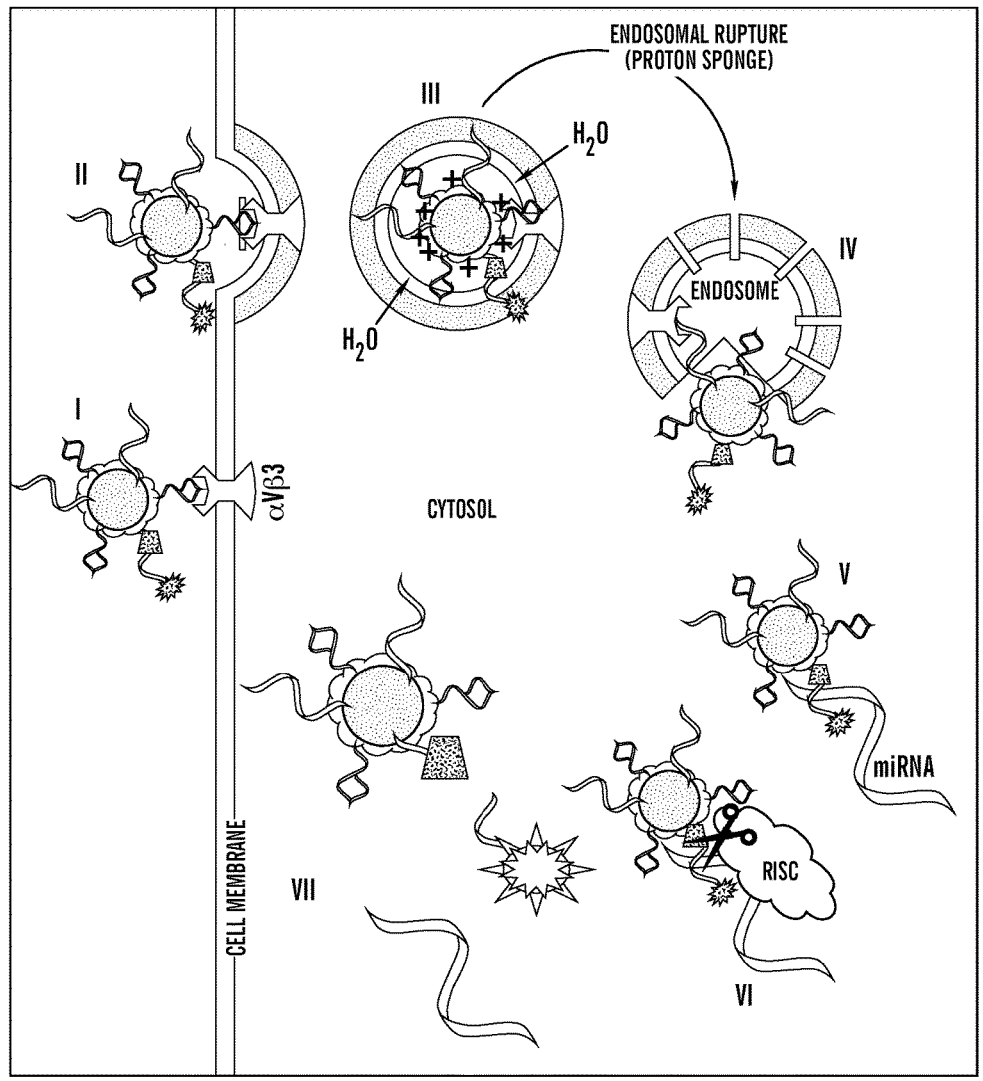

The development of the nanosensors and methods of their use is based on the findings reported herein and prior publications[53,54]. Specifically, nanoparticles were developed that accumulate in primary and metastatic tumor cells, following intravenous injection. Upon internalization of the nanoparticles by the cell, the nanoparticles efficiently engage the endogenous cytosolic RNA interference apparatus in a sequence-specific way. The nanoparticles consist of dextran-coated iron oxide crystals (MN, 25-30 nm in diameter), conjugated to peptide ligands (cRGD) that are targeted to internalizing receptors ($\alpha v \beta 3$) on the tumor cells, and sensor oligos complementary to endogenous miRNA species (FIG. 1A). These sensor oligonucleotides are composed of RNA bases, are cleavable (non-stabilized by chemical modification) around the seed region (the conserved region within which the microRNA engages the RNA substrate), and are labeled with a fluorescent dye-quencher pair, so that upon cleavage of the oligonucleotide by the microRNA, there is a fluorescent turn-on (FIG. 1A). The mechanism is described in FIG. 1B. Namely, the cRGD-labeled nanoparticles are recognized (FIG. 1BI) and engaged (FIG. 1BII) by the internalizing $\alpha v \beta 3$ receptor on tumor cells and localize to endosomes (FIG. 1BIII). Inside the endosomes, the functionalized nanoparticles rich in unsaturated amines mediate the proton sponge effect by sequestering protons that are supplied by the v-ATPase (proton pump). This process keeps the pump functioning and leads to the retention of one Cl⁻ ion and one water molecule per proton. Subsequent endosomal swelling and rupture leads to particle deposition in the cytoplasm (FIG. 1BIV). In the cytosol, the nanoparticles, which carry multiple copies of a sensor oligo complementary to an endogenous microRNA species, bind the microRNA (FIG. 1BV), leading to the recruitment to the duplex of the endogenous RNA induced silencing complex (RISC) and cleavage of the oligo at a specific position in the seed region (FIG. 1BVI). This cleavage results in separation between the quencher and dye located at the ends of the sensor oligo and a fluorescent turn-on. The microRNA is released from the complex and is free to catalyze subsequent cleavage reactions (FIG. 1BVII). The described mechanism exploits the endogenous process of RNA interference, which is invariably triggered by the presence of cytosolic single-stranded RNA oligonucleotides that are complementary to an endogenous microRNA. This proposed approach also takes advantage of powerful signal amplification, since millions of nanoparticles/oligos are delivered per cell, using the delivery method developed by the inventors.

Results
Pro-Metastatic miRNAs are Differentially Expressed in the Primary Tumor and Metastases.

miRNA signatures in the primary tumor compared with those in lymph node metastases can identify differentially expressed miRNAs. The hypothesis is that the differential miRNA signature specific to the lymph node metastases are indicative of the pro-metastatic phenotype, since the lymph nodes represent the primary depot for tumor cells en route to distant organs.

Prior research has identified miRNA-10b as a key pro-metastatic agent in human breast cancer[55]. It was desired to first test if that is true in the proposed animal model, i.e. female nude mice injected in the fat pad with the human breast adenocarcinoma MDA-MB-231-luc-D3H2LN cell line (Caliper Life Sciences, Hopkinton, Mass.). These animals form tumors by 2 weeks after inoculation and metastases to lymph nodes by 4 weeks after tumor inoculation. This model reflects stages of lymph node metastatic breast cancer and is compatible with fluorescence optical imaging (nude mice). Furthermore, transcriptional profiling of primary tumors and metastases derived from orthotopic models of human cancer represents a validated method of identifying pro-metastatic signatures[56].

Small RNA was isolated from the primary tumor and lymph node metastases of tumor-bearing mice, and the expression of miRNA-10b was analyzed. It was observed that a very significant 177-fold up-regulation of miRNA-10b in the lymph node metastases relative to the primary tumor ($p<0.001$, $n=3$).

To identify additional miRNAs relevant to metastasis, global microarray analysis was performed to compare the primary tumors and lymph node metastases of the MDA-MB-231-luc-D3H2LN orthotopic mouse model. SABiosciences qPCR arrays was used (SABiosciences, Frederick, Md.). 13 miRNAs were identified as significantly overexpressed and 11 as downregulated in the lymph node metastases relative to the primary tumor (FIG. 2). Of these, miR10b, 155, 200c, and 141 are known mediators of breast cancer metastasis[60]. The relevance of these miRNAs to tumor cell invasion and migration and the differential expression in clinical samples will be further verified by the experiments described herein.

Tumor-Targeted Nano-Delivery of Oligonucleotides Targets the microRNA Machinery in Tumor Cells.

Figure 3A:
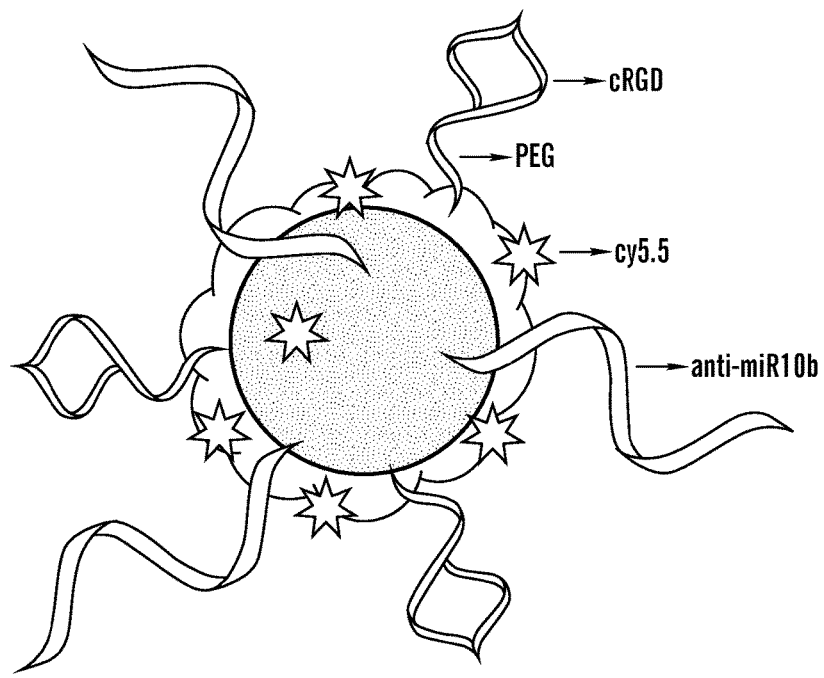
FIG. 3A-FIG. 3D shows experimental results performed to test the MN-anti-miR10b.
Figure 3B:
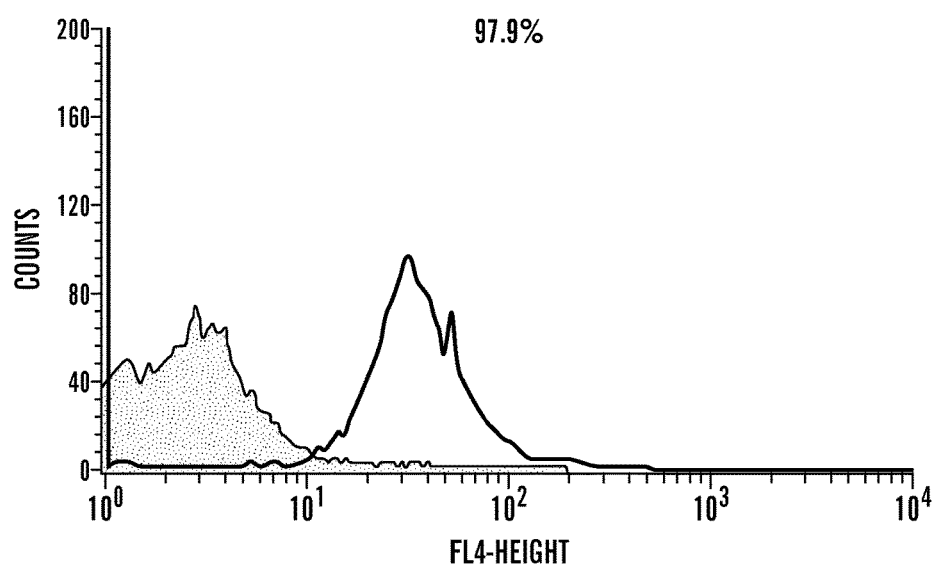
Figure 3C:
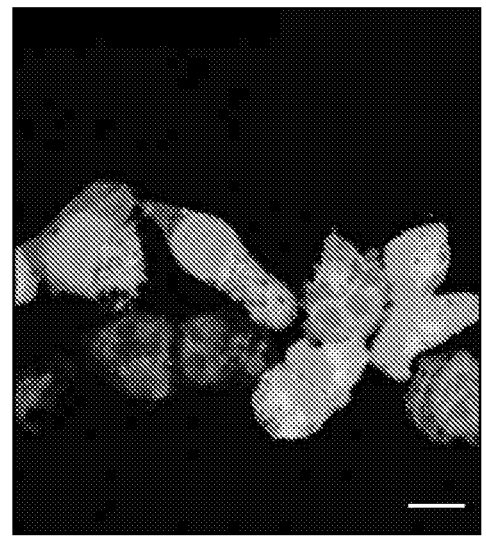
Figure 3D:
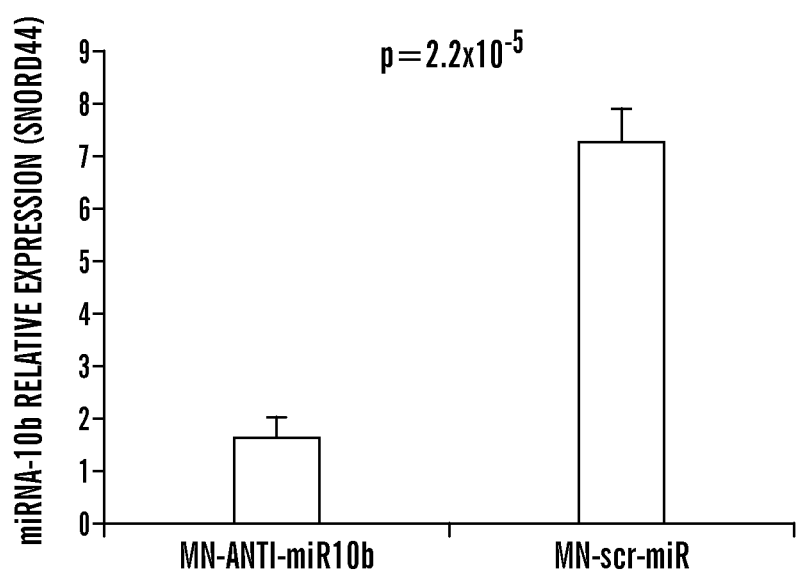

Having in mind the key role played by miRNAs in tumor metastasis, an approach was developed to target selected tumor cell miRNAs for imaging and therapeutic purposes. Dextran coated magnetic nanoparticles (MN) were labeled with the fluorescent dye, Cy5.5, and conjugated to a tumor-targeting peptide (RGD, targeting the $\alpha v \beta 3$ integrin). The nanoparticles were functionalized with Cy3-labeled knock-down locked-nucleic acid oligos (LNA, Exiqon, Woburn, Mass.) targeting human miRNA-10b[55] (MN-anti-miR10b; FIG. 3A). The LNA design used in these preliminary studies protects the oligos from cleavage by nucleases and miRNAs. Once bound to miRNA, the LNA inhibits its target by forming a stable heteroduplex. MN-anti-miR10b was taken up extensively by human MDA-MB-231(gfp) cells (FIGS. 3B and C). This uptake resulted in a remarkable 87.8±6.2% knock-down of the target miRNA-10b (FIG. 3D). These results indicate that the proposed method can efficiently deliver oligos to tumor cells in a way that accesses and engages the miRNA machinery.

Magnetic Nanoparticles can Deliver Oligonucleotides to Tumors and Lymph Node Metastasis In Vivo in a Target-Specific Manner.

Figure 4A:
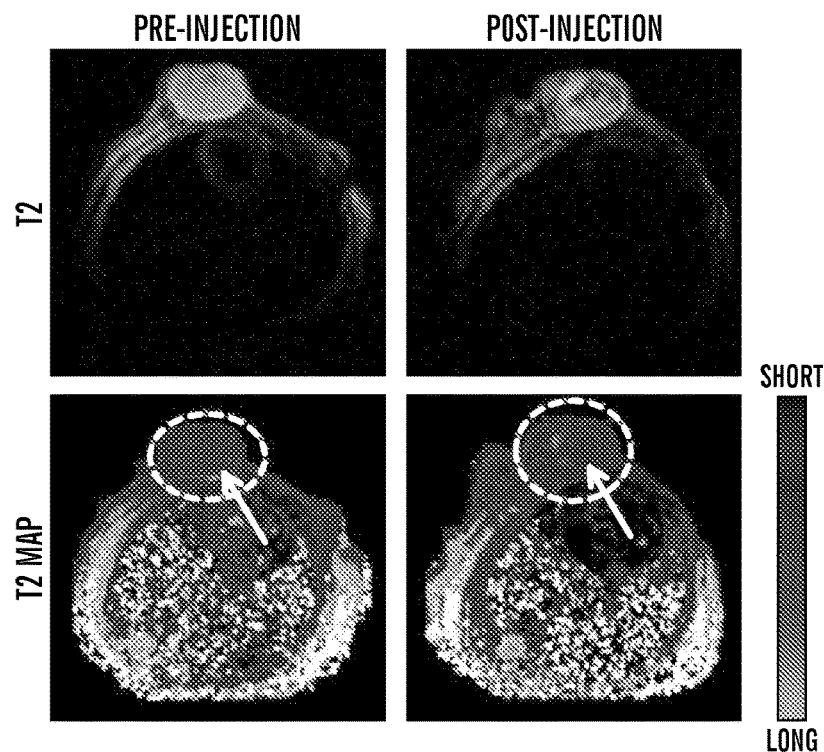
FIG. 4A-FIG. 4B shows experimental results of MRI performed to quantify in vivo tumor uptake of MN-anti-miR10b in breast tumor bearing mice.
Figure 4B:
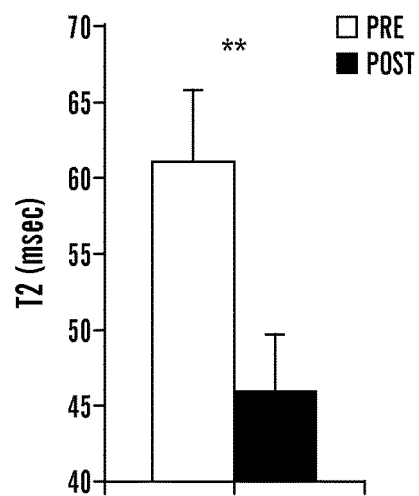
Figure 5A:
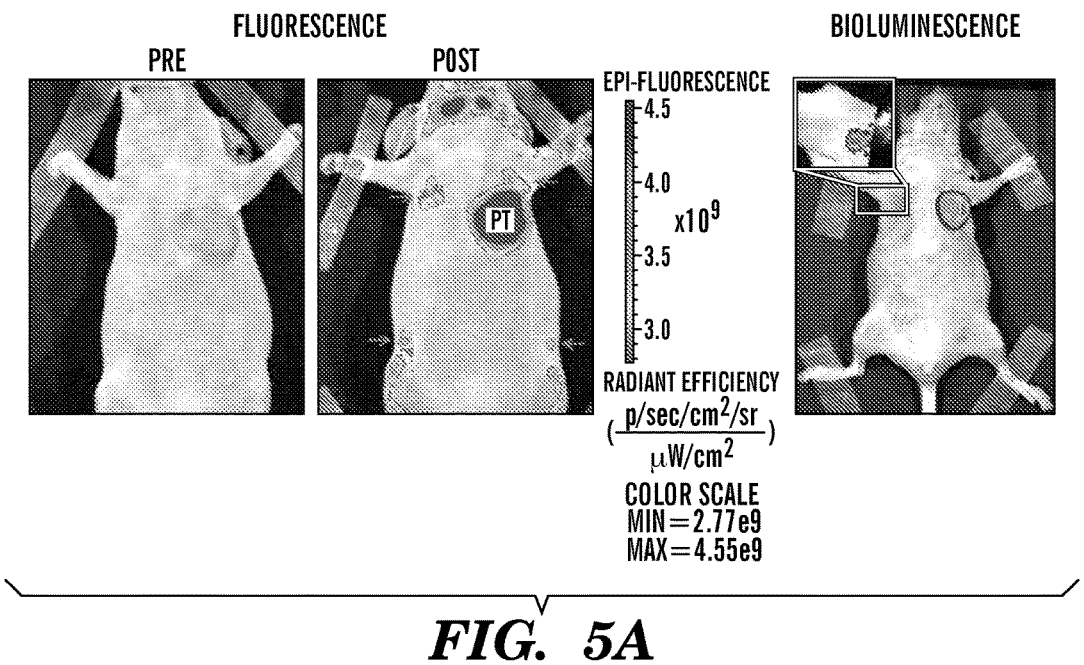
FIG. 5A-FIG. 5E shows experimental results that show NIR optical imaging of MN-anti-miR10b accumulation in orthotopic MDA-MB-231-luc-D3H2LN tumors.
Figure 5B:
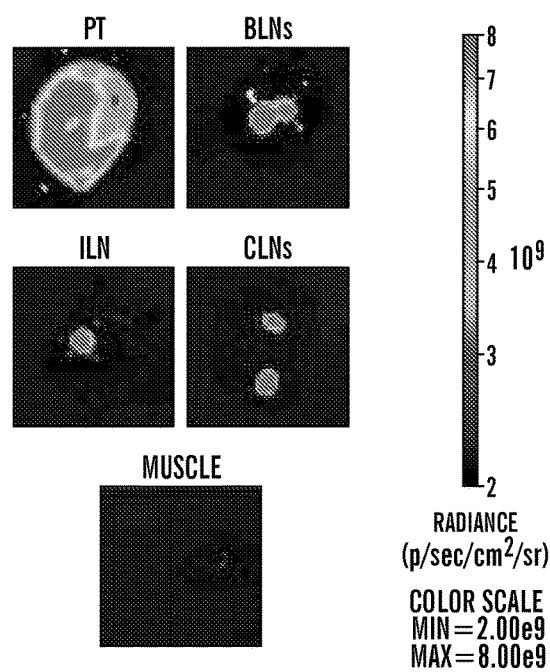
Figure 5C:
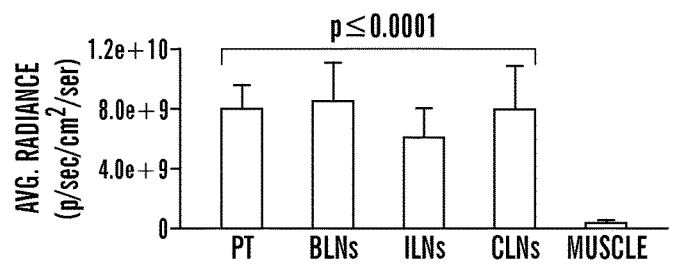
Figure 5D:
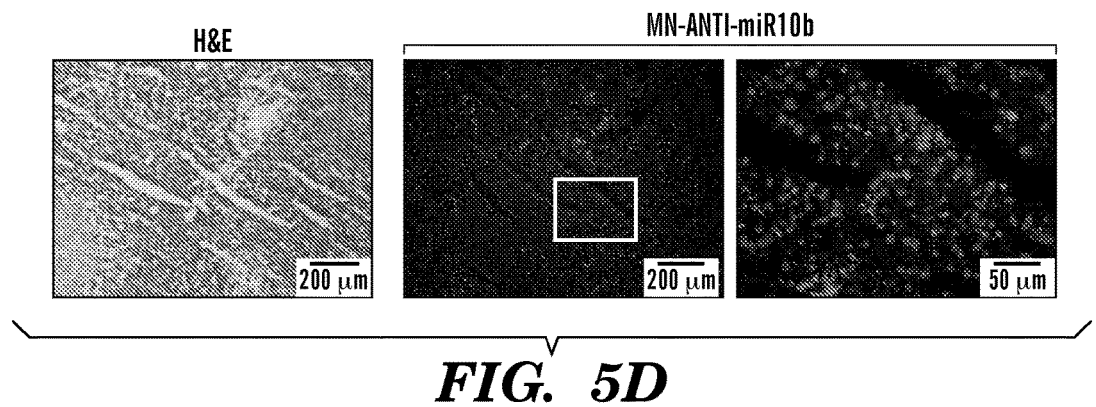

Since the nanosensor was intended to noninvasively profile changes in miRNA expression as tumor cells progress from a localized to a metastatic phenotype, it needed to be determined if MN-coupled oligos could be delivered both to the primary tumor and metastatic tumor cells in vivo. Pilot experiments were performed in nude mice orthotopically injected with luciferase-expressing MDA-MB-231-luc-D3H2LN tumor cells. MN-anti-miR10b were injected intravenously into tumor-bearing animals. The delivery of the nanoparticles was monitored by MRI as described previously[26]. Accumulation of MN-anti-miR10b in the tumor was observed (FIG. 4A), which was reflected by a significant T2 shortening FIG. 4B, $p<0.05$, $n=6$). Near-infrared optical imaging was performed to study the whole-body bioavailability of the Cy5.5-labeled MN-anti-miR10b. As shown in FIG. 5A, nanoparticles were delivered to the primary tumor and lymph nodes. This delivery was confirmed by ex vivo imaging (FIG. 5B) and was significantly higher than the reference muscle tissue (FIG. 5C). Microscopy of frozen tumor sections in the Cy5.5 channel revealed extensive uptake by the tumor cells (FIG. 5D).

Figure 5E:
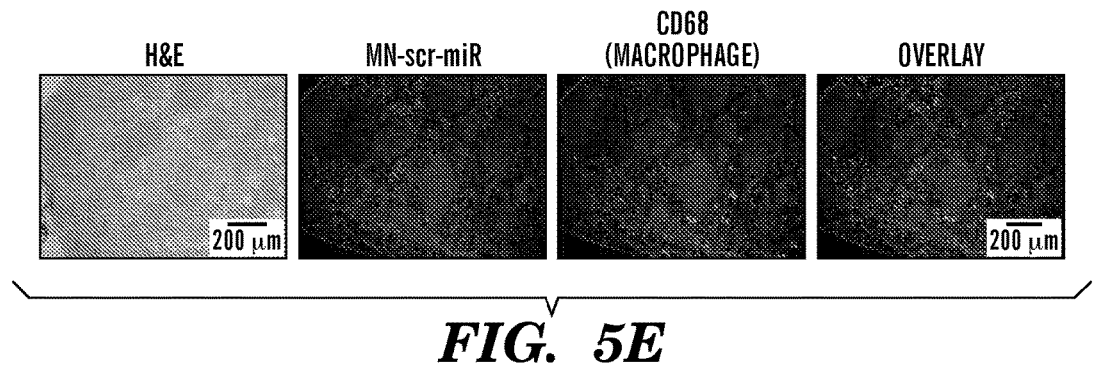

A key question to address was whether functionalizing the probe with RGD peptides accomplished uptake of the nanoparticles by metastatic tumor cells inside lymph nodes. Since MN-anti-miR10b prevents the formation of lymph node metastasis (discussed directly below), MN-scr-miR was used (scrambled oligo that permits the formation of lymph node metastases) in this study. Histological analysis of lymph nodes from tumor-bearing animals showed that after injection MN-scr-miR localized not only in lymph-node resident macrophages but also extensively in metastatic tumor cells (FIG. 5E). This finding indicates that the nanosensors will achieve a mechanical targeting to the lymph nodes through the lymphotropic nature of the nanoparticles, and a molecular targeting to the tumor cells inside lymph nodes through the RGD peptide.

Tumor-Targeted Delivery of Oligonucleotides by Nanoparticles can Access and Engage the miRNA Machinery In Vivo.

Figure 6A:
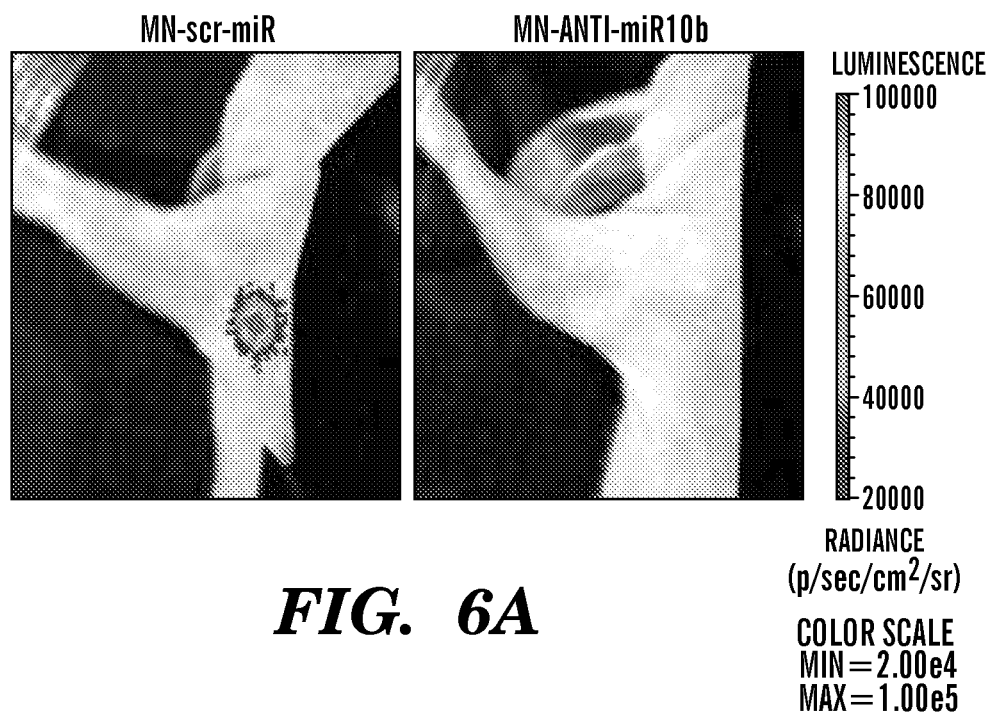
FIG. 6A-FIG. 6F shows experimental results that indicate the prevention of lymph node metastasis by MN-anti-miR10b.
Figure 6B:
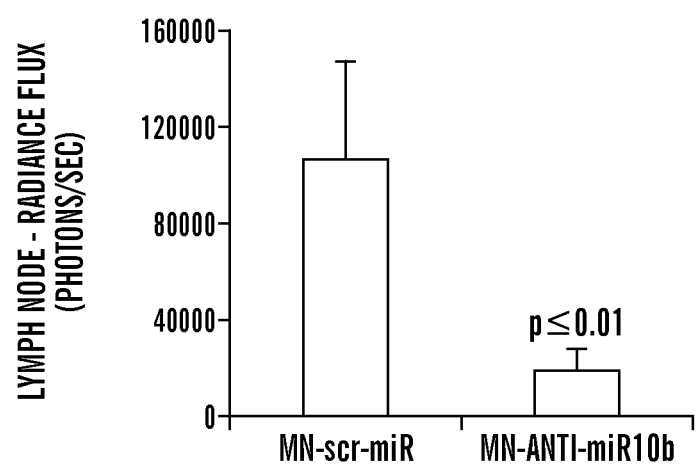
Figure 6C:
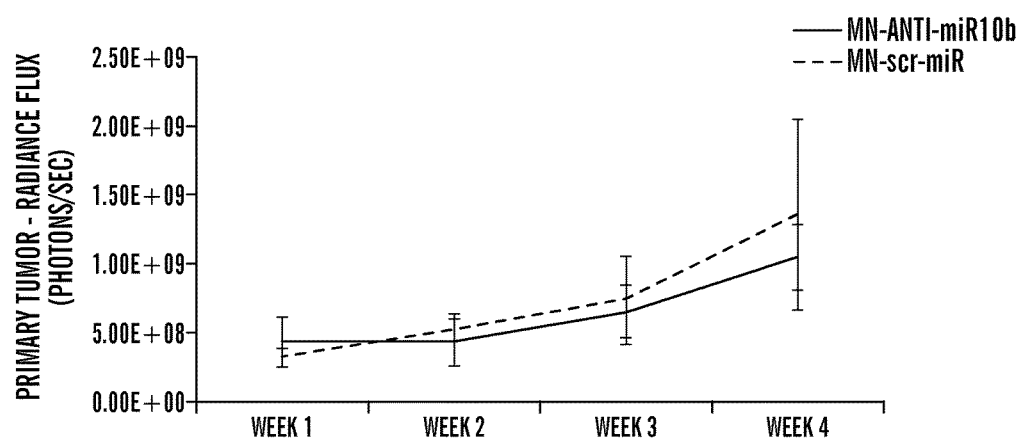
Figure 6D:
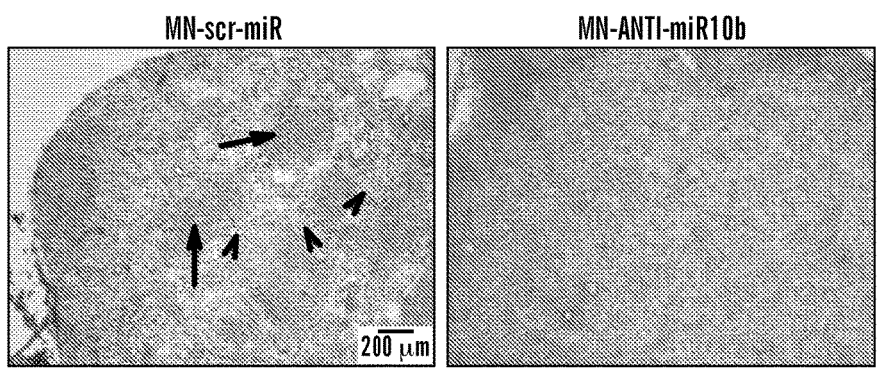
Figure 6E:
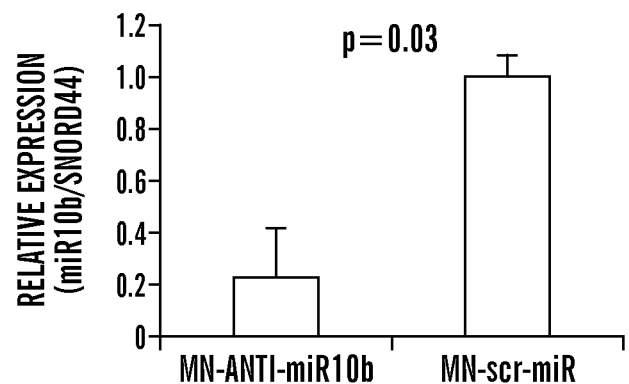
Figure 6F:
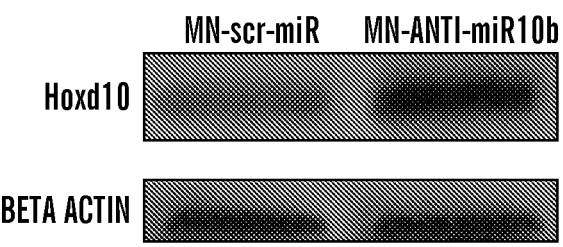

To assess the feasibility of accessing the miRNA machinery after in vivo delivery, MN-anti-miR10b was intravenously injected in nude mice orthotopically implanted with the luciferase-expressing MDA-MB-231-luc-D3H2LN cell line ($n=12$). Treatment was initiated at two weeks after tumor implantation, prior to the formation of detectable lymph node metastases, and involved tail vein injections (10 mg/kg of iron) delivered once a week for four weeks. In vivo bioluminescence imaging was performed during each treatment to visualize and quantify primary and metastatic burden from the luciferase-expressing cell line. It revealed that by the end of the treatment course, the signal in the lymph nodes of experimental animals treated with MN-anti-miR10b was at pre-metastatic levels, indicating a prevention of metastasis from the primary tumor to lymph nodes (FIG. 6A). In contrast, there was visible dissemination of tumor cells to the lymph nodes of control animals treated with the MN-scr-miR. The therapeutic effect on metastatic burden was highly significant ($p<0.01$, FIG. 6B) and occurred without a concomitant difference in primary tumor size between experimental and control animals (FIG. 6C). Histopathological analysis of the lymph nodes confirmed the absence of detectable metastases in animals treated with MN-anti-miR10b. Conversely, there was extensive invasion of the lymph nodes by tumor cells in control animals (MN-scr-miR) accompanied by a disruption of lymph node architecture and the formation of reverse follicles (FIG. 6D). This therapeutic effect was reflected, as expected, by a significant inhibition of miR-10b in the primary tumors (qRT-PCR; p=0.03; FIG. 6E) and an induction of the miR-10b target, HOXD10 (Western blot; FIG. 6F)[55]. This result confirmed that oligonucleotides delivered by magnetic nanoparticles could access and engage the miRNA machinery in a sequence-specific way, using simple intravenous injection.

The Sensor Oligo Design can Report on Individual miRNA Activity with a High Sensitivity and Specificity and is Applicable In Vivo.

Finally, to assess the feasibility of the proposed approach, a small pilot study was performed in which a cleavable sensor oligo to detect miR-10b activity was designed. The oligo was identical to the knock-down anti-miR10b, described above, except that the miR10b antisense oligonucleotide (non-cleavable LNA oligo) was replaced with a miR10b sensitive oligonucleotide (cleavable RNA oligo).

Figure 7:
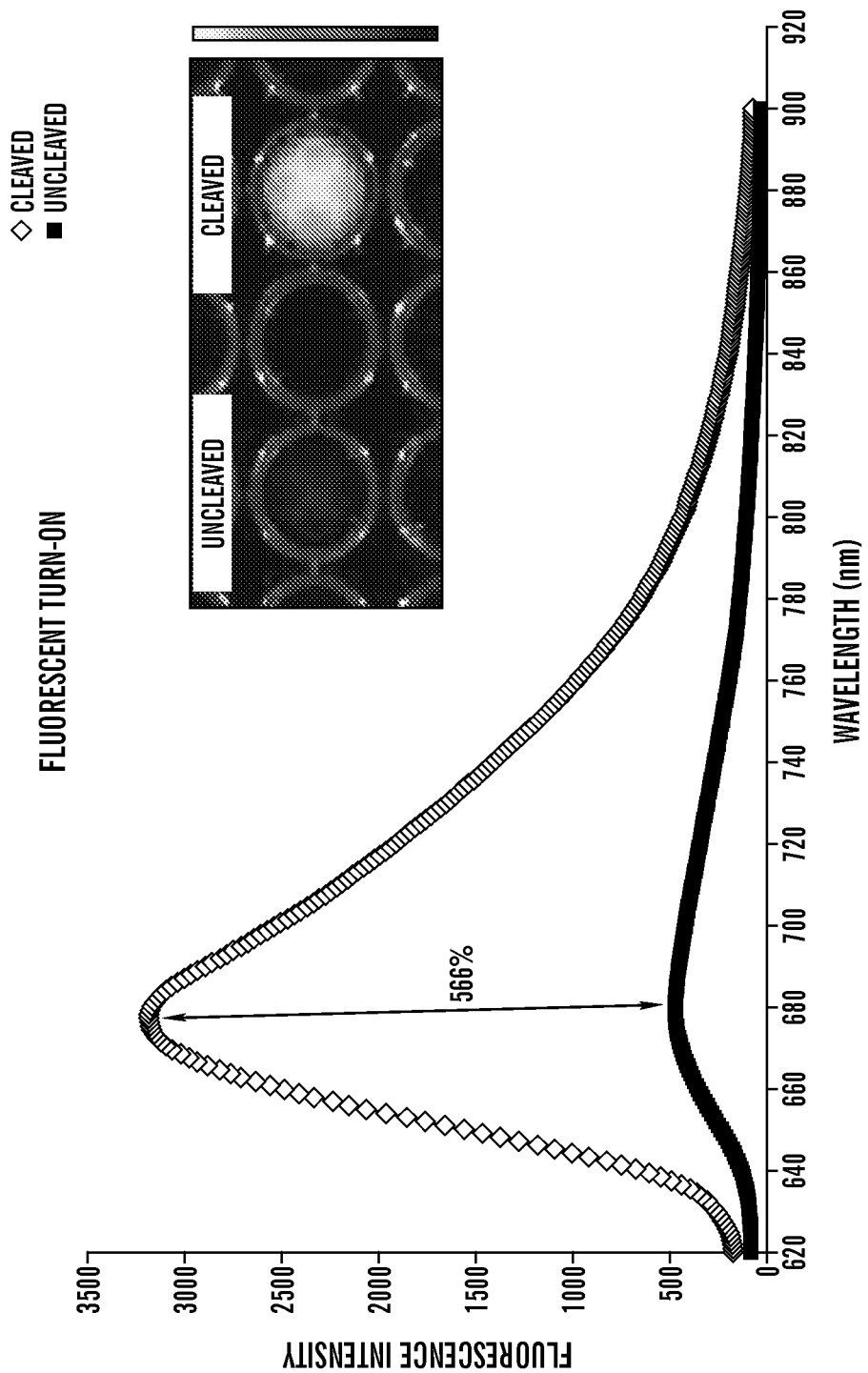
FIG. 7 shows experimental results that indicate signal-to-background ratio for the miR-10b sensor. Cleavage of the oligo by RNase resulted in a 566% fluorescence enhancement over the noncleaved oligo incubated in RNase-free conditions.

The sequence of the RNA-based sensor oligo was: AC AAA UUC GGU UCU ACA GGG UA (SEQ ID NO: 7). Iowa Black Hole RQ quencher on the 3' end and Cy5 on the 5' end were used as the quencher and dye, respectively. This oligonucleotide is completely complementary to the miRNA. First the signal-to-background ratio was determined by incubating 100 nM of the sensor oligo with a 10 µg/ml of nuclease. As seen in FIG. 7, cleavage of the oligo resulted in a 566% fluorescence enhancement over the noncleaved oligo (RNase-free conditions). In this case, the oligo was terminally labeled with the dye and quencher (as a cost-saving measure). Consequently, the two were separated by 22 nucleotides (7.5 nm). Future experiments can include using a sensor designed to have an internally labeled oligo which has a 10-nucleotide (nt) distance (3.4 nm) between the dye and quencher. This is expected to result in an >95% quenching efficiency.

Next the sensitivity and specificity of detection was determined. A cell-free assay was designed based on previous work[57,58]. This assay relies on the fact that the RISC complex is primed by endogenous miRNA, prior to cell lysis. Addition of the sensor oligo into the lysate results in engagement by the pre-primed miRNA-RISC complex.

Briefly, MDA-MB-231 luc-D3H2LN cells were lysed, as described in previous work[57,58]. The lysates were dispensed into a 96-well plate. Half of the wells were incubated for 30 min. at 37° C. with a 10-fold excess of anti-miR10b LNA antisense oligonucleotides (ASO, Exiqon, Woburn, Mass.) and represented a miR-10b-deleted control.

Figure 8A:
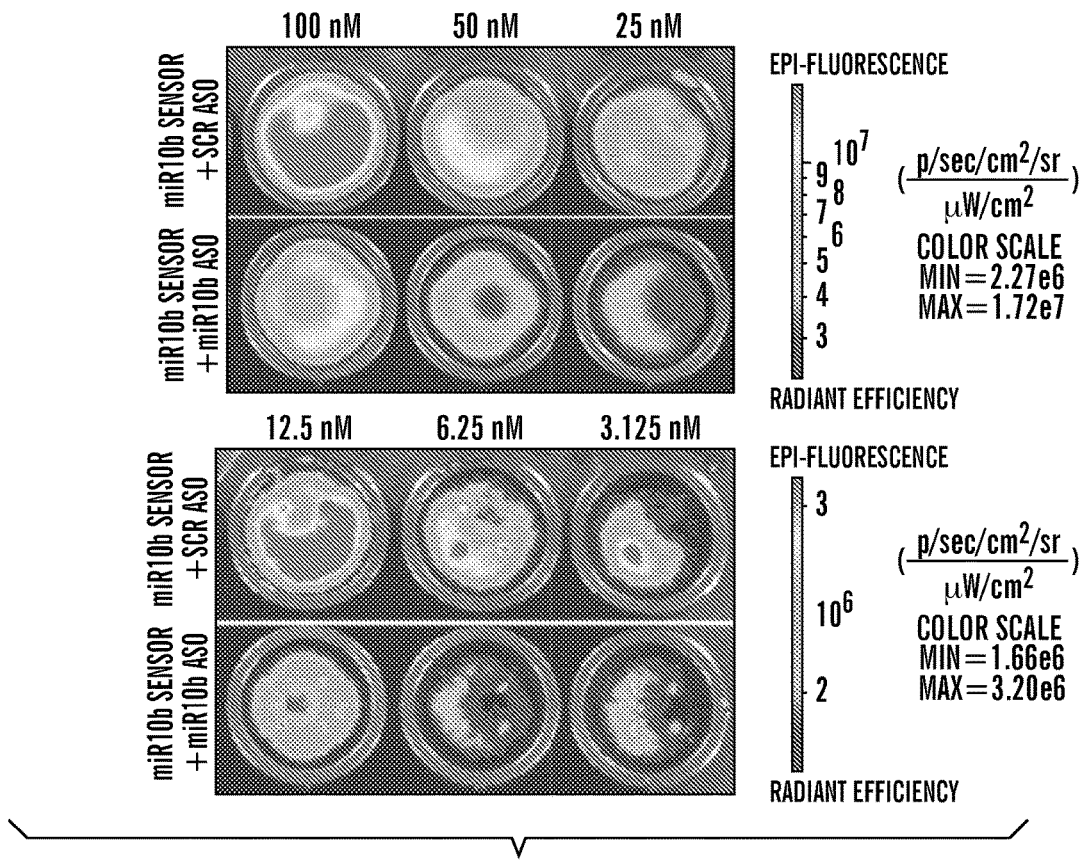
FIG. 8A-FIG. 8C shows experimental results that indicate the in vitro sensitivity and specificity of miR10b detection.
Figure 8B:
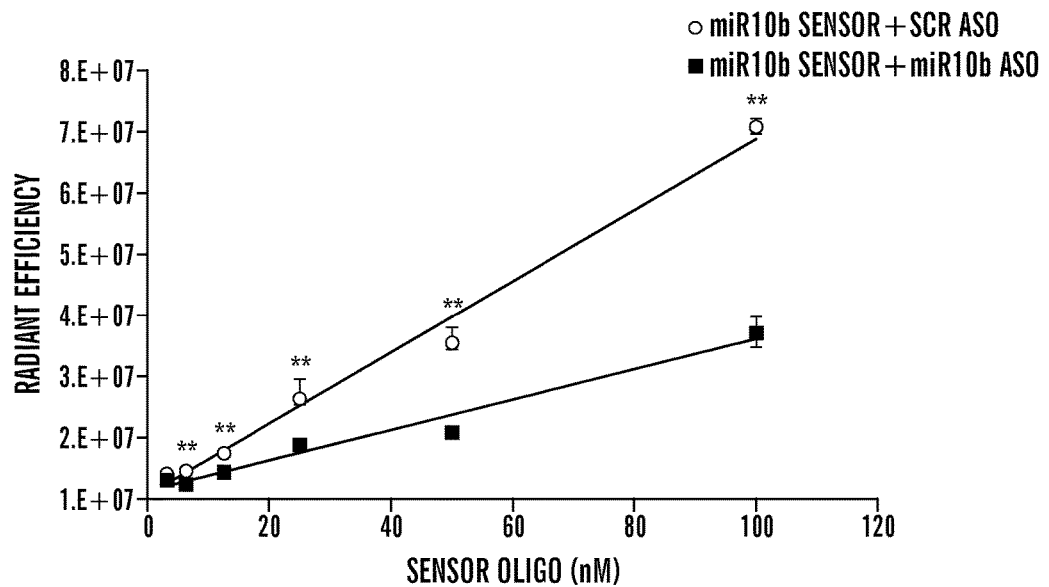

Following, the sensor oligo was titrated into the lysates (100 nM-3.1 nM) and incubated for 2 hrs at 37° C. Finally, the reaction was stopped by the addition of nine volumes of proteinase K buffer (15 min at 37° C.). Fluorescence from the sensor oligo was recorded using the Ivis Spectrum instrument (649 nm excitation; 670 nm emission). As seen in FIG. 8A, there was a distinctive fluorescence enhancement with increased concentration of the sensor oligo. This enhancement was specific for miR-10b, since in the miR-10b deletion control (sensor+miR-10b ASO), the fluorescent signal was lower relative to the treatment group (sensor+SCR ASO). The difference in radiant efficiency was quantified and examined by linear regression analysis (FIG. 8B). The treatment and miR-10b-deletion control groups were significantly different at sensor oligo concentrations ranging from 6.3 to 100 nM (p<0.01, n=3). Using the formula 3(sigma)/slope, a detection limit of 13.4 nM was calculated. However, it is posited that the proposed optimized sensor design will have an even lower limit of detection, because in that design, background fluorescence will be reduced (the rationale is explained in reference to FIG. 7). Regarding the specificity of detection, the assay is highly specific, since the ASO used in the miR-10b deleted control is >99% specific for miR-10b (Exiqon, Woburn, Mass.). The precise level of specificity, can be quantified by testing sensor oligos with 1, 2, or 3-nucleotide mismatches.

Figure 8C:
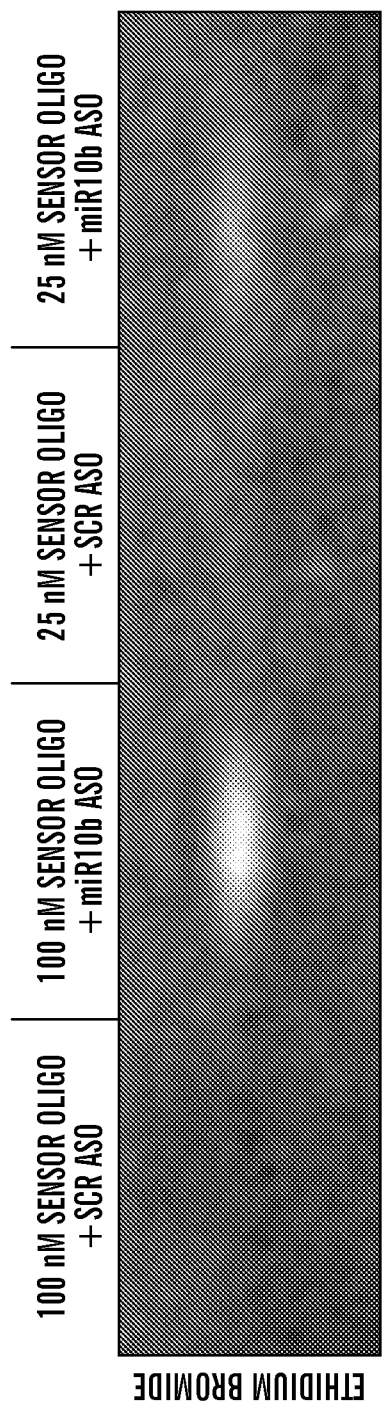

Finally, cleavage of the sensor oligo by miR10b was confirmed by using gel electrophoresis (100 nM and 25 nM are shown but cleavage was confirmed at 50 nM and 12.5 nM as well in a separate experiment). This indicated that the observed fluorescence enhancement is the result of cleavage of the sensor oligo and confirmed that miR-10b cleaves the substrate oligo as designed, despite the fact that it has no known cleavage activity toward any of its known mRNA targets. Electrophoresis was performed as described in prior work[57, 58] (FIG. 8C), using sensor oligo or sensor oligo+ ASO in water as positive controls.

Figure 11A:
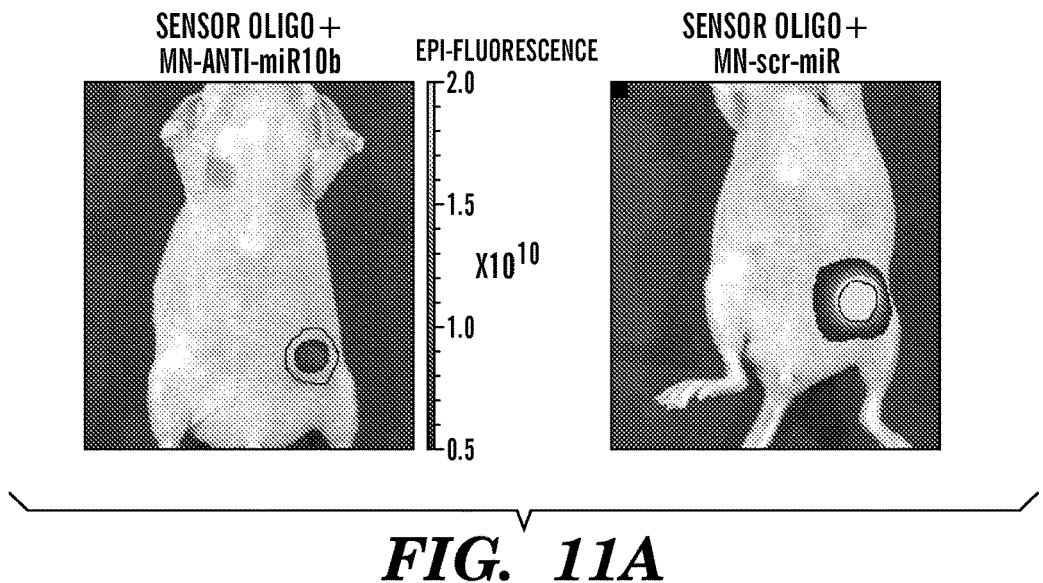
FIG. 11A-FIG. 11C shows experimental results that indicate in vivo detection of miR10b activity using the miR10b-specific sensor oligo.
Figure 11B:
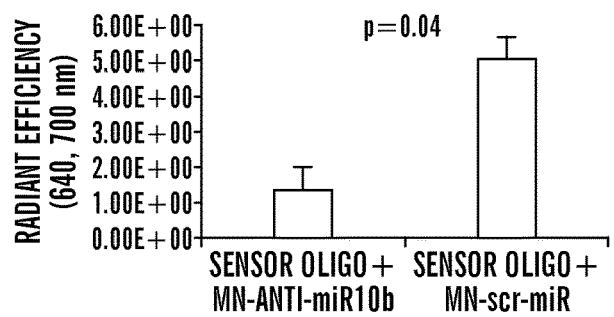
Figure 11C:
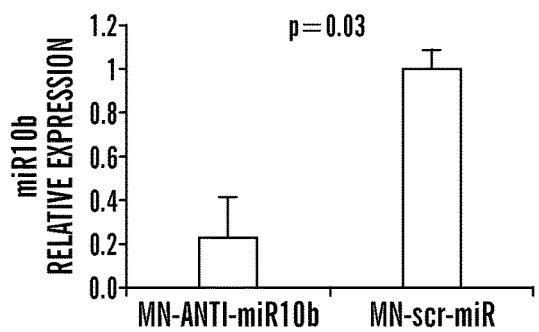

Next the feasibility of detecting miRNA activity in vivo was determined. Animal models were first generated in which miR-10b activity in the tumors was either at wildtype levels or inhibited, as described in sections C3 and C4 of the preliminary results. Namely, nude mice were implanted with MDA-MB-231 luc-D3H2LN cells and 2 weeks later the animals were treated for four weeks with MN-anti-miR10b or MN-scr-miR. Three days after the last treatment, the mice were injected i.t. with the sensor oligo (1 nmole) and then imaged another three days later by in vivo optical imaging (as described in section C3) using filters for the Cy5 dye on the sensor oligo. A clear enhancement of the primary tumor was observed, consistent with cleavage of the sensor oligo, separation of the Cy5 dye from the quencher, and a fluorescent turn-on (FIG. 11A). This effect was specific for miR10b, since in the animals in which miR-10b was inhibited (MN-anti-miR10b), the signal enhancement was noticeably lower than in the animals in which miR-10b was not inhibited (MN-scr-miR) (FIG. 11A). This difference in fluorescence intensity was quantified and found to represent a 74% reduction in radiant efficiency in the miR-10b-inhibited group (FIG. 11B, p<0.05, n=3), despite a lack of difference in tumor size. Furthermore, these results indicated that the method could deliver quantitative information about miR activity, since qRT-PCR revealed a 78% difference in miR-10b expression between the miR-10b-inhibited (MN-anti-miR10b) and control (MN-scr-miR) animals (FIG. 11C). Finally, the results indicate that targets at least 80% less abundant than miR10b (expressed at $⅕^{th}$ of miR10b) can be detected. Of all identified targets only miR-100 and -10a are expressed at less than $⅕^{th}$ of miR-10b demonstrating a 7- and 7.6-fold lower expression. However, these targets are likely co-regulated with miR10b, since they are the other two members of the closely conserved miR100/10 family.

Because of the high-cost of synthesis of the final nanosensor, in these studies intratumoral injection of free oligos was used. However, combined with the proof that nanoparticle-conjugated oligonucleotides can be delivered to tumors and metastatic lymph nodes and the endogenous RNAi machinery can be efficiently engaged (described herein), these findings establish that miRNA signatures can be detected in vivo by replacing the knock-down oligos (C4) with cleavable oligonucleotide sensors.

Figure 10:
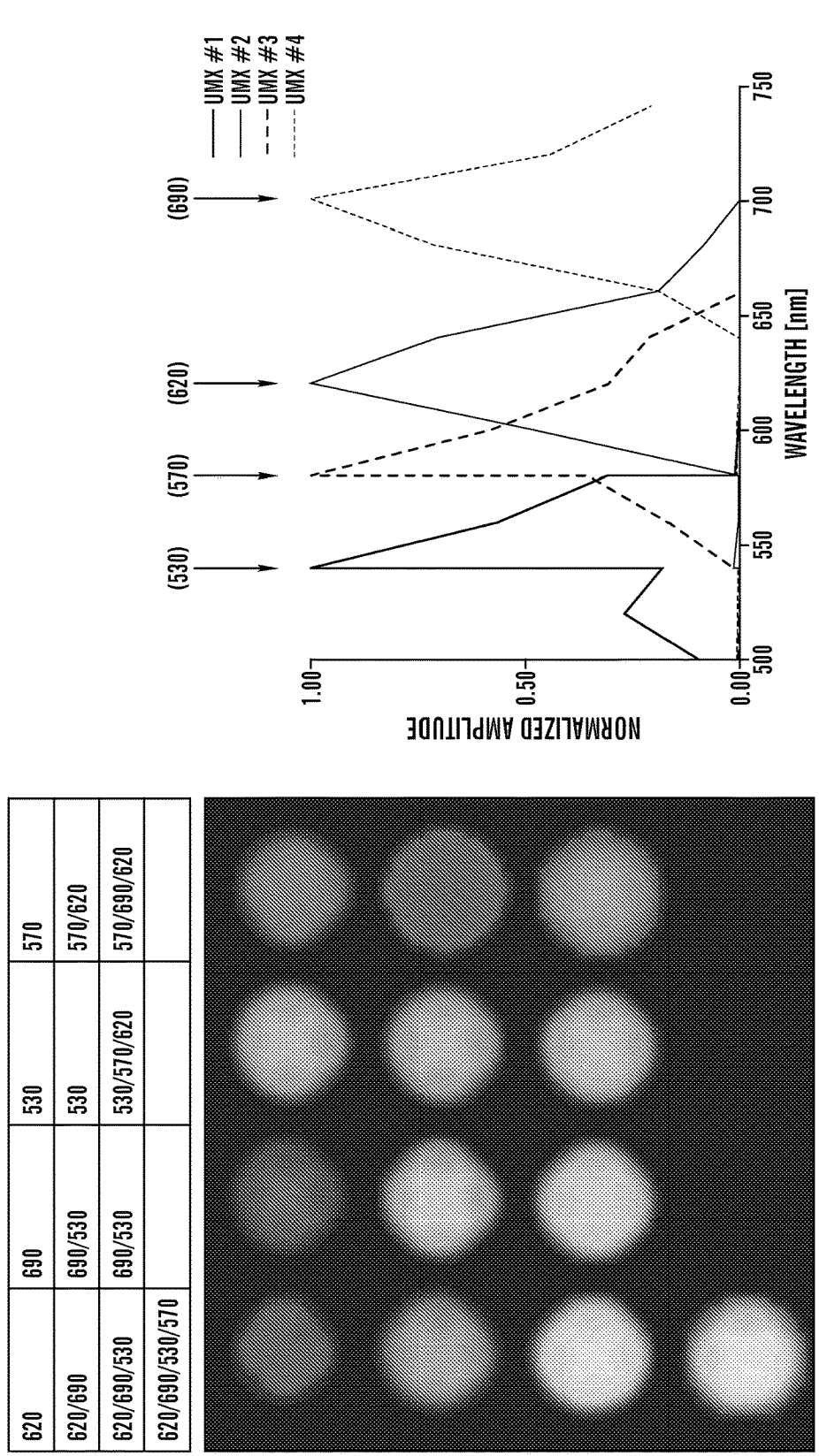
FIG. 10 shows experimental results indicating spectral unmixing of four dyes.

Sample data illustrating the ability to resolve four fluorophores are presented in FIG. 10. In this case, any single dye, two or three-dye combinations, and a mixture of all four dyes (FITC, Cy3®, DyLight®594, and IRDye®-700DX, 100 nM in PBS) were analyzed. The solutions were excited at 430, 500, 535, and 605 nm, and emission was collected from 500 nm to 750 nm. Radiant efficiency was recorded following spectral unmixing, as previously described[86]. The referenced publication further supports the feasibility of resolving fluorescence in several channels from the same region of interest, since it describes the application of the proposed spectral unmixing in vivo (in the brain).

Collectively the results indicate that the delivery method can be used to target the endogenous miRNA machinery in tumors and lymph nodes using MN-conjugated oligos. The results also suggest that the detection of miRNA activity using the proposed nanosensor design is feasible.

Example 2—Confirm and Optimize Design and Approach

A. Validate Candidate miRNAs Reflective of Breast Cancer Metastasis

The following miRNA microarray studies can be performed to verify the clinical relevance of candidate miRNAs using patient-matched tissues derived from primary tumors and metastatic lymph nodes. Bioinformatics can be employed to predict the mRNA targets of the candidate miRNAs, focusing on mRNA targets linked to tumor cell migration and invasion.

Preliminary studies have identified a set of candidate miRNAs that are differentially expressed between the primary tumors and lymph node metastases of mice orthotopically implanted with the human lymph node metastatic MDA-MB-231-luc-D3H2LN cell line. The set of candidate miRNAs will be filtered based on their conservation in clinical tissue samples and their testable relevance to metastasis, defined by their direct mRNA targets. Namely, this study will focus on miRNAs whose target mRNAs include those implicated in tumor cell migration and invasion. This will be accomplished using established bioinformatics tools and methods, known in the art and described herein. It is expected that the candidate miRNAs identified in the murine model of human breast cancer will be conserved in clinical tissue samples and will include miRNAs that directly regulate genes involved in cell migration and invasion.

miRNA qRT-PCR analysis of human tissues will be performed to verify the relevance of the candidate miRNAs to human disease. Human tissue samples derived from primary breast tumors and patient-matched lymph node metastasis will be secured. The tissues will be collected as part of a service provided by the NCI's cooperative human tissue network (CHTN). The tissues will be analyzed for miRNA expression, specifically looking for the targets identified in the preliminary results. miRNA microarray analysis will be performed using the RT$^2$ miRNome qPCR arrays (SABiosciences, Frederick, Md.). The arrays provide an excellent opportunity for a thorough characterization of global miRNA expression since they simultaneously detect genome-wide miRNA (as annotated in miRBase V16) with high sensitivity and specificity. The qPCR assays rely on SABiosciences validated primer design and assay formulation technologies to analyze the expression of any mature miRNA sequence in the human genome by SYBR Green based real-time RT-PCR. The assays will be performed with assistance from the Beth Israel Deaconess Medical Center's PCR Core Facility.

mRNA targets that are regulated by the candidate miRNAs will be identified. Bioinformatics will be employed to identify likely mRNA targets for each of the candidate miRNAs. Specifically, each of the candidate miRNAs, selected as a result of the above experiments will be submitted to miRBase (http://www.mirbase.org). This database includes the sequences of all of the currently annotated 1527 human miRNAs. Each of these miRNAs can be matched by the microCosm search engine for interrogation of the database to all annotated mRNA sequences in the GenBank database. Because each miRNA regulates its direct mRNA targets through complementary binding between the so-called "seed region" (bases 2-7 from the 5' end of the miRNA) and the mRNA sequence, the search engine can identify candidate mRNA targets (mRNAs that are partially or completely complementary to the seed region of a given miRNA). The higher the level of complementarity, the more likely it is that the predicted mRNA is a true miRNA target. To focus on likely targets, the search will select high-stringency, low total-context score (below −0.2) target sequences within the candidate mRNAs (i.e. sequences with a high level of complementarity to the seed region of the candidate miRNA). This will suggest that these mRNAs are direct miRNA targets.

As a set of candidate mRNA targets for each miRNA of interest is predicted, the identity of the mRNAs as targets will be empirically confirmed. Namely, qRT-PCR and western blotting will be used to validate the candidate targets. This will be done in MDA-MB-231-luc-D3H2LN tumor cells. First, cells will be treated with locked nucleic acid (LNA) miRNA inhibitors specific for the candidate miRNAs, according to established protocol (http://www.exiqon.com/ls/Documents/Scientific/miRNA-inhibitor-manual.pdf; Exiqon, Woburn, Mass.). Scrambled LNA probes will be used as controls. The LNA technology is selected because it is an established method for antisense miRNA inhibition. Locked nucleic acids are RNA monomers with a modified backbone (Exiqon proprietary technology). The sugar phosphate backbone has a 2'-O-4'-C methylene bridge. The bridge increases the monomer's thermal stability, reduces its flexibility, and increases the hybridization interactions of the base. For that reason, LNA oligos bind their complementary sequences with much higher affinity than either DNA or RNA oligonucleotides, making LNA oligonucleotides ideal for antisense knockdown applications. The structure of these oligonucleotides confers greater sensitivity and discrimination for the gene target, as they can distinguish between highly homologous targets with a single base difference. In addition, the higher melting temperature of the binding between the antisense LNA oligo and the target means a more significant inhibition of the target in knockdown experiments. miRNA expression will be confirmed using miRNA qPCR arrays and assays (SABiosciences, Frederick, Md.). mRNA expression analysis of the treated cells will be performed using human breast cancer PCR arrays (SABiosciences, Frederick, Md.), according to the manufacturer's protocol. The assay will be performed in association with the BIDMC PCR Core facility, as described above. miRNA and mRNA expression, following treatment with the LNA inhibitors (as described above), will be correlated to the migratory/invasive phenotype of the cells, using a commercial migration and invasion assay (CytoSelect™ 24-Well Cell Migration and Invasion Assay, 8 μm, Colorimetric Format; Cell Biolabs, San Diego, Calif.).

For data analysis and interpretation, microarray analysis will be performed using the online tool supplied by SABiosciences. Comparisons between miRNA and mRNA profiles from different stages of breast cancer will be performed by Analysis of Variance (ANOVA) with Tukey's pairwise comparison test. Correlations between will be performed by Pearson product moment correlation. In all knockdown studies, antisense LNA oligos specific for the miRNAs of interest will be compared to scrambled LNA oligos, as negative controls.

Progressive filtering of candidate sequences will be performed at each step with the goal of selecting the most promising candidates. The goal is to select 4 top candidates for screening in the below described experiments. Based on the literature, it is expected that of the candidates identified in the preliminary results (FIG. 2), miR-10b, 200c, 155, and 141 will be included. A review of prior studies reveals that common miRNAs identified in more than one study include miR10b[55, 59, 60]; ma-21[60-64]; miR-200 family, including miR-200c and miR-141[65-67] and Ma-205[60, 68, 69]; miR-9[65, 70], and miR-31[71,72]. A study by Tavazoie compared the miRNA signatures of the parental MDA-MB-231 cell line and a clone derived from lung metastases and identified miRNA-206 and -335 as regulators of lung metastases from the cell line[73]. However, that study focuses on miRNAs that are specifically involved in distant organ colonization and macroscopic tumor formation, which is different from the focus on migration and invasion, as an earlier biomarker of metastasis. Two studies ([60] and [65]) have compared the miRNA signatures of primary breast tumors and lymph node metastases in clinical samples. These studies identified different miRNA signatures and relied on small sample sizes (13 and 14, respectively). Therefore, these findings will be confirmed and the differences between these two studies will be resolved in a larger patient cohort and specifically focus on miRNAs that relate to epithelial to mesenchymal transition and invasion and migration, as opposed to macroscopic tumor formation at the distant site.

B. Design Tumor and Lymphotropic Nanosensors that can Report on Metastatic miRNA Activity Nanosensors consisting of magnetic nanoparticles conjugated to internally quenched miRNA substrate oligos will be synthesized and optimized. In vitro studies will be performed in primary tumor- and lymph node metastatic cells to assess the utility of the probes as miRNA reporters. Cell uptake, nuclease resistance, sensitivity and specificity of detection will be determined for each nanosensor, as a function of nanoparticle size and synthetic design, oligonucleotide sequence, length and modification, quencher-dye identity, and positioning on the oligonucleotide.

Nanosensors (MN-miRNA) will be designed for multiparametric tumor characterization in vivo. In particular, the MRI properties of the nanoparticles (MN) will allow semi-quantitatively measurement of probe accumulation in the target tissue through the delta-T2 effect, as shown previously[26, 74, 75]. In addition, the nanoparticles will be imparted with the ability to detect miRNA function in vivo. This will be accomplished by attaching fluorescently labeled miRNA substrate oligos. The oligos will be internally labeled with a fluorescent dye and a quencher. Cleavage of the substrate oligos by the cognate endogenous miRNA will lead to de-quenching and a fluorescent turn-on, as described above. It is expected that nuclease-resistant nanosensors of the general design described here, can report on miRNA activity in tumor cells with nanomolar sensitivity and with >95% specificity.

A library of nanosensors will be synthesized for each of the candidate miRNAs selected in the experiments described above and will test each nanosensor design in vitro in order to select the one with the highest nuclease stability, sensitivity of detection, and specificity of detection. The following parameters will be varied: the nanoparticle size and stoichiometry between the nanoparticles and cRGD peptides (to increase nanosensor uptake by the cells); stoichiometry between the nanoparticles and sensor oligos, mode of conjugation of the oligo to the nanoparticle (PEG vs. hexyl spacer, length of spacer), oligo length, dye-quencher identity and positioning on the oligo, and modification (phosphorothioate backbone, LNA, DNA, 2-O-Me vs. RNA bases) with the goal of increasing binding specificity by the cognate miRNA, increase signal to background fluorescence, maximize cleavage efficiency by the cognate miRNA, and increase serum stability.

Synthesis and Characterization

The synthesis and characterization of the MN nanoparticles will be performed as described in earlier studies[53] and illustrated by the results presented in Example 1. Briefly, to synthesize 20-nm magnetic nanoparticles, Dextan-T10 (Pharmacosmos, Denmark) will be combined with $FeCl_3.6H_2O$ and $FeCl_2.4H2O$ followed by precipitation of the colloid in $NH_4OH$. The resulting dextran coated magnetic nanoparticles will be cross-linked and aminated with epichlorohydrin and dialyzed. Iron concentration will be determined using iron assay and nanoparticle size will be determined by dynamic light scattering (IZetasizer Nano ZS, Malvern Instruments Ltd). Thiol-PEG-RGD and the thiolated sensor oligos will be attached via N-Succinimidyl 3-(2-pyridyldithio)-propionate (SPDP, Pierce Biotechnology) linker using a standard protocol as previously described[53]. To control the ratio of RGD and oligo per MN, the stoichiometry of the components in the reaction will be varied. cRGD: SH-PEG-cRGD will be synthesized as described in earlier work[75] and illustrated by the experimental results presented in Example 1.

The sensor oligos will be custom synthesized by Integrated DNA Technologies (Coralville, Iowa). Based on preliminary results, they will consist of a 20-25 nucleotide RNA sequence (most miRNAs are 22-25 nucleotides in length) that is perfectly complementary around the seed region. This length is well within the limit of 10 nm (30 nucleotides) imposed by the physics of fluorescence energy transfer. The oligos will incorporate a thiol group, followed by a hexyl or PEG spacer, and the target oligo, incorporating a quencher and a fluorescent dye, located 5' and 3' respectively to the 8-nucleotide seed region (the conserved region recognized by the cognate microRNA). A non-fluorescent pan-quencher (QC-1, Li-Cor Biosciences, Lincoln, Nebr.) and the following dyes with emission maxima over 600 nm will be tested: AlexaFluor® 594; AlexaFluor® 647; IRDye®-700DX; Alexa Fluor® 750; and IRDye®-800. Special care in selecting the oligo sequence will be taken to avoid the potential for internal dimers and other secondary structures. To achieve the optimal balance between minimal background fluorescence/maximal fluorescent turn-on upon cleavage, maximal lability around the cleavage site, and nuclease stability, the following will be varied: the identity and positioning of the quencher-dye pairs on the oligos, the positioning of RNA and DNA/LNA bases in the oligo, their modification (2-O-Me/phosphorothioate backbone) and the length of the oligo. Considering that the choice between mRNA degradation and translational repression is dependent on the degree of complementarity between the mRNA target and the miRNA seed region, it is expected that oligonucleotide probes perfectly complementary around the miRNA seed region will be cleaved in a sequence-specific way. This hypothesis is supported by recent research[76, 77] coupled with the results reported herein, in which the miR-10b-specific sensor oligonucleotide is cleaved by miR-10b, despite the fact that all of miR-10b's known mRNA targets bound with imperfect complementarity and regulated by translational repression and not mRNA cleavage.

In Vitro Testing

The functionality of the probes will be tested in tumor cells isolated from the primary tumor and lymph node metastases of MDA-MB-231(luc) tumor-bearing mice. Cells will be isolated from the primary tumor 2 weeks after tumor implantation (pre-metastatic stage, to identify the pre-metastatic signature), and from the tumor and lymph nodes at 4 weeks (early metastatic stage) and 6 weeks after implantation (late metastatic stage). In this case, the premetastatic stage is defined as the stage at which no metastases can be identified by imaging or histopathology, whereas the post-metastatic stage refers to the stage at which either only lymph node or lymph node and lung metastases can be identified. Although this model suffers from some level of innate artificiality, since the cell line is derived from a metastatic tumor, the model can be used to determine phenotypes consistent with pre-metastatic and lymph node-/lung-metastatic stages of cancer, because of the innate clonal diversity that is found in metastatic cell lines that are derived from spontaneous metastasis (as high as 50% of the cells are in fact not metastatic as is known from previous work[78,79]). Therefore, by introducing cells derived from this cell line orthotopically and allowing these cells to metastasize to the lymph nodes, the lymph node metastases will be enriched with cells of the metastatic signature and that signature can be determined by directly comparing the primary tumors and metastases in the same animal. To enhance the focus on targets that are truly representative of non-metastatic vs. metastatic miRNA signatures, only miRNA targets will be selected that demonstrate differential expression in human biopsy samples, as described above.

Nanosensor Uptake

Nanosensor uptake will be evaluated by iron assay and Prussian blue staining. The design with the highest uptake per cell will be selected for further studies.

miRNA Expression miRNA expression will be determined by RT-PCR as described above and will be correlated to miRNA activity, as determined using the nanosensors.

miRNA Activity, Specificity, and Sensitivity miRNA activity, specificity, and sensitivity will be determined following incubation of the cells with the nanosensors for 48-72 hrs at 37° C. Following, the cells will be washed and examined by confocal microscopy using filters appropriate for the selected substrate oligos (each identified by distinct quencher-dye combinations). To assess the sensitivity of detection, a cell-free assay will be performed, as described in preliminary results, with increasing concentrations of the nanosensor and will use as controls scrambled oligonucleotides or deletion/knockdown of the target gene using Exiqon's miRNA inhibitors (Exiqon, Woburn, Mass.). In addition, an experiment will be designed such that the cells will be transfected with increasing concentrations of a non-native miRNA analogue (irrelevant siRNA, Exiqon, Woburn, Mass.), ranging from 2-1000 copies per cell. Following, the cells will be lysed and analyzed by the cell-free assay, as described herein, using a sensor oligo specific for the irrelevant siRNA sequence. The specificity of detection will be determined by incorporating 1, 2, and 3-base mismatches into the sensor oligo and performing the described cell free assay with the expectation that even a 1-base mismatch will be discriminated using the nanosensors based on fluorescence enhancement. This expectation is justified by the fact that these oligonucleotides are routinely used to detect single nucleotide polymprphisms by in situ hybridization (Exiqon, Woburn, Mass.).

Serum Stability

Serum stability will be assessed by incubation of the nanosensors in human serum at 37° C. for varying lengths of time ranging from 30 min. to 12 hrs. Following, the products will be loaded on a polyacrylamide gel and analyzed by electrophoresis, as described in[80]. Prior studies have demonstrated that conjugation of RNA oligonucleotides to a carrier (in this case MN), affords significant protection from nuclease digestion in vivo[53,54, 80]. Therefore, it is expected that the sensor oligos to remain stable in serum.

Data Analysis and Interpretation

Comparisons between the primary tumor and metastases will be performed by repeated measures Analysis of Variance (ANOVA) with Tukey's pairwise comparison test. Correlations between different methods of miRNA analysis (RT-PCR and fluorescence using the probes) will be performed by Pearson product moment correlation. Comparisons between experimental and control probes (negative or positive) will be performed using Student's t-test. A p value ≤0.05 will be considered statistically significant.

Controls

Nanoparticles functionalized with an irrelevant oligo (Exiqon, Woburn, Mass.) will be used as a negative control. Also, nanoparticles functionalized with an oligo specific for one of the classic reference small RNAs (SNORD38B, SNORD44) that demonstrate stable expression will be used as an internal positive control. In addition, cells with inhibited target miRNA will be used as a negative control. For the studies on specificity, the sensor oligonucleotides will be compared to oligonucleotides with 1, 2, and 3-base mismatches. In all of the studies, results will be quantified as follows: The cells will be incubated with an experimental oligo (complementary to a candidate miRNA) and a positive control oligo (complementary to SNORD38 or 44 and labeled with a different dye-quencher pair). Fluorescence intensity from the experimental oligos will be divided by that of the positive control and expressed as a ratio. This method of normalization is borrowed from the quantitative PCR technology.

Recent research suggests that the prevalence of miRNA-dependent degradation targets in mammals is higher than previously thought and that the choice between mRNA degradation, translational repression is dependent on the degree of complementarity between the mRNA target and the miRNA seed region[76, 77]. This hypothesis is also supported by the results reported herein, in which the miR-10b-specific sensor oligonucleotide is cleaved by miR-10b, despite the fact that all of miR-10b's known mRNA targets are regulated by translational repression and not mRNA cleavage. The approach described herein is designed to "sense" any of the ~1527 annotated human miRNAs because the proposed synthetic oligonucleotide probes are perfectly complementary to each miRNA, as defined in miRBase.

The feasibility of the quenching-dequenching mechanism for the generation of signal has been demonstrated numerous times over the years and is well-established in vivo[28-30] commercially available and validated dye-quencher pairs will be used. The probes will be synthesized using ~20-nucleotide oligos, labeled with a quencher-dye pair spanning the 8-nucleotide seed region. This is well within the limit of 5-10 nm (15-30 nucleotides) imposed by the physics of fluorescence energy transfer. The specific quenching efficiencies for the quencher dye pairs selected for these studies approach 99% at a distance of 3 nm (10 bases). (http://biosupport.licor.com/docs/QC-1DarkQuencher_v5.pdf). In addition, at this distance, steric hindrance will not present an issue, because these quencher-dye combinations are used commercially as sensors for caspase activity using cleavage of the 2.9-nm GDEVDGAK (SEQ ID NO: 13) octapeptide substrate (Li-Cor Biosciences, Lincoln, Nebr.; http://biosupport.licor.com/docs/QC-1DarkQuencher_v5.pdf). In these studies, a 10-nucleotide distance between the quencher and dye has a length of 3.4 nm (10*3.4 Å/nucleotide=34 Å=3.4 nm). For the IRDye® 700DX-QC-1 pair, the expected quenching efficiency at that distance will be 98.8%. In addition, the overall fluorescent turn-on upon de-quenching is expected to exceed that reported for 1:1 hybridization probes, since the method takes advantage of three signal amplification strategies. The first is that a single miRNA will cleave numerous substrate oligos, since RNAi is a "catalytic" molecular mechanism. In other words, the miRNA is not consumed by its interaction with the substrate oligo and participates in multiple cleavage reactions.

The second is that a single nanoparticle will carry up to 40 substrate oligos, taking advantage of the phenomenon of multivalency[81,82]. The third is that the extent of the signal amplification is further underscored by new results obtained with the MN-miR10b nanosensor. The number of nanoparticles taken up by the tumor cells was determined by using a commercially available iron binding assay (Total Iron Reagent Set, Pointe Scientific, Canton Mich.) and as previously described[83]. The number of target miRNA molecules for the miR-10b target was also determined by using qRT-PCR. Based on analysis, at 24 hrs of incubation, the MDA-MB-231 cells took up 3 pg of iron/cell, equivalent to $15\times10^6$ nanoparticles (assuming 2064 iron atoms per MN nanoparticle[84]). The MDA-MB-231 cells have around 400 copies of the miR-10b target per cell (from qRT-PCR 7,500-fold less abundant than 18s rRNA, of which there are roughly $3.3\times10^6$ copies per cell[85]). Each miR-10b cleaves its substrate catalytically, leading to powerful signal amplification resulting from the cleavage of millions of synthetic substrates on the nanoparticles by the cognate miRNA.

Cell uptake of the probes and the capability of the RNAi apparatus to access the nanoparticle-tagged oligo has been investigated and issues have been addressed by prior publications[27,53] and the results reported herein. The nanosensor design can be further optimized by one or more of the following procedures: the use of alternative nanosensor concentrations (50-200 µg/ml of iron), different dye-quencher pairs and locations within the oligo, the use of different oligo sequences, lengths, modifications, and densities per nanoparticle.

C. Profile miR Signatures in Primary Tumors and Lymph Node Metastases Using Noninvasive Imaging Semi-quantitative MRI will be employed for assessment of probe uptake by the target tissues.

In vivo optical imaging of primary tumors and lymph nodes will be employed to determine miRNA expression and correlate to tumor/metastatic burden by bioluminescence optical imaging. The obtained results will be validated ex vivo.

MN-miRNA is designed so that it can be detected by noninvasive MR/optical imaging. Each modality will report on a different biological aspect. Tumor-targeted MRI will allow the semi-quantitative assessment of nanosensor uptake by the tumor, as demonstrated in prior publications[26,74,75] and by the results presented in Example 1. Bioluminescence imaging (BLI) will permit the assessment of tumor and metastatic burden, since the MDA-MB-231(luc) cell line carries the luciferase reporter. BLI can be performed in the same imaging session and using the same instrument as fluorescence optical imaging, so that the two can be co-registered with a high level of precision. Fluorescence optical imaging will define the activity of a set of candidate miRNAs.

Pilot studies will be conducted to target single miRNAs. These studies will allow the optimization of parameters such as nanosensor concentration, image acquisition and analysis. Following, a cocktail of nanosensors will be injected simultaneously for multiplex profiling of miRNA expression.

The nanosensors, as designed, are expected to allow us to detect miRNA activity in primary tumors and metastases in vivo.

Animals

The experiments will be performed in female nude mice injected in the fat pad with the MDA-MB-231-luc-D3H2LN cell line.

MRI

MR Imaging protocols (T2-weighted) will be designed based on sequences used in the results of the experiments described herein and on prior publications[26,75]. Specifically, the animals will be imaged before and 24 hours after i.v. injection of MN-miRNA (10 mg/kg of iron, although the dose can be adjusted based on the results of pilot studies, since delivery of up to 30 mg/kg of iron are routinely reported). There will be a total of three injections: at 2 weeks after tumor inoculation (pre-metastatic), and at 4 and 6 weeks after implantation (to identify the early and late metastatic signatures). According to the known clearance kinetics of these probes, at this schedule there will be no interference from probe retained from prior injections. The circulation half-life is approximately 12 hrs in rodents. Fourteen days represent 28 half-lives, at which point there will be a $4\times10^{-9}$ fraction of the original nanosensor left. However, by normalizing to nanosensor delivery through the delta-T2 parameter, variability in the amount of nanosensor delivered to the tumor by each injection will be accounted for.

Optical Imaging

Optical imaging (BLI and fluorescence) will be performed immediately after each MR imaging session (pre- and post-contrast). For optical imaging, animals will be placed into a whole-body animal imaging system (IVIS Spectrum, Caliper Life Sciences, Hopkinton Mass.), equipped with appropriate filters. The imaging settings (exposure time, F-stop, Binning) will be kept constant for comparative analysis. Gray scale white-light photographs and epifluorescent and bioluminescent images will be acquired, superimposed, and analyzed using the Living Image software. A subset of animals will be sacrificed at each time point. The system has dedicated autofluorescence subtraction and spectral unmixing algorithms and protocols. Spectral unmixing, in particular, will be used in multiplexing studies. The IVIS Spectrum has a minimum detectable radiance of 70 photons/second/$cm^2$/steradian, and the technology platform is calibrated to NIST-traceable radiance standards so that images measured in relative light units (or CCD camera counts) may be converted into physical units of surface radiance (photons/second/$cm^2$/steradian).

Specifically, image analysis will performed by manually selecting a region of interest (ROI) overlying the tumor or lymph node, as defined by bioluminescence imaging. A wavelength scan will be performed and radiance area under the curve, corresponding to each fluorophore will be calculated following spectral unmixing using the Living Image Software. Data will be collected before nanosensor injection and, up to 1, then 2, 4, 6, 12, 24, 48, and 72 hrs after injection. The readings will be plotted as a function of time and the slope of the line will be used as a quantitative surrogate for fluorescent turn-on. The area of the ROI will be kept constant and the intensity will be recorded as radiant efficiency.

It is conceivable that the maximum number of nanosensors that can be resolved fluorescently will be limited. In some experiments, four fluorophores were successfully unmixed in the same region of interest using the spectral unmixing tool of the Ivis Spectrum (Caliper Life Sciences, Hopkinton, Mass.). At least 4, possibly a higher number of targets will be able to be resolved in a single imaging session.

Ex Vivo Analysis

The ex vivo histological analysis will include assessment of nanosensor uptake, functionality, miRNA expression, and tumor stage (pre-metastatic, early and late metastatic), as described above (in vitro testing). Metastatic burden will be determined from in vivo and ex vivo bioluminescence imaging (photons/sec/cm$^2$/steradian, reported by the Ivis imaging system), by visual scoring at necropsy, and also by hematoxylin and eosin staining of excised organs.

Data Analysis and Interpretation

Comparisons as a function of time after tumor inoculation will be performed by repeated measures Analysis of Variance (ANOVA). Correlations between different methods of miRNA analysis (RT-PCR and fluorescence using nanosensors described herein) and between tumor stage (metastatic burden) and individual miRNA expression will be determined by Pearson product moment correlation. Comparisons between experimental and control nanosensors will be performed using Student's t-test.

Controls

Experiments will be performed in which nanoparticles functionalized with an irrelevant oligo with no known human targets (Exiqon, Woburn, Mass.) will be used as a negative control and nanoparticles functionalized with an oligo specific for one of the classic reference small RNAs (SNORD38B, SNORD44) will be used as a positive control.

Optimization

Variables such as dye-quencher pairs, oligo sequences, lengths and densities per nanoparticle will be optimized as discussed above. Alternative nanosensor concentrations (10-30 mg/kg of iron) will also be used. The approach leading to the highest nanosensor accumulation in the target tissues and the most reproducible fluorescence signal that demonstrates the highest correlation with RT-PCR will be used in subsequent experiments.

REFERENCES FOR EXAMPLES 1-2 AND BACKGROUND SECTION

1. Kimura, S. et al. Expression of microRNAs in squamous cell carcinoma of human head and neck and the esophagus: miR-205 and miR-21 are specific markers for HNSCC and ESCC. *Oncol Rep* 23, 1625-1633.
2. Foley, N. H. et al. MicroRNA-184 inhibits neuroblastoma cell survival through targeting the serine/threonine kinase AKT2. *Mol Cancer* 9, 83.
3. Caramuta, S. et al. MicroRNA Expression Profiles Associated with Mutational Status and Survival in Malignant Melanoma. *J Invest Dermatol*.
4. Jiang, S. et al. MicroRNA-155 functions as an OncomiR in breast cancer by targeting the suppressor of cytokine signaling 1 gene. *Cancer Res* 70, 3119-3127.
5. Liu, X. et al. MicroRNA-31 functions as an oncogenic microRNA in mouse and human lung cancer cells by repressing specific tumor suppressors. *J Clin Invest* 120, 1298-1309.
6. Creighton, C. J. et al. Molecular profiling uncovers a p53-associated role for microRNA-31 in inhibiting the proliferation of serous ovarian carcinomas and other cancers. *Cancer Res* 70, 1906-1915.
7. Chen, F. et al Inhibition of c-FLIP expression by miR-512-3p contributes to Taxol-induced apoptosis in hepatocellular carcinoma cells. *Oncol Rep* 23, 1457-1462.
8. Ma, L. et al. Therapeutic silencing of miR-10b inhibits metastasis in a mouse mammary tumor model. *Nat Biotechnol* 28, 341-347.
9. Treon, S. et al. Muc-1 core protein is expressed on multiple myeloma cells and is induced by dexamethasone. *Blood* 93, 1287-1298 (1999).
10. Hu, H. et al. Antisense oligonucleotide against miR-21 inhibits migration and induces apoptosis in leukemic K562 cells. *Leuk Lymphoma* 51, 694-701.
11. Vidic, S. et al. MicroRNAs targeting mutant K-ras by electrotransfer inhibit human colorectal adenocarcinoma cell growth in vitro and in vivo. *Cancer Gene Ther*.
12. Takeshita, F. et al. Systemic delivery of synthetic microRNA-16 inhibits the growth of metastatic prostate tumors via downregulation of multiple cell-cycle genes. *Mol Ther* 18, 181-187.
13. Kota, J. et al. Therapeutic microRNA delivery suppresses tumorigenesis in a murine liver cancer model. *Cell* 137, 1005-1017 (2009).
14. Buckley, P. G. et al. Chromosomal and miRNA Expression Patterns Reveal Biologically Distinct Subgroups of 11q-Neuroblastoma. *Clin Cancer Res*.
15. Hui, A. B. et al. Comprehensive MicroRNA profiling for head and neck squamous cell carcinomas. *Clin Cancer Res* 16, 1129-1139.
16. Zhao, J. J. et al. microRNA expression profile and identification of miR-29 as a prognostic marker and pathogenetic factor by targeting CDK6 in mantle cell lymphoma. *Blood* 115, 2630-2639.
17. Akinc, A. et al. A combinatorial library of lipid-like materials for delivery of RNAi therapeutics. *Nat Biotechnol* 26, 561-569 (2008).
18. Garzon, R. et al. MicroRNA signatures associated with cytogenetics and prognosis in acute myeloid leukemia. *Blood* 111, 3183-3189 (2008).
19. Sempere, L. F. et al. Altered MicroRNA expression confined to specific epithelial cell subpopulations in breast cancer. *Cancer Res* 67, 11612-11620 (2007).
20. Rossi, S. et al. microRNA fingerprinting of CLL patients with chromosome 17p deletion identify a miR-21 score that stratifies early survival. *Blood*.
21. Zhou, Y. et al. High-risk myeloma is associated with global elevation of miRNAs and overexpression of EIF2C2/AGO2. *Proc Natl Acad Sci USA* 107, 7904-7909.
22. Mu, P. et al. Genetic dissection of the miR-17~92 cluster of microRNAs in Myc-induced B-cell lymphomas. *Genes Dev* 23, 2806-2811 (2009).
23. Wang, L. et al. Gene networks and microRNAs implicated in aggressive prostate cancer. *Cancer Res* 69, 9490-9497 (2009).
24. Lowery, A. J. et al. MicroRNA signatures predict oestrogen receptor, progesterone receptor and HER2/neu receptor status in breast cancer. *Breast Cancer Res* 11, R27 (2009).
25. Foekens, J. A. et al. Four miRNAs associated with aggressiveness of lymph node-negative, estrogen receptor-positive human breast cancer. *Proc Natl Acad Sci USA* 105, 13021-13026 (2008).
26. Medarova, Z., Rashkovetsky, L., Pantazopoulos, P. & Moore, A. Multiparametric Monitoring of Tumor Response to Chemotherapy by Noninvasive Imaging. *Cancer Res* 69, 1182-1189 (2009).

27. Medarova, Z. et al. Multifunctional magnetic nanocarriers for image-tagged SiRNA delivery to intact pancreatic islets. *Transplantation* 86, 1170-1177 (2008).
28. Tung, C. H., Mahmood, U., Bredow, S. & Weissleder, R. In vivo imaging of proteolytic enzyme activity using a novel molecular reporter. *Cancer Res* 60, 4953-4958 (2000).
29. Bremer, C., Bredow, S., Mahmood, U., Weissleder, R. & Tung, C. H. Optical imaging of matrix metalloproteinase-2 activity in tumors: feasibility study in a mouse model. *Radiology* 221, 523-529 (2001).
30. Ntziachristos, V., Tung, C. H., Bremer, C. & Weissleder, R. Fluorescence molecular tomography resolves protease activity in vivo. *Nat Med* 8, 757-760 (2002).
31. Harisinghani, M. G. et al. Noninvasive detection of clinically occult lymph-node metastases in prostate cancer. *N Engl J Med* 348, 2491-2499 (2003).
32. Michel, S. C. et al. Preoperative breast cancer staging: MR imaging of the axilla with ultrasmall superparamagnetic iron oxide enhancement. *Radiology* 225, 527-536 (2002).
33. Soliman, H. et al. Functional imaging using diffuse optical spectroscopy of neoadjuvant chemotherapy response in women with locally advanced breast cancer. *Clin Cancer Res* 16, 2605-2614.
34. van de Ven, S. et al. A Novel Fluorescent Imaging Agent for Diffuse Optical Tomography of the Breast: First Clinical Experience in Patients. *Mol Imaging Biol* (2009).
35. Poellinger, A. et al. Near-infrared laser computed tomography of the breast first clinical experience. *Acad Radiol* 15, 1545-1553 (2008).
36. Manohar, S. et al. Initial results of in vivo non-invasive cancer imaging in the human breast using near-infrared photoacoustics. *Opt Express* 15, 12277-12285 (2007).
37. Kang, W. J. et al. Molecular beacon-based bioimaging of multiple microRNAs during myogenesis. *Biomaterials* 32, 1915-1922.
38. Hwang do, W., Song, I. C., Lee, D. S. & Kim, S. Smart magnetic fluorescent nanoparticle imaging probes to monitor microRNAs. *Small* 6, 81-88.
39. Pohlmann, C. & Sprinzl, M. Electrochemical Detection of MicroRNAs via Gap Hybridization Assay. *Anal Chem*.
40. Song, R., Ro, S. & Yan, W. In situ hybridization detection of microRNAs. *Methods Mol Biol* 629, 287-294.
41. Li, W., Zhao, B., Jin, Y. & Ruan, K. Development of a low-cost detection method for miRNA microarray. *Acta Biochim Biophys Sin (Shanghai)* 42, 296-301.
42. Husale, S., Persson, H. H. & Sahin, O. DNA nanomechanics allows direct digital detection of complementary DNA and microRNA targets. *Nature* 462, 1075-1078 (2009).
43. Xu, F., Dong, C., Xie, C. & Ren, J. Ultrahighly sensitive homogeneous detection of DNA and microRNA by using single-silver-nanoparticle counting. *Chemistry* 16, 1010-1016.
44. Mandir, J. B. et al. Rapid determination of RNA accessible sites by surface plasmon resonance detection of hybridization to DNA arrays. *Anal Chem* 81, 8949-8956 (2009).
45. Driskell, J. D., Primera-Pedrozo, O. M., Dluhy, R. A., Zhao, Y. & Tripp, R. A. Quantitative surface-enhanced Raman spectroscopy based analysis of microRNA mixtures. *Appl Spectrosc* 63, 1107-1114 (2009).
46. Li, J., Schachermeyer, S., Wang, Y., Yin, Y. & Zhong, W. Detection of microRNA by fluorescence amplification based on cation-exchange in nanocrystals. *Anal Chem* 81, 9723-9729 (2009).
47. Havelda, Z. In situ detection of miRNAs using LNA probes. *Methods Mol Biol* 592, 127-136.
48. Lu, J. & Tsourkas, A. Imaging individual microRNAs in single mammalian cells in situ. *Nucleic Acids Res* 37, e100 (2009).
49. Nuovo, G. J. et al. A methodology for the combined in situ analyses of the precursor and mature forms of microRNAs and correlation with their putative targets. *Nat Protoc* 4, 107-115 (2009).
50. Silahtaroglu, A. N. et al. Detection of microRNAs in frozen tissue sections by fluorescence in situ hybridization using locked nucleic acid probes and tyramide signal amplification. *Nat Protoc* 2, 2520-2528 (2007).
51. Nelson, P. T. et al. Microarray-based, high-throughput gene expression profiling of microRNAs. *Nat Methods* 1, 155-161 (2004).
52. Moore, A., Weissleder, R. & Bogdanov, A., Jr. Uptake of dextran-coated monocrystalline iron oxides in tumor cells and macrophages. *Journal of magnetic resonance imaging: JMRI* 7, 1140-1145 (1997).
53. Medarova, Z., Pham, W., Farrar, C., Petkova, V. & Moore, A. In vivo imaging of siRNA delivery and silencing in tumors. *Nat Med* 13, 372-377 (2007).
54. Kumar, M., Yigit, M., Dai, G., Moore, A. & Medarova, Z. Image-guided breast tumor therapy using a small interfering RNA nanodrug. *Cancer Res* 70, 7553-7561 (2010).
55. Ma, L., Teruya-Feldstein, J. & Weinberg, R. A. Tumour invasion and metastasis initiated by microRNA-10b in breast cancer. *Nature* 449, 682-688 (2007).
56. Tarbe, N. et al. Transcriptional profiling of cell lines derived from an orthotopic pancreatic tumor model reveals metastasis-associated genes. *Anticancer Res* 21, 3221-3228 (2001).
57. Brown, K. M., Chu, C. Y. & Rana, T. M. Target accessibility dictates the potency of human RISC. *Nature structural & molecular biology* 12, 469-470 (2005).
58. Robb, G. B., Brown, K. M., Khurana, J. & Rana, T. M. Specific and potent RNAi in the nucleus of human cells. *Nature structural & molecular biology* 12, 133-137 (2005).
59. Ma, L. et al. Therapeutic silencing of miR-10b inhibits metastasis in a mouse mammary tumor model. *Nature biotechnology* 28, 341-347 (2010).
60. Baffa, R. et al. MicroRNA expression profiling of human metastatic cancers identifies cancer gene targets. *J Pathol* 219, 214-221 (2009).
61. Yan, L. X. et al. MicroRNA miR-21 overexpression in human breast cancer is associated with advanced clinical stage, lymph node metastasis and patient poor prognosis. *Rna* 14, 2348-2360 (2008).
62. Song, B. et al. MicroRNA-21 regulates breast cancer invasion partly by targeting tissue inhibitor of metalloproteinase 3 expression. *J Exp Clin Cancer Res* 29, 29 (2010).
63. Huang, T. H. et al. Up-regulation of miR-21 by HER2/neu signaling promotes cell invasion. *The Journal of biological chemistry* 284, 18515-18524 (2009).
64. Zhu, S. et al. MicroRNA-21 targets tumor suppressor genes in invasion and metastasis. *Cell Res* 18, 350-359 (2008).
65. Gravgaard, K. H. et al. The miRNA-200 family and miRNA-9 exhibit differential expression in primary versus corresponding metastatic tissue in breast cancer. *Breast Cancer Res Treat* (2012).
66. Burk, U. et al. A reciprocal repression between ZEB1 and members of the miR-200 family promotes EMT and invasion in cancer cells. *EMBO reports* 9, 582-589 (2008).
67. Dykxhoorn, D. M. et al. miR-200 enhances mouse breast cancer cell colonization to form distant metastases. *PLoS One* 4, e7181 (2009).
68. Wu, H., Zhu, S. & Mo, Y. Y. Suppression of cell growth and invasion by miR-205 in breast cancer. *Cell Res* 19, 439-448 (2009).
69. Gregory, P. A. et al. The miR-200 family and miR-205 regulate epithelial to mesenchymal transition by targeting ZEB1 and SIP1. *Nature cell biology* 10, 593-601 (2008).
70. Ma, L. et al. miR-9, a MYC/MYCN-activated microRNA, regulates E-cadherin and cancer metastasis. *Nat Cell Biol* 12, 247-256.
71. Valastyan, S., Chang, A., Benaich, N., Reinhardt, F. & Weinberg, R. A. Concurrent suppression of integrin alpha5, radixin, and RhoA phenocopies the effects of miR-31 on metastasis. *Cancer Res* 70, 5147-5154.
72. Valastyan, S. et al. A pleiotropically acting microRNA, miR-31, inhibits breast cancer metastasis. *Cell* 137, 1032-1046 (2009).
73. Tavazoie, S. F. et al. Endogenous human microRNAs that suppress breast cancer metastasis. *Nature* 451, 147-152 (2008).
74. Moore, A., Medarova, Z., Potthast, A. & Dai, G. In vivo targeting of underglycosylated MUC-1 tumor antigen using a multimodal imaging probe. *Cancer Res* 64, 1821-1827 (2004).
75. Medarova, Z., Pham, W., Kim, Y., Dai, G. & Moore, A. In vivo imaging of tumor response to therapy using a dual-modality imaging strategy. *Int J Cancer* 118, 2796-2802 (2006).
76. Bracken, C. P. et al. Global analysis of the mammalian RNA degradome reveals widespread miRNA-dependent and miRNA-independent endonucleolytic cleavage. *Nucleic acids research* 39, 5658-5668 (2011).
77. Bracken, C. P. et al. Global analysis of the mammalian RNA degradome reveals widespread miRNA-dependent and miRNA-independent endonucleolytic cleavage. *Nucleic Acids Res*.
78. Poste, G. Cellular heterogeneity in malignant neoplasms and the therapy of metastases. *Ann N Y Acad Sci* 397, 34-48 (1982).
79. Poste, G. & Greig, R. On the genesis and regulation of cellular heterogeneity in malignant tumors. *Invasion Metastasis* 2, 137-176 (1982).
80. Wang, P. et al. Combined small interfering RNA therapy and in vivo magnetic resonance imaging in islet transplantation. *Diabetes* 60, 565-571 (2011).
81. Hong, S. et al. The binding avidity of a nanoparticle-based multivalent targeted drug delivery platform. *Chem Biol* 14, 107-115 (2007).
82. Weissleder, R., Kelly, K., Sun, E. Y., Shtatland, T. & Josephson, L. Cell-specific targeting of nanoparticles by multivalent attachment of small molecules. *Nat Biotechnol* 23, 1418-1423 (2005).
83. Evgenov, N. V., Medarova, Z., Dai, G., Bonner-Weir, S. & Moore, A. In vivo imaging of islet transplantation. *Nat Med* 12, 144-148 (2006).
84. Shen, T., Weissleder, R., Papisov, M., Bogdanov, A., Jr. & Brady, T. J. Monocrystalline iron oxide nanocompounds (MION): physicochemical properties. *Magn Reson Med* 29, 599-604 (1993).
85. Duncan, R. & Hershey, J. W. Identification and quantitation of levels of protein synthesis initiation factors in crude HeLa cell lysates by two-dimensional polyacrylamide gel electrophoresis. *The Journal of biological chemistry* 258, 7228-7235 (1983).
86. Ran, C. & Moore, A. Spectral Unmixing Imaging of Wavelength-Responsive Fluorescent Probes: An Application for the Real-Time Report of Amyloid Beta Species in Alzheimer's Disease. *Mol Imaging Biol* (2011).

Example 3—Tumor miRNA Profiling with Nanosensors

The following experiments were performed to develop technology for tumor miRNA profiling. This technology relies on nanosensors capable of reporting on miRNA abundance in intact cells. Specifically, the nanosensors are based on fluorescent turn-on oligonucleotide probes sensitive to individual microRNA-mediated RNA interference. For delivery into intact cells, the oligos are conjugated to iron oxide nanoparticles that will serve as efficient delivery vehicles. Preliminary results and prior publications have shown that: 1) the nanosensors, as designed, are delivered to intact cells using simple incubation; 2) once inside the cell, the nanosensors successfully engage the RNA interference machinery in a microRNA-specific way; 3) the fluorescent read-out generated by the sensors is highly specific and has nanomolar sensitivity to miRNA; 4) the proposed assay is inexpensive ($40/L of assay solution) and rapid (2-3 hrs).

The miRNA epigenome represents a fundamental molecular regulator of metastasis. Consequently, developing tools to understand metastatic changes at the miRNA level can lead to the mapping out of a comprehensive and systematic atlas of cancer progression. The proposed technology is potentially transformative because it addresses this important issue. Furthermore, the technology has broad implications and can be utilized in any model system or clinical scenario to answer questions related to microRNA function. Specifically, the technology can help distinguish, assess, and/or monitor cancer stages and progression; aid the elucidation of basic mechanisms underlying cancer initiation and progression; facilitate early cancer detection and/or cancer risk assessment; and facilitate/accelerate the processes of drug discovery.

The technology developed makes possible profiling of pro-metastatic miRNA expression in intact tumor cells. The technology is based on nanosensors capable of reporting on miRNA-mediated RNAi. This technology will be assessed as a basic biology tool using breast cancer cell lines. Finally, it will be evaluated as a diagnostic tool using human tissue samples.

This approach involves the profiling of miRNA expression in cells/tissues with very high potential sensitivity and specificity and using a very low-cost rapid assay format that permits analysis in intact cells. The technology enables a scenario in which, as part of routine histopathology, biopsied tissues are examined by the proposed method to highlight individual cells with high metastatic potential. This information can be used to guide decisions regarding therapeutic intervention.

The currently established methods for microRNA detection in situ rely on PCR and northern blotting, or high-affinity hybridization probes. However, none of these methods are applicable in intact live cells. Consequently, these methods do not permit longitudinal studies, in which the "evolution" of the metastatic phenotype is monitored in an intact cellular environment. In contrast, this approach offers the possibility for detection in intact cells. Secondly, the existing methods rely on direct hybridization of the sensor oligo to the miRNA, reflecting a 1:1 ratio of fluorescent probe per miRNA. By contrast this approach is very sensitive-each miRNA cleaves its substrate catalytically, leading to signal amplification resulting from the cleavage of millions of synthetic substrates on the nanoparticles.

The results disclosed herein coupled with that of prior publications[15,16,17], indicates the effectiveness of this technology and approach.

Technology Design

Nanoparticles have been developed that accumulate in live tumor cells, following simple incubation. The design and testing of these nanoparticles is extensively described in the literature[17]. Upon internalization of the nanoparticles by the cell, the nanoparticles efficiently engage the endogenous cytosolic RNA interference apparatus in a sequence-specific way. The nanoparticles consist of dextran-coated iron oxide crystals (MN, 25-30 nm in diameter), conjugated to sensor oligos that are complementary to endogenous miRNA species (FIG. 1A). These sensor oligonucleotides are composed of RNA bases, are cleavable (non-stabilized by chemical modification) around the seed region (the conserved region within which the microRNA engages the RNA substrate), and are labeled with a fluorescent dye-quencher pair, so that upon cleavage of the oligonucleotide by the microRNA-RISC, there is fluorescence enhancement (FIG. 1A). The proposed mechanism is described in FIG. 1B. Namely, the peptide-targeted nanoparticles are recognized (FIG. 1B1) and engaged (FIG. 1B11) by the tumor-specific receptor on tumor cells and localize to endosomes (FIG. 1B111). Inside endosomes, the functionalized nanoparticles rich in unsaturated amines mediate the proton sponge effect by sequestering protons that are supplied by the v-ATPase (proton pump). This process keeps the pump functioning and leads to the retention of one Cl$^-$ ion and one water molecule per proton. Subsequent endosomal swelling and rupture leads to particle deposition in the cytoplasm (FIG. 1BIV)[18]. In the cytosol, the nanoparticles, which carry a sensor oligo complementary to an endogenous microRNA species, bind the microRNA (FIG. 1 BV), leading to the recruitment to the duplex of the endogenous RNA induced silencing complex (RISC) and cleavage of the oligo at a specific position in the seed region (FIG. 1BV1). This cleavage results in separation between the quencher and dye located at the ends of the sensor oligo, and fluorescent turn-on. The microRNA is released from the complex and is free to catalyze subsequent cleavage reactions (FIG. 1 BVII). The described mechanism is thoroughly validated. It exploits the endogenous process of RNA interference, which is triggered by the presence of cytosolic single-stranded RNA oligonucleotides that are complementary to an endogenous microRNA. The proposed approach takes advantage of powerful signal amplification, since millions of nanoparticles/oligos are delivered per cell, using the delivery method developed by the inventors.

Results

The Sensor Design can Report on Individual miRNA Expression with High Sensitivity and Specificity (Cell-Free System)

To assess the feasibility of the proposed approach, a study was performed in which a cleavable sensor oligo was designed to detect miR-10b expression, as described above. MIR-10b has been implicated in epithelial to mesenchymal transition and breast cancer metastasis by multiple studies[17, 18,21]. Considering that one application of the herein described invention is profiling the expression of pro-metastatic miRNAs in breast tumor cells, miRNA-10b was targeted in these studies. Specifically, an RNA sensor oligonucleotide was designed that was completely complementary to the miRNA-10b seed region and was conjugated to a Cy5 dye at the 5' end and Iowa Black RQ quencher at the 3' end. Its sequence was: AC AM UUC GGU UCU ACA GGG UA (SEQ ID NO: 8). Since the RNA oligo was 100% complementary to miRNA, it was cleavable. First the signal-to-background ratio was determined by incubating 100 nM of the sensor oligo with a 10 μg/ml of nuclease. As seen in FIG. 7, cleavage of the oligo resulted in a 566% fluorescence enhancement over the noncleaved oligo incubated in RNase-free conditions. In these studies, the oligo was terminally labeled with the dye and quencher. Consequently, the two were separated by 22 nucleotides (7.5 nm). In future studies, the oligo will be internally labeled and have a 10-nucleotide (nt) distance (3.4 nm) between the dye and quencher, which is expected to result in an >95% quenching efficiency and reduced background. To determine the sensitivity and specificity of detection with the minimum number of variables, a cell-free assay was designed, based on previously performed studies[22,23]. Studies were performed in the metastatic human breast cancer cell line MDA-MB-231-luc-D3H2LN (Caliper Life Sciences, Hopkinton, Mass.). Briefly, the cells were lysed, as described in[22, 23] Half of the lysates were incubated for 30 min. at 37° C. with a 10-fold excess of anti-miR10b locked nucleic acid (LNA) antisense oligonucleotides to miR-10b (ASO, Exiqon, Woburn, Mass.). LNA modification prevents these ASO from cleavage by miRNA and instead leads to inhibition of miRNA function (termed miR-10b-depleted control). The second half of the cell lysates was incubated with irrelevant oligo (SCR ASO), which does not bind miR-10b or any other of the annotated miRNAs and leaves miR-10b active. Following, the miR-10b sensor oligo was titrated into the miR-10b-depleted and miR-10b-active lysates (100 nM 3.1 nM) and incubated for 2 hrs at 37° C. The reaction was stopped by the addition of proteinase K buffer. Fluorescence from the sensor oligo was then recorded using epifluorescence optical imaging (Ivis Spectrum, 649 nm excitation; 670 nm emission). As seen in FIG. 8A, there was distinctive fluorescence enhancement with increased concentration of the sensor oligo in the lysates in which miR-10b was active after treatment with irrelevant oligo (SCR ASO). On the contrary, the lysates in which miRNA-10b was depleted (inhibited) by incubation with miR-10b ASO the signal was significantly lower. Using linear regression analysis (FIG. 8B) and the formula 3(sigma)/slope, a detection limit of 13.4 nM was calculated. However, it is posited that an optimized sensor design with internally conjugated fluorophores will have an even lower limit of detection, because in that design, background fluorescence will be reduced. Regarding the specificity of detection, it is concluded that the assay is highly specific, since the ASO used in the miR-10b-inhibited control is >99% specific for miR-10b (Exiqon, Woburn, Mass.). The precise level of specificity, however, will be quantified, as proposed, by testing sensor oligos with 1, 2, or 3-nucleotide mismatches.

Finally, cleavage of the sensor oligo by miR-10b-RISC was confirmed using gel electrophoresis (100 nM and 25 nM are shown but cleavage was confirmed at 50 nM and 12.5 nM as well in a separate experiment). This indicated that the observed fluorescence enhancement is the result of cleavage of the sensor oligo and confirmed that miR-10b can mediate cleavage of the substrate oligo as designed, despite the fact that none of its known mRNA targets are regulated by cleavage. Electrophoresis was performed as described in previous publications[22,23] (FIG. 8C), using sensor oligo or sensor oligo+ASO in water as positive controls.

The Sensor can Report on miRNA Expression in Intact Cells.

Figure 9A:
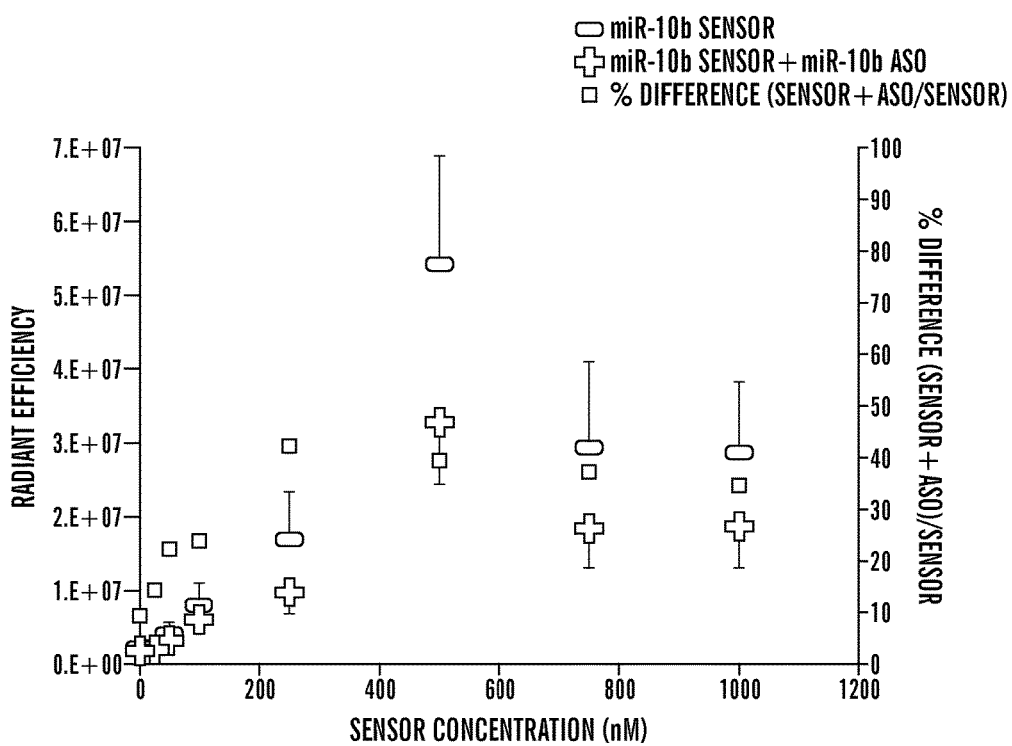
FIG. 9A-FIG. 9E shows experimental results that indicate miR-10b detection in intact cells.
Figure 9B:
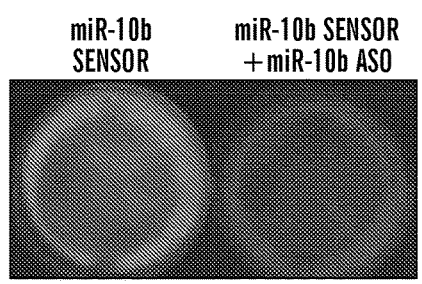
Figure 9C:
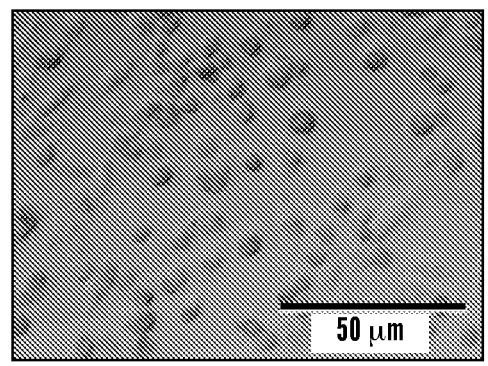
Figure 9D:
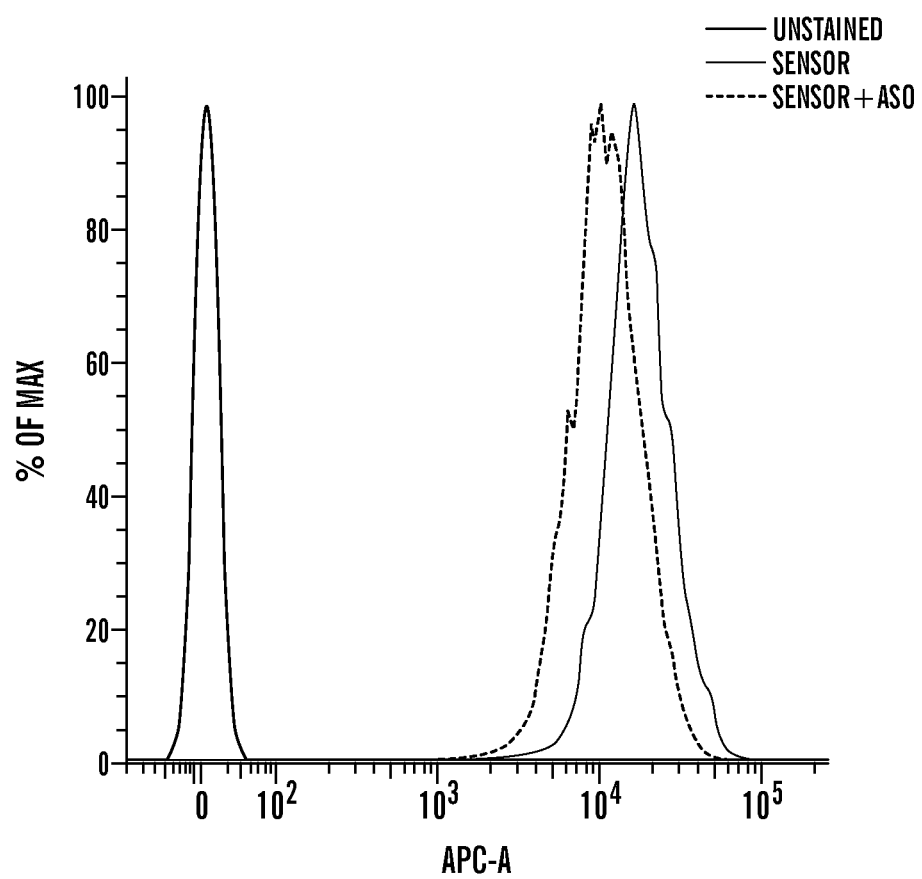
Figure 9E:
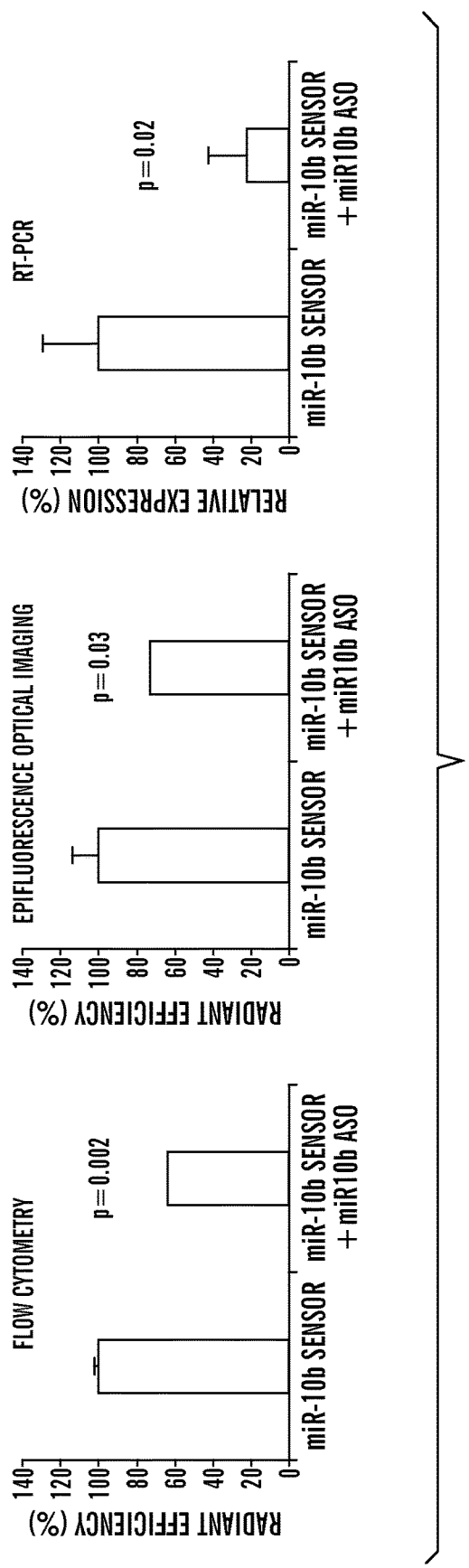

To test the hypothesis that the sensor as designed will be capable of reporting on miRNA expression in intact cells, MDA-MB-231-luc-D3H2LN cells were incubated with miR-10b-specific sensor at concentrations ranging from 25 to 1000 nM. MiR-10b depleted cells obtained by inhibiting miR-10b with ASO (using lipofectamine transfection) served as control. Following overnight incubation, cell fluorescence was examined as above (Ivis Spectrum Imaging System). As shown in FIGS. 9A and B, there was a significant difference in signal between the cells treated with the sensor specific to miR-10b and the miR-10b-depleted control cells ($p<0.05$). These differences were independent of sensor concentration above 250 nM. Nevertheless, the expected sensitivity of the method is higher due to the reduction in background fluorescence of the proposed optimized design discussed below. Fluorescence microscopy using a 250 nM concentration of the sensor revealed that cells could easily be delineated based on fluorescence from the sensor, which is an important element in a potential histopathological setting aimed at identifying cells with high metastatic potential (FIG. 9C). Finally, as an illustration of a related application, flow cytometry was used to compare cells treated with sensor alone or pretreated with the ASO (FIG. 9D). That experiment confirmed the observations using epifluorescence (Nis Spectrum) that the proposed approach could quantitatively reflect differences in miRNA expression. Irrespective of the method used (flow cytometry or epifluorescence), the miRNA expression as measured by the approach of this invention was accurate, because it mirrored that measured by the gold-standard RT-PCR (FIG. 9E). Together, these results demonstrate the feasibility of the technology and approach described herein.

Sample data illustrating the ability to resolve four fluorophores are presented in FIG. 10. In this case, any single dye, two or three-dye combinations, and a mixture of all four dyes (FITC, Cy3®, DyLight®594, and IRDye®-700DX, 100 nM in PBS) were analyzed. The solutions were excited at 430, 500, 535, and 605 nm, and emission was collected from 500 nm to 750 nm. Radiant efficiency was recorded following spectral unmixing, as previously described[44]. The referenced publication further supports the feasibility of resolving fluorescence in several channels from the same region of interest, since it describes the application of the proposed spectral unmixing protocol.

Example 4—Validation and Optimization of Technology and Approach

A. Optimization of Technology for miRNA Profiling in Tumor Cells

The miRNA nanosensors can be further optimized to achieve nanomolar sensitivity and >95% specificity and to maximize cell uptake and nuclease resistance. To achieve this, a library of nanosensors will be synthesized for each of the candidate miRNAs. Specifically, common miRNAs identified in more than one study as mediators of breast cancer metastasis include miR-10b[19-21]; MiR-21[21, 24-27]; miR-200 family, including miR-200c and miR-141[28-30] and Ma-205[21,31,32]; MiR-9[28,33], and miR-31[34, 35]. Studies will specifically focus on miRNAs that relate to epithelial to mesenchymal transition and invasion and migration, as opposed to macroscopic tumor formation at the distant site. Therefore, miR-10b, 200c, and 141[21] will be the focus of the studies since they are most relevant to tumor cell invasion and migration and are also differentially expressed in clinical samples. Each nanosensor design will be tested in vitro in order to select the one with the highest nuclease stability, sensitivity, and specificity of detection.

Synthesis and Characterization

The synthesis and characterization of the MN nanoparticles will be performed as described in[15].

The oligos will be custom synthesized by Integrated DNA Technologies (Coralvilte, Iowa). Based on preliminary results, they will consist of a 20-25 nucleotide sequence (most miRNAs are 22-25 nucleotides in length) that is perfectly complementary around the seed region. This length is well within the limit of 10 nm (30 nucleotides) imposed by the physics of fluorescence energy transfer. The oligos will incorporate a thiol group, followed by a hexyl or PEG spacer, and the target oligo, incorporating a quencher and a fluorescent dye, located 5' and 3' respectively to the 8-nucleotide seed region (the conserved region recognized by the cognate microRNA). A non-fluorescent pan-quencher (QC-1, Li-Cor Biosciences, Lincoln, Nebr.) and the following dyes with emission maxima over 600 nm will be tested: AlexaFluor® 594; AlexaFluor® 647; IRDye®-700DX; Alexa Fluor® 750; and IRDye®-800. Special care in selecting the oligo sequence will be taken to avoid the potential for internal dimers and other secondary structures. To achieve the optimal balance between minimal background fluorescence/maximal fluorescent turn-on upon cleavage, maximal lability around the cleavage site, and nuclease stability, the following parameters will be varied: the identity and positioning of the quencher-dye pairs on the oligos, the positioning of RNA and DNA/LNA bases in the oligo, their modification (2-O-Me/phosphorothioate backbone) and the length of the oligo. Considering that the choice between mRNA degradation and translational repression is dependent on the degree of complementarity between the mRNA target and the miRNA seed region, it is postulated that oligonucleotide probes perfectly complementary around the miRNA seed region will be cleaved in a sequence-specific way. This is supported by recent research 36 37 and by preliminary results, in which the miR-10b-specific sensor oligonucleotide is cleaved by miR-10b, despite the fact that all of miR-10b's known mRNA targets are bound with imperfect complementarity and regulated by translational repression and not mRNA cleavage. Based on prior experience, it is expected to synthesize 23-25-nm MN, incorporating up to 40 oligonucleotides per nanoparticle.

In Vitro Testing

The functionality of the nanosensors will be tested in the highly metastatic MDA-MB-231-luc-D3H2LN cell line (Caliper Life Sciences, Hopkinton, Mass.) characterized for feasibility in preliminary results. Nanosensor uptake will be evaluated by iron assay and Prussian blue staining. The design with the highest uptake per cell will be selected for further studies. miRNA expression will be determined by RT-PCR as in preliminary results. miRNA activity, specificity, and sensitivity will be determined following incubation of the cells with the nanosensors for 48-72 hrs at 37° C. Following, the cells will be washed and examined by fluorescence using filters appropriate for the selected substrate oligos (each identified by distinct quencher-dye combinations). To assess the sensitivity of detection, testing will be performed first in a cell-free assay and then in intact cells, as described above, with increasing concentrations of the nanosensor, and will use as controls scrambled oligonucleotides or deletion/knockdown of the target gene using Exiqon's miRNA inhibitors (Exiqon, Woburn, Mass.). In addition, to determine the minimal number of miRNA targets detected by the method described herein, an experiment will be designed in which the cells will be transfected with increasing concentrations of irrelevant siRNA (Exiqon, Woburn, Mass.), ranging from 2-1000 copies per cell. Following, the cells will be analyzed in a cell-free and intact assay format, as described in the preliminary results, using a sensor oligo specific for the irrelevant siRNA sequence. The specificity of detection will be determined by incorporating 1, 2, and 3-base mismatches into the sensor oligo and performing the described cell free and intact-cell assay with the expectation that even a 1-base mismatch will be discriminated using the nanosensors based on fluorescence enhancement. This expectation is justified by the fact that these oligonucleotides are routinely used to detect single nucleotide polymorphisms by in situ hybridization (Exiqon, Woburn, Mass.). Serum stability is necessary to facilitate handling of the nanonsensors in a potential future clinical scenario. It will be assessed as described in[38]. Prior studies have demonstrated that conjugation of RNA oligonucleotides to a carrier (in this case MN), affords significant protection from nuclease digestion in vivo[15, 16, 38]. Therefore, the sensor oligos are expected to remain stable in serum. For subsequent studies, nanosensors with sensitivity <10 nM and over 95 specificity for their cognate miRNA will be selected. In addition, nanosensors will be selected with the following attributes: they are taken up by cells with an efficiency of at least $15 \times 10^6$ nanoparticles/cell following overnight incubation and they are completely stable in serum for at least 48 hrs.

Data Analysis and Interpretation

Correlations between different methods of miRNA analysis (RT-PCR and fluorescence using the nanosensors described herein) will be performed by Pearson product moment correlation. Comparisons between experimental and control probes (negative or positive) will be performed using Student's t-test. A p value 0.05 will be considered statistically significant. Nanoparticles functionalized with an irrelevant oligo (Exiqon, Woburn, Mass.) will be used as a negative control. Also, nanoparticles functionalized with an oligo specific for one of the classic reference small RNAs (SNORD38B, SNORD44) that demonstrate stable expression will be used as an internal positive control. In addition, cells with inhibited target miRNA will be used as a negative control. For the studies on specificity, the sensor oligonucleotides will be compared to oligonucleotides with 1, 2, and 3-base mismatches. In all of the studies, results will be quantified as follows: The cells will be incubated with an experimental oligo (complementary to a candidate miRNA) and a positive control oligo (complementary to SNORD38 or 44 and labeled with a different dye-quencher pair). Fluorescence intensity from the experimental oligos will be divided by that of the positive control and expressed as a ratio. This method of normalization is borrowed from quantitative PCR technology.

B. Detection of all miRNAs by the Nanosensors

The ability of the nanosensors to detect all miRNAs will be confirmed. In mammals, a large number of miRNAs do not primarily regulate gene expression by degradation of target mRNAs but rather by translational repression. However, recent research indicates that the prevalence of miRNA-dependent degradation targets in mammals is higher than previously thought and that the choice between mRNA degradation and translational repression is dependent on the degree of complementarity between the mRNA target and the miRNA seed region[36,37] This is also supported by the results, in which the miR-10b-specific sensor oligonucleotide is cleaved by miR-10b, despite the fact that all of miR-10b's known mRNA targets are regulated by translational repression and not mRNA cleavage. Another potential question that could be raised relates to the power of the quenching-dequenching mechanism for the generation of signal. The feasibility of this approach, however, has been demonstrated numerous times over the years and is well-established[39-41]. Commercially available and validated dye-quencher pairs will be used. The probes will be synthesized using −20-nucleotide oligos, labeled with a quencher-dye pair spanning the 8-nucleotide seed region. This is well within the limit of 5-10 nm (15-30 nucleotides) imposed by the physics of fluorescence energy transfer. The specific quenching efficiencies for the quencher dye pairs selected for these studies approach 99% at a distance of 3 nm (10 bases). (http://biosupport.licor.com/docs/QC-1DarkQuencher_v5.pdf). In addition, at this distance, steric hindrance will not present an issue, because these quencher-dye combinations are used commercially as sensors for caspase activity using cleavage of the 2.9-nm GDEVDGAK (SEQ ID NO: 13) octapeptide substrate (Li-Cor Biosciences, Lincoln, Nebr.; http://biosupport.licorcomidocs/QC-1Dark-Quencher v5.pdf). In these studies, a 10-nucleotide distance between the quencher and dye has a length of 3.4 nm (103.4 A/nucleotide=34 A=3.4 nm). For the IRDye®-700DX-QC-1 pair, the expected quenching efficiency at that distance will be 98.8%. In addition, the overall fluorescent turn-on upon de-quenching is expected to exceed that reported for 1:1 hybridization probes, since the method takes advantage of three signal amplification strategies: 1. A single miRNA will cleave numerous substrate oligos, since RNAI is a "catalytic" molecular mechanism; 2. A single nanoparticle will carry up to 40 substrate oligos, taking advantage of therhenomenon of multivalency[42,43]; 3. The number of nanoparticles taken up by the tumor cells is large ($15 \times 10^6$ nanoparticles/cell).

C. Use of the Technology as a Basic Research Tool by Profiling Pro-Metastatic miRNA Signatures in Human Cell Lines The nanosensors, as designed, will allow us to detect differences between poorly and highly metastatic cells. This will be confirmed in highly metastatic (MDA-MB-231, MDA-MB-435, Hs-578T, BT-549, and MDA-MB-436) and poorly-metastatic (MCF7, T-47D, and ZR-75-1) human breast cancer cell lines (ATCC, Manassas, Va.).

Overall Strategy and Methodology

The intact cells will be incubated with the nanosensors and examined using fluorescence optical imaging (Ivis Spectrum imaging system), confocal microscopy, and flow cytometry. Fluorescence intensity from the nanosensors will be recorded in channels specific for each nanosensor. Spectral unmixing will be used to separate fluorescence from the nanosensors. Fluorescence for each nanosensor will be normalized to an internal reference (SNORD38B or SNORD44). In addition, to evaluate nanosensor uptake, a standard iron assay (Pointe Scientific) will be performed according to the manufacturer's instructions.

Data Analysis and Interpretation

Data analysis will include assessment of sensor-oligo functionality, miRNA expression, and differences between cell lines (poorly-metastatic vs. metastatic). Correlations between different methods of miRNA analysis (RT-PCR and fluorescence using the nanosensors described herein) and between cell lines (metastatic vs. poorly-metastatic) and individual miRNA expression will be determined by Pearson product moment correlation. Comparisons between experimental and control nanosensors will be performed using Student's t-test. Nanoparticles functionalized with an irrelevant oligo with no known human targets (Exiqon, Woburn, Mass.) will be used as a negative control and nanoparticles functionalized with an oligo specific for one of the classic reference small RNAs (SNORD38B, SNORD44) will be used as a positive control.

The maximum number of nanosensors that can be resolved fluorescently will be determined. In the results discussed above, four fluorophores in the same region of interest have been successfully unmixed using the spectral unmixing tool of the Ivis Spectrum (Caliper Life Sciences, Hopkinton, Mass.). At least that number of targets in a single imaging session will be able to be resolved. Variables such as dye-quencher pairs, oligo sequences, lengths and densities per nanoparticle will be optimized.

D. Use of the Technology as a Clinical Diagnostic of Invasive Breast Cancer Using Human Biopsy Samples The nanosensors, as designed, will allow the diagnosis of invasive/metastatic disease in clinical biopsy samples, based on a pro-metastatic miRNA signature in primary tumor tissue. This signature will be manifested by changes in expression of miR-10b, 200c, and 141. This is consistent with the literature (miR-10b[19-21]; miR-200 family, including miR-200c and miR-141[28-30]).

Tissue Samples

Frozen breast tissue samples (n=15-20) were obtained from the Cooperative Human Tissue Network (CHTN) of the National Cancer Institute (NCI), the National Institutes of Health, Bethesda, Md. (http://faculty.virginia.edu/chtn-tma/home.html). From these biopsy samples the inventors have constructed tissue microarrays (TMAs) of human breast epithelium representing nonmetastatic and metastatic disease as determined by the pathologist at the CHTN participating hospital. The assay will be performed in situ. In this case, the TMAs will be incubated with the miR-10b, 200c, and 141 nanosensors together with an internal reference (SNORD38B or 44) nanosensor using a range of nanosensor concentrations (20-100 vg Fe/ml). Following, the TMAs will be examined using fluorescence confocal microscopy. An adjacent tissue slice will be stained with standard histopathological H&E stain to identify tumor-cell regions of interest (ROIs). These regions of interest will then be copied onto the fluorescent TMA. Over these ROIs, fluorescence intensity from the nanosensors will be recorded in channels specific for each nanosensor. Fluorescence intensity (FI) for each nanosensor will be normalized to the internal reference (SNORD38B, SNORD44) and represented as: Fl nanosensor X/FI nanosensor SNORD. This ratio will be correlated to clinical stage, histological grade and the presence of lymph node metastasis using Fisher's exact text. Multivariate Cox regression analysis will be used to determine the dependence of the ratio on receptor positivity, patient age, and prior treatment. In addition, a reference ratio will be determined for normal breast epithelium. The number of cells displaying a Fl ratio >2-fold different from this reference will be quantified as: number of tumor cells >2 or −2* reference/total number of tumor cells in R01. This analysis will allow the determination of the abundance of cells in the tissue that demonstrate aberrant miR expression, as a diagnostic/prognostic indicator of invasive disease. The findings from this methodology will be compared to the gold standard RT-PCR, which will be performed on the same tissues, as described in preliminary results (FIG. 9) and[17]. Correlations between different methods of miRNA analysis (RT-PCR and fluorescence using the nanosensors described herein) will be determined by Pearson product moment correlation. Comparisons between experimental and control nanosensors will be performed using Student's West. Nanoparticles functionalized with an irrelevant oligo with no known targets (Exiqon, Woburn, Mass.) will be used as a negative control and nanoparticles functionalized with an oligo specific for one of the classic reference small RNAs (SNORD38B, SNORD44) will be used as a positive control.

In the above discussed experiments, the following aspects are expected to be confirmed: (1) the ability to generate a >95% specificity and low nanomolar (<10 nM) sensitivity; (2) the measured miRNA abundance is highly correlated (Pearson correlation coefficient r>0.95) to miRNA expression measured by RT-PCR; (3) the technology gives the same result in 95 out of 100 assays; (4) the technology can be 5-fold faster, as sensitive, and at least 10 times less expensive than the current "gold standard" technology RT-PCR; (4) the technology can differentiate between highly metastatic and poorly metastatic breast cancer cell lines based on differential miRNA activity (Log 2(relative expression): of at least 1/−1); (5) in clinical samples, the technology can detect the emergence of invasive cellular phenotypes, manifested as at least a 2-fold change in the expression of pro-metastatic miRNAs in tumor cells; (4) in clinical samples, the technology can detect the emergence of an invasive cellular phenotype in a single cell.

REFERENCES FOR EXAMPLES 3-4

1. Pohlmann, C. & Sprinzl, M. Electrochemical Detection of MicroRNAs via Gap Hybridization Assay. *Anal Chem.*
2. Song, R., Ro, S. & Yan, W. In situ hybridization detection of microRNAs. *Methods Mo! Rio!* 629, 287-294.
3. Li, W., Zhao, B., Jin, Y. & Ruan, K. Development of a low-cost detection method for miRNA microarray. *Acta Biochim Biophys Sin (Shanghai)* 42, 296-301.
4. Husale, S., Persson, H. H. & Sahin, 0. DNA nanomechanics allows direct digital detection of complementary DNA and microRNA targets. *Nature* 462, 1075-1078 (2009).
5. Xu, F., Dong, C., Xie, C. & Ren, J. Ultrahighly sensitive homogeneous detection of DNA and microRNA by using single-silver-nanoparticle counting. *Chemistry* 16, 1010-1016.
6. Mandir, J. B. et al. Rapid determination of RNA accessible sites by surface plasmon resonance detection of hybridization to DNA arrays. *Anal Chem* 81, 8949-8956 (2009).
7. Driskell, Primera-Pedrozo, 0. M., Dluhy, R. A., Zhao, Y. & Tripp, R. A. Quantitative surface-enhanced Raman spectroscopy based analysis of microRNA mixtures. *App! Spectrosc* 63, 1107-1114 (2009).
8. Li, J, Schachermeyer, S., Wang, Y., Yin, Y. & Zhong, W. Detection of microRNA by fluorescence amplification based on cation-exchange in nanocrystals. *Anal Chem* 81, 9723-9729 (2009).
9. Havelda, Z. In situ detection of miRNAs using LNA probes. *Methods Mol Biol* 592, 127-136.
10. Lu, J. & Tsourkas, A. Imaging individual microRNAs in single mammalian cells in situ. *Nucleic Acids Res* 37, e100 (2009).
11, Nuovo, G. J. et al. A methodology for the combined in situ analyses of the precursor and mature forms of microRNAs and correlation with their putative targets. *Nat Protoc* 4, 107-115 (2009).
12, Silahtaroglu, A. N. et al. Detection of microRNAs in frozen tissue sections by fluorescence in situ hybridization using locked nucleic acid probes and tyramide signal amplification. *Nat Protoc* 2, 2520-2528 (2007).

13. Nelson, P. T. et al. Microarray-based, high-throughput gene expression profiling of microRNAs. *Nat Methods* 1, 155-161 (2004).
14. Moore, A., Weissleder, R. & Bogdanov, A., Jr. Uptake of dextran-coated monocrystalline iron oxides in tumor cells and macrophages. *J Magn Reson Imaging* 7, 1140-1145 (1997).
15. Medarova, Z., Pham, W., Farrar, C., Petkova, V. & Moore, A. In vivo imaging of siRNA delivery and silencing in tumors. *Nat Med* 13, 372-377 (2007).
16. Kumar, M., Yigit, M., Dal, G., Moore, A. & Medarova, Z. Image-guided breast tumor therapy using a small interfering RNA nanodrug. *Cancer research* 70, 7553-7561 (2010).
17. Yigit, M. V. et al. Context-dependent differences in miR-10b breast oncogenesis can be targeted for the prevention and arrest of lymph node metastasis. *Oncogene* (2012).
18. Akinc, A., Thomas, M., Klibanov, A. M. & Langer, R. Exploring polyethylenimine-mediated DNA transfection and the proton sponge hypothesis. *J Gene Med* 7, 657-663 (2005).
19. Ma, L., Teruya-Feldstein, J. & Weinberg, R. A. Tumour invasion and metastasis initiated by microRNA-10b in breast cancer. *Nature* 449, 682-688 (2007).
20. Ma, L. et al. Therapeutic silencing of miR-10b inhibits metastasis in a mouse mammary tumor model. *Nature biotechnology* 28, 341-347 (2010).
21. Baffa, R. et al. MicroRNA expression profiling of human metastatic cancers identifies cancer gene targets. *J Pathol* 219, 214-221 (2009).
22. Brown, K. M., Chu, C. Y. & Rana, T. M. Target accessibility dictates the potency of human RISC. *Nat Struct Mo! Biol* 12, 469-470 (2005).
23. Robb, G. B., Brown, K. M., Khurana, J. & Rana, T. M. Specific and potent RNAi in the nucleus of human cells. *Nat Struct Mot Biol* 12, 133-137 (2005).
24. Yan, L. X. et al. MicroRNA miR-21 overexpression in human breast cancer is associated with advanced clinical stage, lymph node metastasis and patient poor prognosis. *Rna* 14, 2348-2360 (2008).
25. Song, B. et al. MicroRNA-21 regulates breast cancer invasion partly by targeting tissue inhibitor of metalloproteinase 3 expression, *J Exp Clin Cancer Res* 29, 29 (2010).
26. Huang, T. H. et al. Up-regulation of miR-21 by HER2/neu signaling promotes cell invasion. *J Rio! Chem* 284, 18515-18524 (2009).
27. Zhu, S. et al. MicroRNA-21 targets tumor suppressor genes in invasion and metastasis. *Cell Res* 18, 350-359 (2008).
28. Gravgaard, K. H. et al. The miRNA-200 family and miRNA-9 exhibit differential expression in primary versus corresponding metastatic tissue in breast cancer. *Breast Cancer Res Treat* (2012).
29. Burk, U. et al. A reciprocal repression between ZEB1 and members of the miR-200 family promotes EMT and invasion in cancer cells. *EMBO Rep* 9, 582-589 (2008).
30. Dykxhoorn, D. M, et al. miR-200 enhances mouse breast cancer cell colonization to form distant metastases. *PLoS One* 4, e7181 (2009).
31. Wu, H., Zhu, S. & Mo, Y. Y. Suppression of cell growth and invasion by miR-205 in breast cancer. *Cell Res* 19, 439-448 (2009).
32. Gregory, P. A. et al. The miR-200 family and miR-205 regulate epithelial to mesenchymal transition by targeting ZEB1 and SIP1. *Nat Cell Biol* 10, 593-601 (2008).
33. Ma, L. et al. miR-9, a MYC/MYCN-activated microRNA, regulates E-cadherin and cancer metastasis. *Nat Cell Biol* 12, 247-256.
34. Valastyan, S., Chang, A., Benaich, N., Reinhardt, F. & Weinberg, R. A. Concurrent suppression of integrin alpha5, radixin, and RhoA phenocopies the effects of miR-31 on metastasis. *Cancer Res* 70, 5147-5154.
35. Valastyan, S. et al. A pleiotropically acting microRNA, miR-31, inhibits breast cancer metastasis. *Cell* 137, 1032-1046 (2009).
36. Bracken, C. P. et al. Global analysis of the mammalian RNA degradome reveals widespread miRNA-dependent and miRNA-independent endonucleolytic cleavage. *Nucleic acids research* 39, 5658-5668 (2011).
37. Bracken, C. P. et al. Global analysis of the mammalian RNA degradome reveals widespread miRNA-dependent and miRNA-independent endonucleolytic cleavage. *Nucleic Acids Res.*
38. Wang, P. et al. Combined small interfering RNA therapy and in vivo magnetic resonance imaging in islet transplantation. *Diabetes* 60, 565-571 (2011).
39. Tung, C. H., Mahmood, U., Bredow, S. & Weissleder, R. In vivo imaging of proteolytic enzyme activity using a novel molecular reporter. *Cancer Res* 60, 4953-4958 (2000).
40. Bremer, C., Bredow, S., Mahmood, U., Weissleder, R. & Tung, C. H. Optical imaging of matrix metalloproteinase-2 activity in tumors: feasibility study in a mouse model. *Radiology* 221, 523-529 (2001).
41. Ntziachristos, V., Tung, C. H., Bremer, C. & Weissleder, R. Fluorescence molecular tomography resolves protease activity in vivo. *Nat Med* 8, 757-760 (2002).
42. Hong, S. et al. The binding avidity of a nanoparticle-based multivalent targeted drug delivery platform. *Chem Biol* 14, 107-115 (2007).
43. Weissleder, R., Kelly, K., Sun, E. Y., Shtatland, T. & Josephson, L. Cell-specific targeting of nanoparticles by multivalent attachment of small molecules. *Nat Biotechnol* 23, 1418-1423 (2005).
44. Ran, C. & Moore, A. Spectral Unmixing Imaging of Wavelength-Responsive Fluorescent Probes: An Application for the Real-Time Report of Amyloid Beta Species in Alzheimer's Disease. *Molecular imaging and biology: M1B: the official publication of the Academy of Molecular imaging* (2011).

Example 5—Detection of miRNA Expression in Intact Cells Using Activatable Sensor Oligonucleotides A new method for detection of miRNA signatures in intact cells is described. This mechanism of miRNA detection is applicable to a variety of endogenous target miRNAs as useful biomarkers for diagnosis and prognosis in preclinical/clinical settings. The key advantage of the technology is the capacity for analysis in intact cells. This is important because it is only through such studies that one can capture the true dynamics of miRNA regulation of cell fate. Other unique features of the technology include its rapid, low-cost format that permits high-throughput studies.

A method of microRNA detection was developed that employs a powerful signal amplification strategy. In this approach each miRNA molecule mediates catalytic cleavage of its sensor substrate consisting of an RNA oligo fully complementary to the target miRNA. This results in the cleavage of numerous synthetic substrates by a single miRNA-RISC complex. The described technology offers the possibility for miRNA detection using a simple, inexpensive ($40/L of assay solution), and rapid (~2 hr for 96 samples) assay format.

Figure 12A:
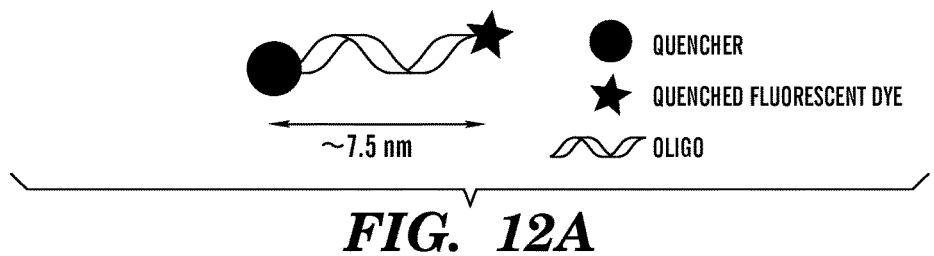
FIG. 12A-FIG. 12B shows Sensor design (FIG. 12A) and mechanism of action (FIG. 12B).
Figure 12B:
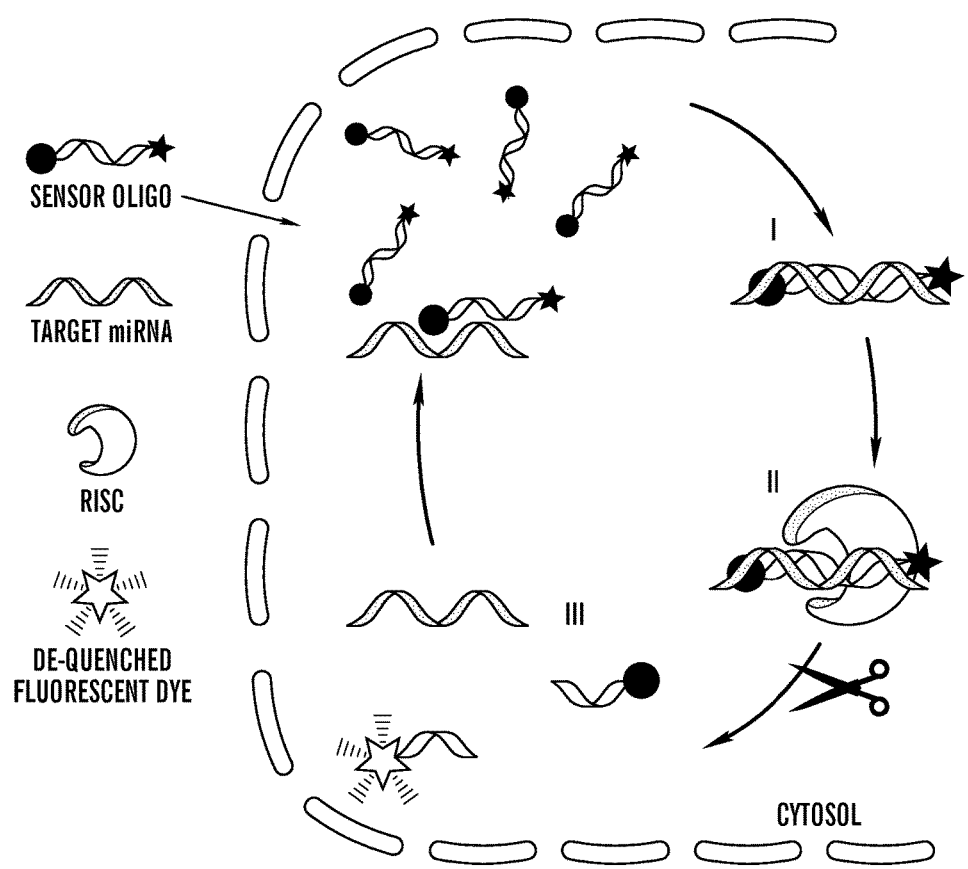

The specific mechanism behind the technology is described in FIG. 12. The sensor oligonucleotides are composed of RNA bases, are cleavable (non-stabilized by chemical modification) around the seed region (the conserved region within which the microRNA engages the RNA substrate), and are labeled with a fluorescent dye-quencher pair, so that upon cleavage of the oligonucleotide by the microRNA-RISC, fluorescence enhancement is observed (FIG. 12A). Upon internalization of the sensor oligos by the cell, the sensors efficiently engage the endogenous cytosolic RNA interference apparatus in a sequence-specific way. The sensor oligos were designed to be fully complementary to endogenous miRNA species and, as such, to base pair with their miRNA targets (FIG. 12BI). This binding event leads to the recruitment to the duplex of the endogenous RNA induced silencing complex (RISC) (FIG. 12BII) and cleavage of the oligo at a specific position in the seed region (FIG. 12BIII). This cleavage results in separation between the quencher and dye located at the ends of the sensor oligo, and fluorescence turn-on. The microRNA is released from the complex and is free to catalyze subsequent cleavage reactions (FIG. 12BIII).

Here the feasibility of the approach was demonstrated by focusing on one miRNA (miR-10b) implicated in breast cancer metastasis (Yigit, et al., 2012; Baffa, et al., 2009; Ma, et al., 2010; Ma, et al., 2007). However, this methodology can be applied for the detection and profiling of miRNA expression in a wide variety of preclinical and clinical scenarios.

Experimental Procedures

Oligonucleotides.

The sensor oligonucleotide (5'-Cy5/rCrArCrArArArUrU-rCrGrGrUrU rCrUrArCrArGrGrGrUrA/IAbRQSp-3') (SEQ ID NO: 9) was purchased from Integrated DNA Technologies (Coralville, Iowa). The oligo was composed of RNA bases. The 5' and 3' ends of the sequence were modified with Cy5 (fluorescent dye) and Iowa Black RQ (quencher), respectively. miRNA-10b miRCURY LNA™ microRNA Inhibitors (termed ASO) were purchased from Exiqon (Woburn, Mass.).

Experiments to Determine Signal-to-Background Ratio of the Sensor Oligonucleotides.

The signal-to-background ratio of the sensor was determined by incubating 100 nM of the oligo with a 10 μg/ml of RNase and recording fluorescence intensity (IVIS Spectrum epifluorescence optical imaging system, Caliper, Hopkinton, Mass.; 649 nm excitation; 670 nm emission) against a noncleaved oligonucleotide control (sensor oligonucleotides incubated in RNase-free water).

Cells.

The metastatic human breast cancer cell line, MDA-MB-231-luc-D3H2LN, was purchased from Caliper Life Sciences (Hopkinton, Mass.) and cultured in Dulbecco's modified Eagle's medium (Sigma, Saint Louise, Mo.) supplemented with 10% FBS (Thermoscientific, Waltham, Mass.), 1% antibiotics (Invitrogen, Carlsbad, Calif.), and 2 mM L-glutamine, per the supplier's instructions. Mouse epithelial mammary gland tumor cell line, 4T1, was purchased from ATCC and maintained in RPMI supplemented with 10% FBS and 1% antibiotics as per ATCC guidelines.

Preparation of Cell Extracts.

The protocol was modified from (Brown, et al., 2005; Robb, et al., 2005). MDA-MB-231-luc-D3H2LN cells were washed three times with ice-cold PBS, pH 7.2, and lysed for 10 min on ice by gentle mixing in four packed cell volumes of cell lysis buffer (20 mM HEPES, pH 7.9, 10 mM NaCl, 1 mM MgCl2, 0.5 M sucrose, 0.2 mM EDTA, 0.5 mM DTT, 0.5 mM PMSF, 0.35% (v/v) Triton X-100). The nuclear fraction was removed by centrifugation at 760 g for 10 min at 4° C. The supernatant was transferred to new eppendorf tubes and cold buffer B (0.11 volumes; 20 mM HEPES, pH 7.9, 10 mM NaCl, 1 mM MgCl2, 0.35 M sucrose, 0.2 mM EDTA, 0.5 mM DTT, 0.5 mM PMSF) was added. Cytoplasmic extracts were quickly stored in aliquots at −80° C. The protein concentration of cell extract (8 mg/ml) was determined using Bradford protein assay (BIO-RAD, Hercules, Calif.).

miRNA-Mediated Sensor Cleavage (Cell-Free Assay).

Sensor oligonucleotide (3.125, 6.25, 12.5, 25, 50, 100 nM) was incubated with untreated cell extracts or cell extracts pre-treated with anti-miR10b locked nucleic acid (LNA) antisense oligonucleotides (ASO, Exiqon, Woburn, Mass. at a 10-fold excess of ASO to sensor). The extracts were incubated at 37° C. for 2 hr in the following buffer: 40% (v/v) cell extracts (80 μg), 1 mM ATP, 0.2 mM GTP, 1 U/μl RNasin (Promega, Madison, Wis.), 30 μg/ml creatine kinase, 25 mM creatine phosphate (Sigma, Saint Louis, Mo.), 2 mM MgCl2, 20 mM NaCl and buffer D (100 mM KCl, 20 mM HEPES, pH 7.9, 2% (v/v) glycerol, and 0.2 mM EDTA) in a final reaction volume of 25 μl. The cleavage reactions were stopped by adding eight volumes (200 μl) of proteinase K buffer (200 mM Tris-HCl, pH 7.5, 25 mM EDTA, 300 mM NaCl, 2% (w/v) SDS and 0.6 mg/ml proteinase K (Invitrogen, Carlsbad, Calif.). Reactions were incubated at 37° C. for 15 min. Fluorescence was recorded using IVIS spectrum optical imaging system (Cy5 channel; 649 nm excitation, 670 nm emission, cut off: 665, Perkin Elmer, Hopkinton, Mass.). For sensor cleavage analysis, samples were resolved on a gel and stained with ethidium bromide.

Transfection and miRNA-Mediated Sensor Cleavage (Intact Cell Assay).

For transfection, MDA-MB-231-luc-D3H2LN cells were plated in a black 96-well plate at a seeding density of 10,000 cells per well in 0.2 ml of growth medium consisting of DMEM with 10% FBS. Cells were grown at 37° C. for 24 hr, the medium was removed, and 100 μl of serum free media (no antibiotics) was added. Cells were then transfected with an excess of miRNA-10b ASO or SCR ASO (5 μM) using Lipofectamine RNAiMAX (Invitrogen, Carlsbad, Calif.), according to the manufacturer's instructions. Following, varying concentrations of miRNA-10b sensor oligonucleotide (0, 25, 50, 100, 250, 500, 750, 1000 nM) were added to all wells and the plate was incubated for additional 3 hr. The transfection media containing sensor oligonucleotide was removed, complete media were added to the cells, and the cells were incubated for 24 hrs. Fluorescence was recorded in the Cy5 channel using IVIS spectrum optical imaging system (649 nm excitation; 670 nm emission). For time course study, fluorescence from the same plate was recorded at the specified time points up to 48 hrs.

Apoptosis (TUNEL Assay).

At the end of the time course study, cells were subjected to TUNEL assay as described by the manufacturer (ApopTag; Chemicon) and analyzed under a fluorescence microscope (Nikon Eclipse 2000) using appropriate filter sets.

Fluorescence Confocal Microscopy.

Cells ($0.1 \times 10^6$) were grown on a cover slip in a twelve-well plate for 24 hr and transfected as above (ASO—5 μM, 2 hour; sensor oligonucleotide—250 nM, 5 hour). Following, the media were replaced with fresh FBS containing media and incubated for another 48 hr. The cells were then washed three times with Hank's buffered salt solution (HBSS) and fixed with 2% formaldehyde for 10 min. The cells were then washed three times with DPBS buffer and the cover slip was placed on a glass slide with Vectashield mounting medium (Vector Laboratories, Burlingame, Calif.). The slides were dried for 30 min. The cells were imaged by confocal microscopy in the Cy5 channel (sensor detection) using a Zeiss LSM 5 Pascal laser confocal microscope (Carl Zeiss Microscopy, Thornwood, N.Y.). Image acquisition and analyses were performed using Zeiss LSM 5 Pascal Confocal Microscopy Software (Release 3.2). The final images were color-coded blue for Cy5 (sensor oligonucleotide).

Flow Cytometry.

Cells ($0.2 \times 10^6$) were transfected as described above for confocal microscopy. The cells were washed twice with HBBS buffer and removed from the plate using Hank's-based enzyme-free cell dissociation buffer. The cells were then fixed in 2% paraformaldehyde at 4° C. for 1 hour and analyzed by flow cytometry using FACSCalibur (Becton Dickinson, Franklin Lakes, N.J.) equipped with the CellQuest software package.

miRNA Extraction and Real-Time Quantitative RT-PCR.

To measure the extent of miRNA-10b inhibition by the miR10b ASO, MDA-MB-231-luc-D3H2LN cells were transfected and processed as described for flow cytometry. The miRNA-enriched fractions were extracted using the miRNeasy mini kit, according to the manufacturer's protocol (Qiagen Inc, Valencia, Calif.). cDNA for miRNA-PCR was synthesized using a RT2 miRNA First Strand Kit (Qiagen Inc, Valencia, Calif.). Real-time PCR was performed using RT2 SYBR Green/ROX qPCR Master Mix kit (Qiagen Inc., Valencia, Calif.) according to the manufacturer's instructions (ABI7700 Real-Time PCR System). The primers (miRNA-10b and SNORD44) were purchased from Qiagen (Valencia, Calif.). Expression level of miRNA-10b was normalized to that of SNORD44. Relative expression was calculated by the ΔΔCt method.

Statistical Analysis.

Data are presented as mean±SD (n=3). Statistical analysis was performed using linear regression analysis, one-way ANOVA (for comparisons between 3 or more groups) or Student t-test (for comparison between two groups), as indicated in the Results. Data were considered significant if p≤0.05.

Results

The herein described study was performed in which a cleavable sensor oligo was designed to detect miR-10b expression. miR-10b has been implicated in epithelial to mesenchymal transition and breast cancer metastasis by multiple studies (Yigit, et al., 2012; Baffa, et al., 2009; Ma, et al., 2010; Ma, et al., 2007). Specifically, an RNA sensor oligonucleotide was designed that was completely complementary to the miRNA-10b seed region and was conjugated to a Cy5 dye at the 5' end and Iowa Black RQ quencher at the 3' end. Its sequence was: AC AAA UUC GGU UCU ACA GGG UA (SEQ ID NO: 10). First the signal-to-background ratio of the sensor was determined by incubating the oligo with RNase and recording fluorescence intensity against a noncleaved oligonucleotide control. As seen in FIG. 7, cleavage of the oligo resulted in a 566% fluorescence enhancement over the noncleaved oligo incubated in RNase-free conditions.

Figure 13A:
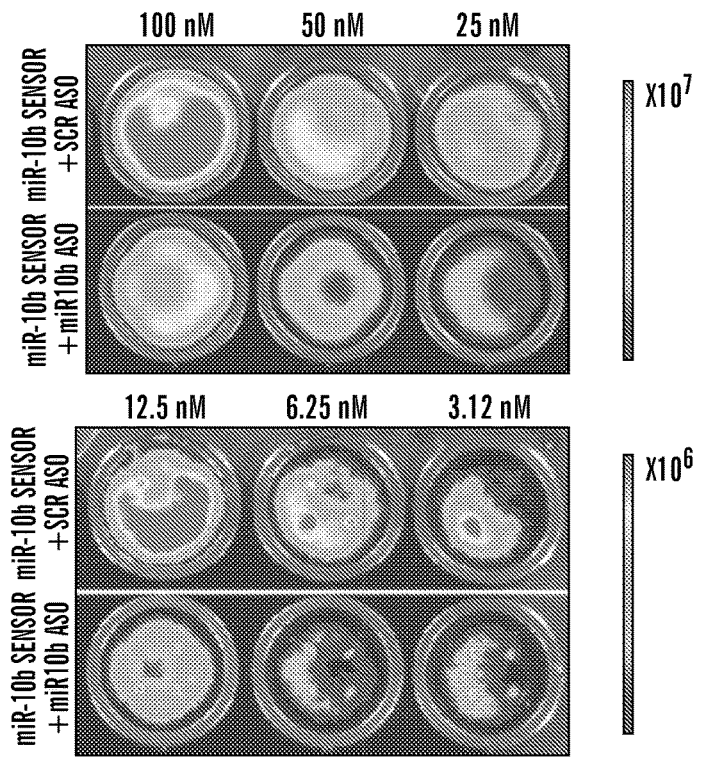
FIG. 13A-FIG. 13C shows experimental results that indicate miR-10b detection in a cell-free system.
Figure 13B:
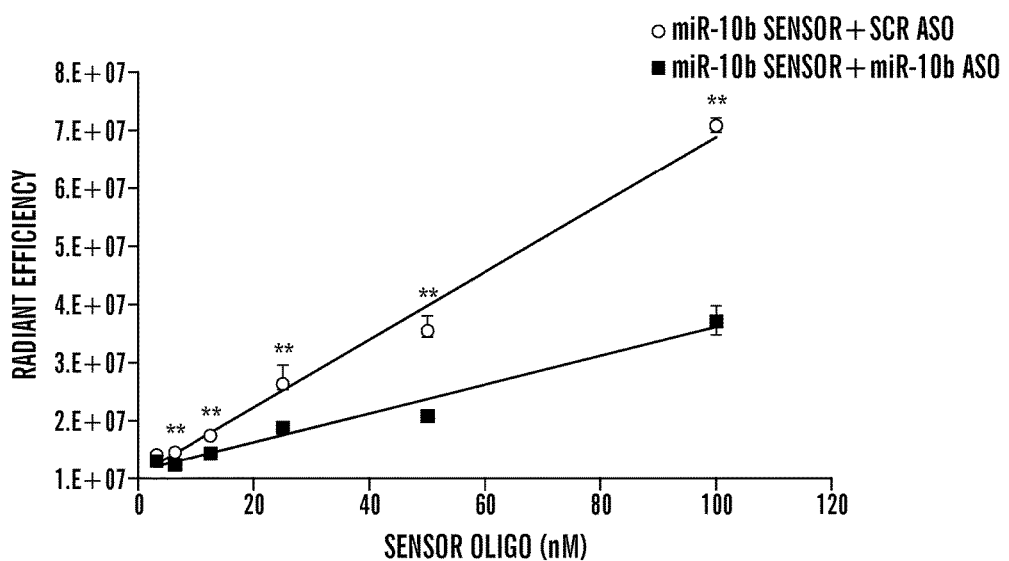
Figure 13C:
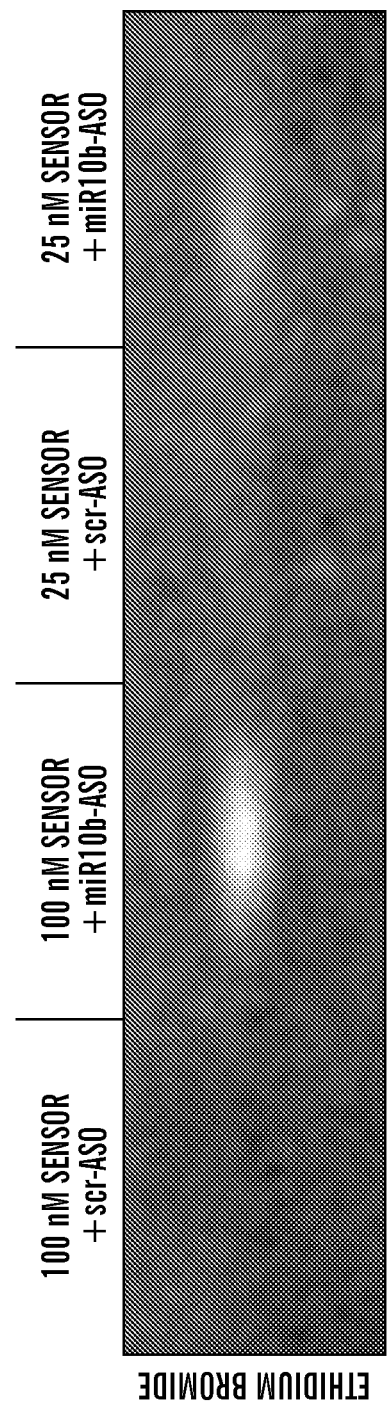

To determine the sensitivity of detection with the minimum number of variables, a cell-free assay was designed, based on reports in the literature (Brown, et al., 2005; Robb, et al., 2005). Studies were performed using cytoplasmic extracts from the metastatic human breast cancer cell line MDA-MB-231-luc-D3H2LN. In cytoplasmic extracts treated with anti-miR10b locked nucleic acid (LNA) antisense oligonucleotides to miR-10b (ASO) (termed miR-10b-depleted control), miRNA function was inhibited because of LNA modification on ASO. Consequentially, when the miR-10b sensor oligo was titrated into these ASO-treated extracts, a significant increase in fluorescence (FIG. 13A, bottom row) was not observed. In contrast, in the extracts incubated with irrelevant scrambled oligo (SCR ASO), which does not inhibit miR-10b or any other of the annotated miRNAs, distinctive fluorescence enhancement was observed with increased concentration of the sensor oligo (FIG. 13A, upper row). Using linear regression analysis (FIG. 13B) and the formula detection limit=3(sigma)/slope, a detection limit of 13.4 nM was calculated. The observed fluorescence enhancement was indeed due to sensor cleavage. Samples from the cell-free assay were resolved by gel electrophoresis (FIG. 13C). These experiments showed the presence of intact sensor (positive staining with ethidium bromide) in the samples where the miR10b specific RISC activity was inhibited by treatment with miR-10b ASO but not in the samples treated with SCR ASO in which miRNA-10b remained active and cleaved the sensor (no staining with ethidium bromide).

Figure 14A:
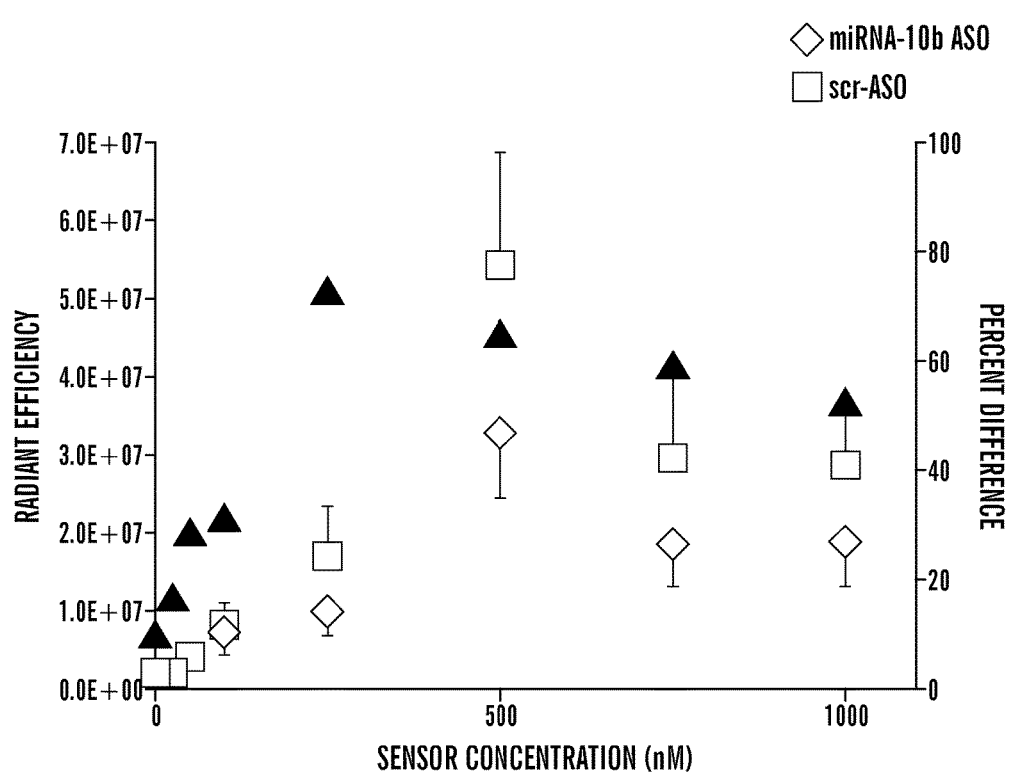
FIG. 14A-14F shows experimental results that indicate miR-10b detection in intact cells.
Figure 14B:
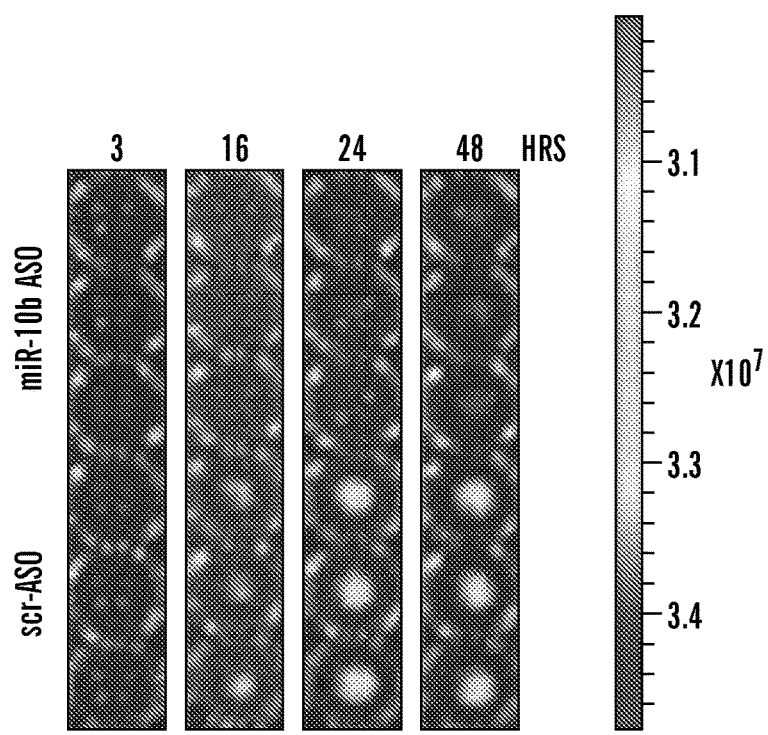
Figure 14C:
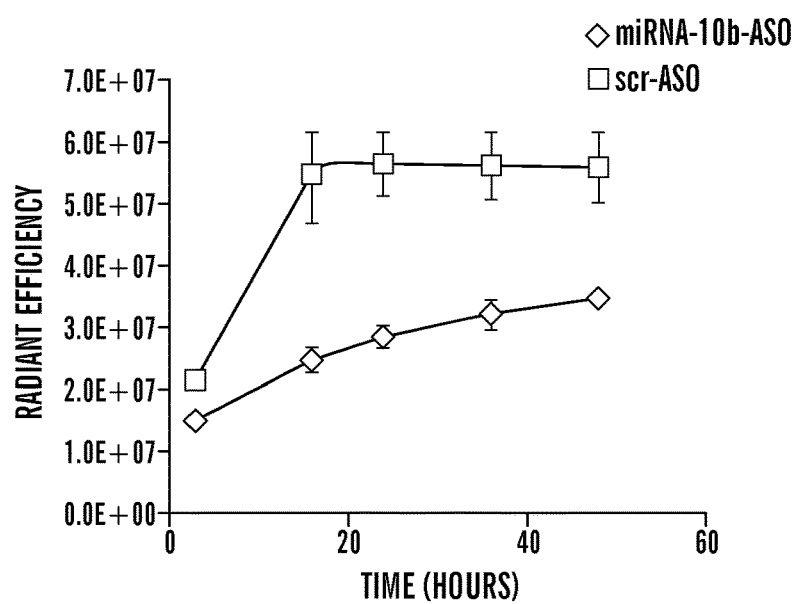
Figure 15:
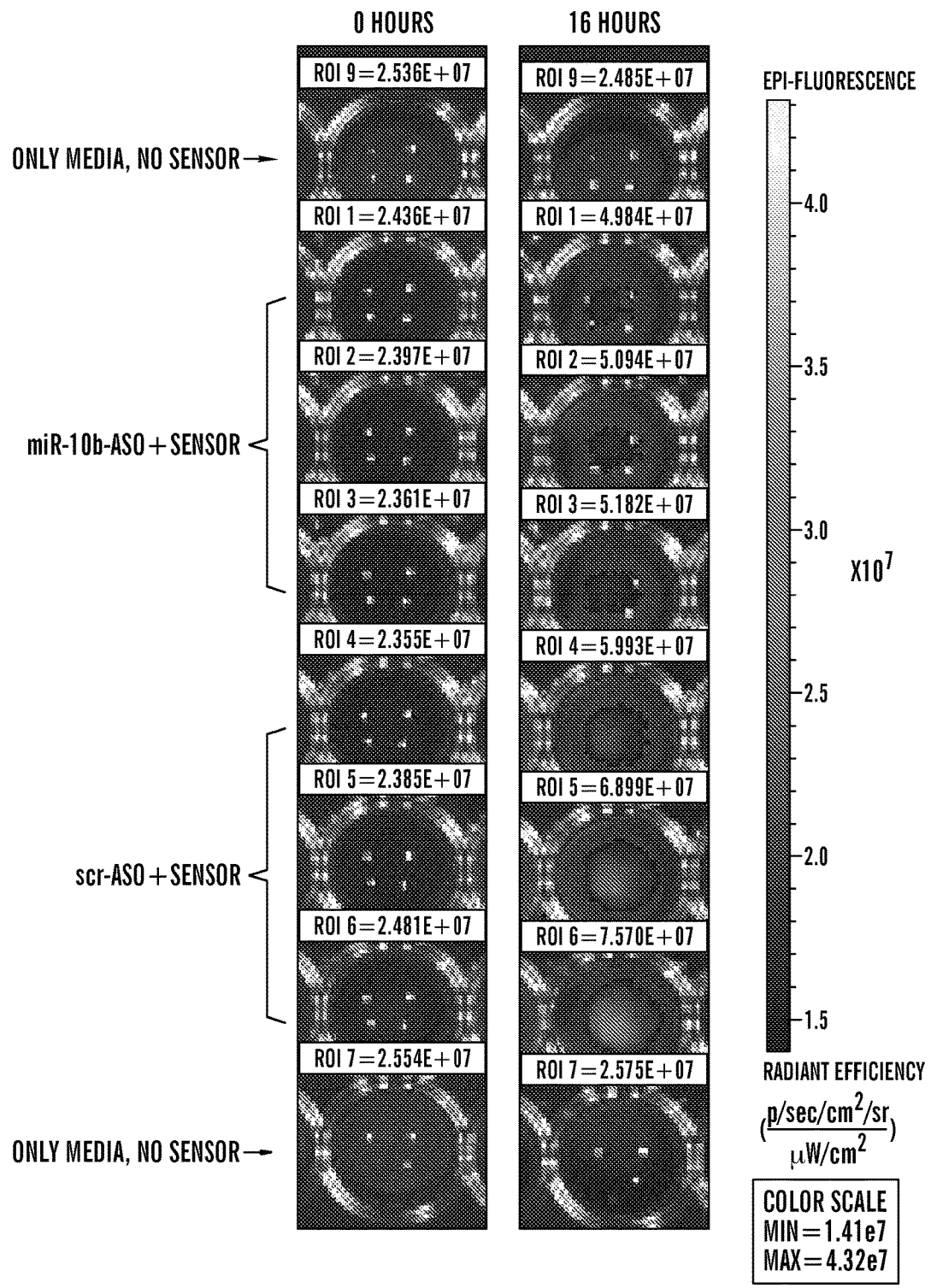
FIG. 15 is a set of fluorescent images showing experimental results that indicate fluorescence readings in wells with sensor are similar to fluorescence in wells without sensor. Fluorescence appears as a result of cleavage of the sensor and accumulates over a period of time (16 hours).
Figure 16:
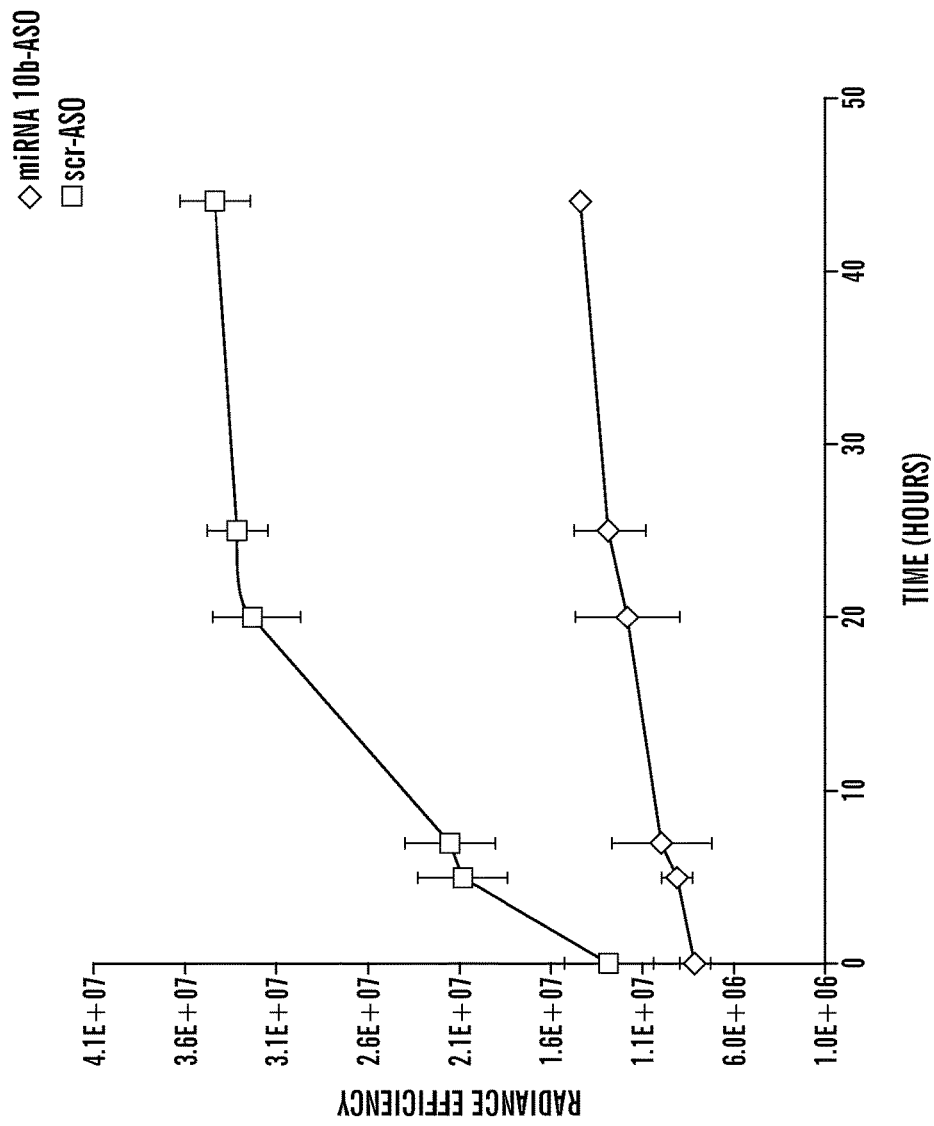
FIG. 16 shows experimental results that indicate similar fluorescence induction kinetics with 4T1 cells as observed in FIG. 15C with MDA-MB-231 cells. The results are shown in the form of a time course study with 4T1 mouse adenocarcinoma cells. Fluorescence was recorded after incubation with a fixed sensor concentration (125 nM). miRNA-10b activity was blocked by pre-treating the cells with antisense-oligo specific for miR-10b (miR-10b-ASO). For control, cells were pre-treated with scrambled antisense-oligo (scr-ASO).

MDA-MB-231-luc-D3H2LN cells were incubated with miR-10b-specific sensor oligo. miR-10b-depleted cells obtained by inhibiting miR-10b with ASO served as control. As shown in FIGS. 14A and 14B, there was a significant difference in signal between the miR-10b-active and the miR-10b-depleted control cells (p<0.05). These differences were independent of sensor concentration above 250 nM. Background fluorescence was negligible (FIG. 15, related to FIG. 14). Fluorescence appeared only after sensor cleavage and continued to increase over a period of time (FIG. 15, related to FIG. 14). To estimate the rate of sensor "turn-on" a time course study was performed at fixed sensor concentration of 125 nM. Maximum fluorescence intensity was reached within 16 hrs (FIG. 14C). In control cells depleted of miR-10b, the rate of sensor cleavage (non specific) was low and, even after 48 hrs of incubation, the fluorescence intensity did not reach maximum. A similar trend was observed with 4T1 breast adenocarcinoma cells (FIG. 16, related to FIG. 14).

Levels of apoptosis were assessed at the end of 48 hrs. No difference was observed between treated and control cells (Table 1, related to FIG. 14). For Table 1, After 48 hrs of incubation with the sensor, MDA-MB-231-luc-D3H2LN cells were stained for markers of apoptosis (ApopTag kit, Chemicon) and analyzed under a fluorescence microscope. Dead cells (visualized as green) were counted and expressed as percent of total cells visible under the field of view. A total of 5 measurements were made for each group.

TABLE 1

Incubation with the sensor does not adversely affect cell viability

|  | Apoptotic cells (%) | SD |
|---|---|---|
| Control | 1.46 | 0.38 |
| scr-ASO + Sensor | 1.40 | 0.08 |
| miR10b-ASO + Sensor | 1.48 | 0.46 |
| Only sensor | 1.12 | 0.35 |

Figure 14D:
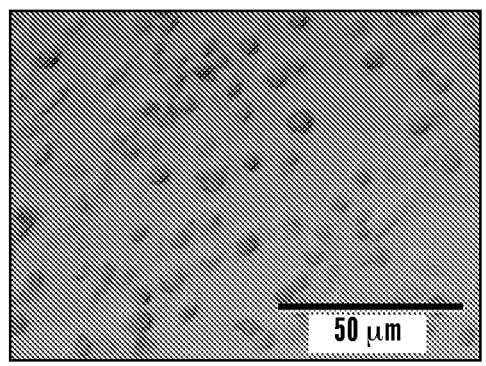

Fluorescence microscopy using a 250 nM concentration of the sensor revealed that cells could be easily delineated based on fluorescence from the sensor, which is an important element in a potential histopathological setting aimed at identifying cells with high metastatic potential (FIG. 14D).

Figure 14E:
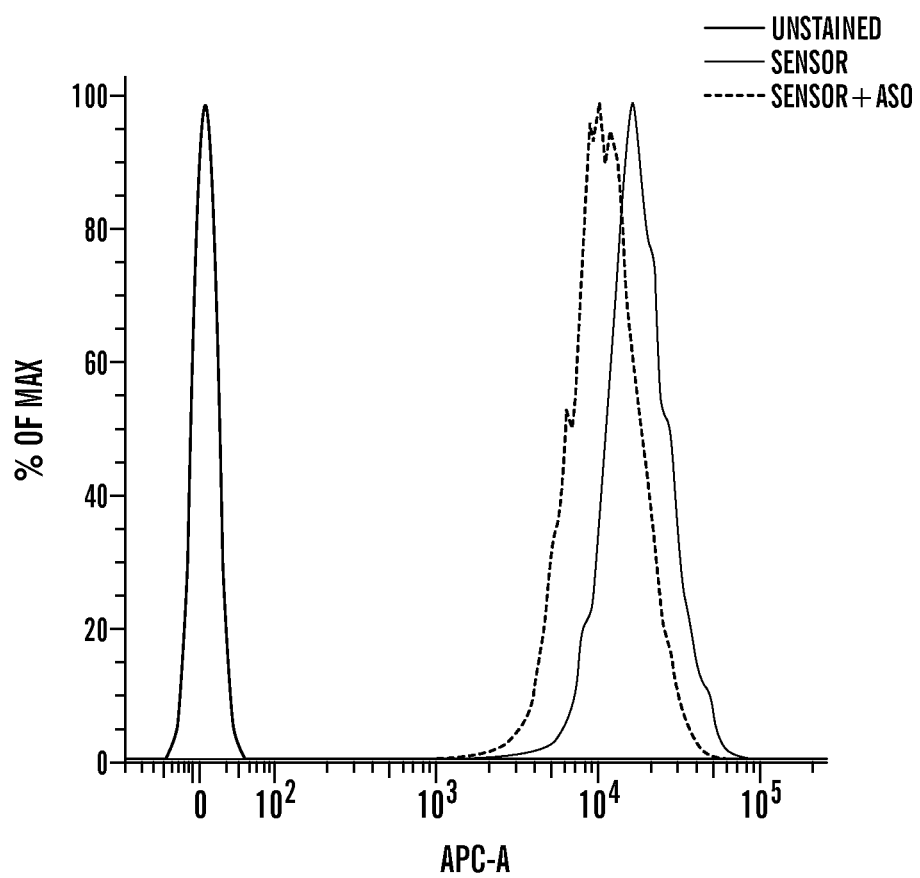
Figure 14F:
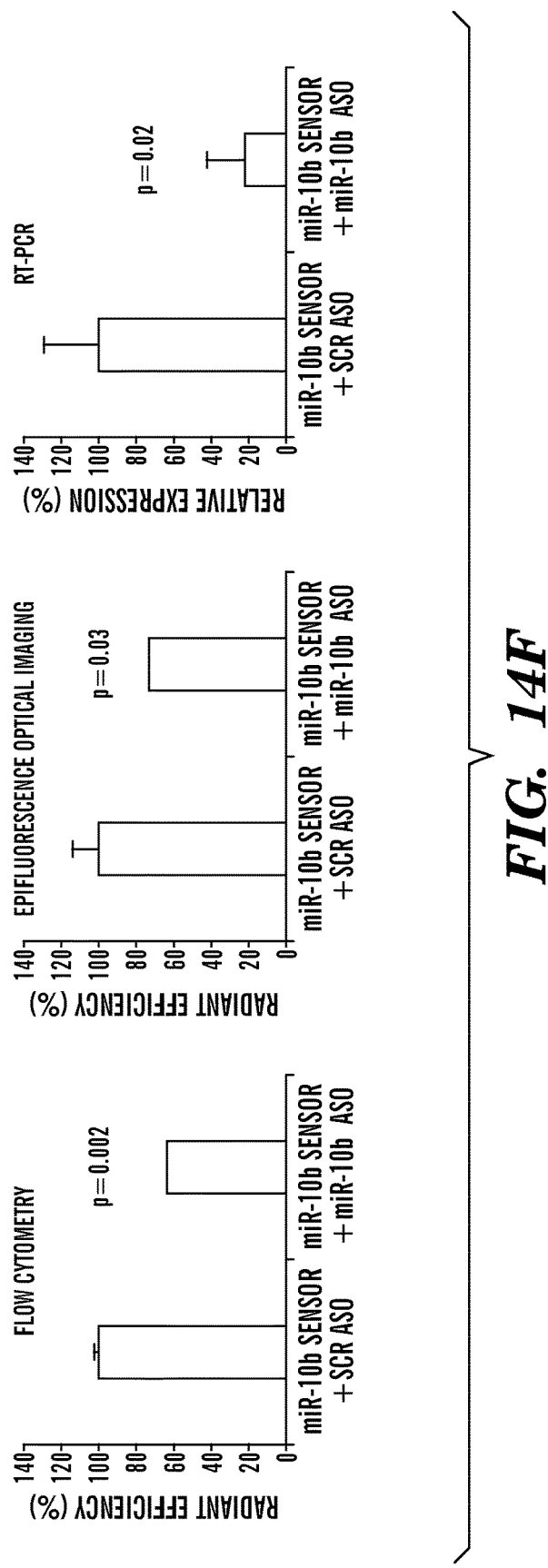

Finally, as an illustration of a related application, flow cytometry was used to compare miR-10b active or miR-10b-depleted cells (FIG. 14E). This experiment confirmed the observations using epifluorescence that the proposed approach could quantitatively reflect differences in miRNA expression. Irrespective of the method used (flow cytometry or epifluorescence), the miRNA expression as measured by the approach described herein was accurate, because it fell within one standard deviation of the measurement obtained by the gold-standard real-time qRT-PCR (FIG. 14F).

qRT-PCR was performed to determine the miR-10b content of MDA-MB-231 cells. It was found that MDA-MB-231 cells have around 400 copies of the miR-10b target per cell (7,500-fold less abundant than 18s rRNA, of which there are roughly $3.3 \times 10^6$ copies per cell. Furthermore, in cells in which miR-10b was inhibited using LNA antisense oligos, there was an 8-% reduction in miR-10b expression (measured by RT-PCR), corresponding to just 80 copies of miR-10b per cell. Since the detection method accurately reflected this difference in miR-10b abundance between the miR-10b-active and miR-10b-inhibited, this result indicates that the sensitivity of the sensors permits the quantification of targets present at levels below 100 copies/cell.

Discussion

Sensor oligonucleotides that can report on miRNA expression in intact cells haven been developed. Another unique feature of the technology is the speed and ease with which multiple miRNA targets can be analyzed in a low-cost high-throughput format. This capability holds potential in both pre-clinical and clinical settings. For example, as a research tool, it can be instrumental in elucidating the role played by miRNAs in regulating cell fate. Clinically, one can envision a scenario in which, as part of routine histopathology, biopsied tissues are examined by the proposed method to highlight individual cells with aberrant miRNA profiles that could signify high metastatic potential, precancerous lesions that are likely to progress, etc. Another scenario can take advantage of the capacity to isolate and analyze circulating tumor cells, as surrogates for a primary malignancy. Finally, a modified assay can be designed to permit analysis of non-cellular body fluids, provided that key components of the RNAi apparatus are exogenously supplied.

With these practical implications in mind, several issues need to be discussed. First, a question that can be raised has to do with the potential of the sensors to detect all miRNAs, since in mammals, a large number of miRNAs do not primarily regulate gene expression by degradation of target mRNAs but rather by translational repression. However, recent research suggests that the prevalence of miRNA-dependent degradation targets in mammals is higher than previously thought and that the choice between mRNA degradation and translational repression is dependent on the degree of complementarity between the mRNA target and the miRNA seed region (Bracken, et al., 2011). This hypothesis is also supported by the results showing that the miR-10b-specific sensor oligonucleotide is cleaved by miR-10b, despite the fact that all of miR-10b's known mRNA targets are regulated by translational repression and not mRNA cleavage.

A second issue has to do with the possibility to optimize the design of the sensors to minimize background fluorescence and increase sensitivity. It is thought that the detection limit can be enhanced by decreasing the length of the oligonucleotide (less than 22 nucleic acids) and by modifying the combination of fluorescent dye and quencher. In the current feasibility studies, the oligo was terminally labeled with the dye and quencher. Consequently, the two were separated by 22 nucleotides (7.5 nm). Alternatively, one could internally label the oligo and have a 10-nucleotide (nt) distance (3.4 nm) between the dye and quencher, which will result in an >95% quenching efficiency and reduced background. Specifically, sensors can be synthesized using ~20-nucleotide oligos, labeled with a quencher-dye pair spanning the 8-nucleotide seed region. This is well within the limit of 5-10 nm (15-30 nucleotides) imposed by the physics of fluorescence energy transfer. The specific quenching efficiencies for many commercial quencher-dye pairs approach 99% at a distance of 3 nm (10 bases). (http://biosupport.licor.com/docs/QC-1DarkQuencher_v5.pdf). In addition, at this distance, steric hindrance would not present an issue. As an example, the cited quencher-dye combinations are used commercially as sensors for caspase activity using cleavage of the 2.9-nm GDEVDGAK (SEQ ID NO: 13) octapeptide substrate (Li-Cor Biosciences, Lincoln, Nebr.; http://biosupport.licor.com/docs/QC-1DarkQuencher_v5.pdf). In one scenario, a 10-nucleotide distance between the quencher and dye would have a length of 3.4 nm (10×3.4 Å/nucleotide=34 Å=3.4 nm). For the IRDye® 700DX-QC-1 pair, the expected quenching efficiency at that distance will be 98.8%. In addition, the overall fluorescence turn-on upon de-quenching is expected to exceed that reported for 1:1 hybridization probes, since the method described herein takes advantage of a specific signal amplification strategy. Namely, a single miRNA will trigger the cleavage of numerous substrate oligos, since RNAi is a "catalytic" molecular mechanism. Unlike hybridization probes (e.g. molecular beacons and SmartFlare, Millipore) the sensor of this technology does not remain bound to and "hijack" the target. Consequently, the sensor of this technology is not expected to interfere with cellular function.

The current studies establish the feasibility of profiling miRNA signatures in intact cells and the availability of further optimization. This is important because it is only through such studies that one can capture the true dynamics of miRNA regulation of cell fate. Since the method is rapid and noninvasive, it allows for collection of time-course data in genuine cellular environments and thus gaining a better understanding of individual-to-individual variation, authentic molecular processes, and long-term trends.

What is claimed:

1. A nanosensor for detection of miRNA activity in a target cell comprising:
   a) a delivery particle comprising an iron oxide crystal coated with a polymer; and
   b) a sensor oligonucleotide covalently attached to the polymer, comprising:
      i) a seed region comprising a nucleic acid sequence that is completely complementary to a target miRNA and comprises a cleavage site which can be engaged by the target miRNA and cleaved by the target miRNA in complex with RNA induced silencing complex;
      ii) two non-seed regions that each flank the seed region and are each comprised of nucleic acid sequences complementary to the target miRNA to promote hybridization of the sensor oligonucleotide to the target miRNA; and
      iii) members of a quencher-fluorophore pair;
   wherein the quencher fluorophore pair members respectively flank the cleavage site and are separated by a distance that permits quenching of emitted fluorescent signal.

2. The nanosensor of claim 1, further comprising a targeting ligand covalently attached to the polymer.

3. The nanosensor of claim 2, wherein the targeting ligand is a peptide specific for an internalizing receptor located on the exterior plasma membrane of the target cell.

4. The nanosensor of claim 2, wherein the targeting ligand is selected from the group consisting of arginine-glycine-aspartic acid, folic acid, peptide EPPT (SEQ ID NO: 11), polyarginine peptide, and chlorotoxin.

5. The nanosensor of claim 2, wherein the polymer is selected from the group consisting of polyethylene glycol, dextran, polyvinylpyrrolidone, fatty acids, polypeptides, chitosan and gelatin, chitosan, polyethylenimine, and combinations thereof.

6. The nanosensor of claim 1, wherein the iron oxide crystal is from about 20-30 nm in diameter and the polymer is dextran.

7. The nanosensor of claim 2, wherein the sensor oligonucleotide and/or to the targeting ligand are covalently attached to the polymer by thiol crosslinking.

8. The nanosensor of claim 1, wherein the entire sensor oligonucleotide nucleic acid sequence is completely complementary to the target miRNA sequence.

9. The nanosensor of claim 1, wherein the sensor oligonucleotide is RNA, or a combination of RNA and one or more other modified nucleotides that hybridize with RNA in a sequence dependent manner, wherein at least the entire seed region is RNA.

10. The nanosensor of claim 1, wherein the sensor oligonucleotide is from about 18 to about 30 nucleotides in length or from about 20-25 nucleotides in length.

11. The nanosensor of claim 1, wherein the members are separated by a distance of about 9 to about 30 nucleotides.

12. The nanosensor of claim 1, wherein the fluorophore of the quencher-fluorophore pair has an emission maximal over 600 nm.

13. The nanosensor of claim 1, wherein the delivery particle is functionalized with amines to thereby facilitate endosomal swelling and rupture upon cellular uptake.

14. The nanosensor of claim 1, wherein the target miRNA is selected from the group consisting of let-7a, let-7d, let-7c, let-7i, miR-1, miR-100, miR-10a, miR-10b, miR-340, miR-155, miR-15b, miR-186, miR-222, miR-182, miR-210, miR-193b, miR-26a, miR-27a, miR-29a, miR-27b, miR-200c, miR-29c, miR-424, and miR-141.

15. The nanosensor of claim 1, wherein the delivery particle is covalently attached to the sensor oligonucleotide at a ratio selected from the group consisting of about 1:1, 1:10, about 1:20, about 1:30, about 1:40, and about 1:50.

16. The nanosensor of claim 1, wherein quenching is with an efficiency of greater than 95%.

17. The nanosensor of claim 1, wherein quenching is with an efficiency of about 99%.

18. A method for assessing the activity of one or more target miRNA in a target cell comprising,
   a) delivering an effective amount of one or more nanosensors of any of claims 1-17 to the target cell;
   b) detecting fluorescence emitted from the one or more nanosensors; and
   c) comparing the fluorescence detected with that of a normal control cell to thereby assess if the activity of the target miRNA(s) is higher than, lower than, or the same as in the target cell.

* * * * *

SEQUENCE LISTING

<160> NUMBER OF SEQ ID NOS: 13

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Asn Tyr Leu His Asn His Pro Tyr Gly Thr Val Gly
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ser Asn Pro Phe Ser Lys Pro Tyr Gly Leu Thr Val
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Leu His Glu Ser Thr Phe Thr Gln Arg Arg Leu
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Tyr Pro His Tyr Ser Leu Pro Gly Ser Ser Thr Leu
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ser Ser Leu Glu Pro Trp His Arg Thr Thr Ser Arg
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Leu Pro Leu Ala Leu Pro Arg His Asn Ala Ser Val
1               5                   10

<210> SEQ ID NO 7
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
acaaauucgg uucuacaggg ua                                              22

<210> SEQ ID NO 8
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
acamuucggu ucuacagggu a                                               21

<210> SEQ ID NO 9
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
cacaaauucg guucuacagg gua                                             23

<210> SEQ ID NO 10
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
acaaauucgg uucuacaggg ua                                              22

<210> SEQ ID NO 11
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Glu Pro Pro Thr
1

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ala Arg Arg Arg Arg Arg Arg Arg Cys
1               5

```
<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Asp Glu Val Asp Gly Ala Lys
1               5
```